(12) United States Patent
Krempl et al.

(10) Patent No.: US 7,744,902 B2
(45) Date of Patent: Jun. 29, 2010

(54) RESPIRATORY SYNCYTIAL VIRUS VACCINES EXPRESSING PROTECTIVE ANTIGENS FROM PROMOTOR-PROXIMAL GENES

(75) Inventors: Christine D. Krempl, Wuerzburg (DE); Peter L. Collins, Silver Spring, MD (US); Brian R. Murphy, Bethesda, MD (US); Ursula Buchholz, Silver Spring, MD (US); Stephen S. Whitehead, Montgomery Village, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1456 days.

(21) Appl. No.: 11/033,055

(22) Filed: Jan. 10, 2005

(65) Prior Publication Data

US 2006/0024797 A1 Feb. 2, 2006

Related U.S. Application Data

(63) Continuation of application No. 10/312,191, filed as application No. PCT/US01/20107 on Jun. 22, 2001, now abandoned, application No. 11/033,055, which is a continuation-in-part of application No. 09/602,212, filed on Jun. 23, 2000, now abandoned.

(60) Provisional application No. 60/213,708, filed on Jun. 23, 2000, provisional application No. 60/143,132, filed on Jul. 9, 1999.

(51) Int. Cl.
*A61K 39/155* (2006.01)

(52) U.S. Cl. .................. 424/211.1; 424/199.1

(58) Field of Classification Search ........................ None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,078 A | 1/1989 | Prince et al. |
| 4,800,478 A | 1/1989 | Takahashi |
| 5,922,326 A | 7/1999 | Murphy et al. |
| 5,993,824 A | 11/1999 | Murphy et al. |
| 6,264,957 B1 | 7/2001 | Collins |
| 6,689,367 B1 | 2/2004 | Collins et al. |
| 6,699,476 B1 | 3/2004 | Collins et al. |
| 6,713,066 B1 | 3/2004 | Collins et al. |

FOREIGN PATENT DOCUMENTS

| WO | WO 93/21310 | 10/1993 |
| WO | WO 97/06270 | 2/1997 |
| WO | WO 97/12032 B1 * | 4/1997 |
| WO | WO 98/02530 | 1/1998 |
| WO | WO 00/61737 | 1/2000 |
| WO | WO 01/04271 | 1/2001 |
| WO | WO 01/04321 | 1/2001 |
| WO | WO 01/04335 | 1/2001 |

OTHER PUBLICATIONS

Collins et al. PNAS USA, 1995, 92:11563-11567.*
Tang et al. J. Virology, 2001, 75(23):11328-11335.*

* cited by examiner

*Primary Examiner*—Stacy B Chen
(74) *Attorney, Agent, or Firm*—Woodcock Washburn LLP

(57) ABSTRACT

Recombinant respiratory syncytial virus (RSV) having the position of genes shifted within the genome or antigenome of the recombinant virus are infectious and attenuated in humans and other mammals. Gene shifted RSV are constructed by insertion, deletion or rearrangement of genes or genome segments within the recombinant genome or antigenome and are useful in vaccine formulations for eliciting an anti-RSV immune response. Also provided are isolated polynucleotide molecules and vectors incorporating a recombinant RSV genome or antigenome wherein a gene or gene segment is shifted to a more promoter-proximal or promoter-distal position within the genome or antigenome compared to a wild type position of the gene in the RSV gene map. Shifting the position of genes in this manner provides for a selected increase or decrease in expression of the gene, depending on the nature and degree of the positional shift. In one embodiment, RSV glycoproteins are upregulated by shifting one or more glycoprotein-encoding genes to a more promoter-proximal position. Genes of interest for manipulation to create gene position-shifted RSV include any of the NS1, NS2, N, P, M, SH, M2(ORF1), M2(ORF2), L, F or G genes or a genome segment that may be part of a gene or extragenic. A variety of additional mutations and nucleotide modifications are provided within the gene position-shifted RSV of the invention to yield desired phenotypic and structural effects.

4 Claims, 19 Drawing Sheets

Fig. 2.

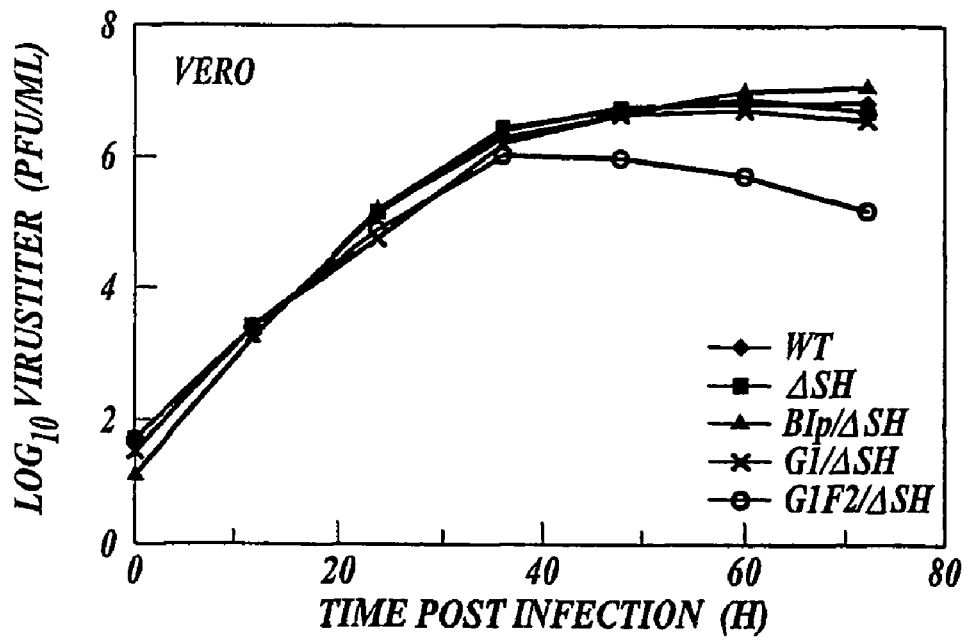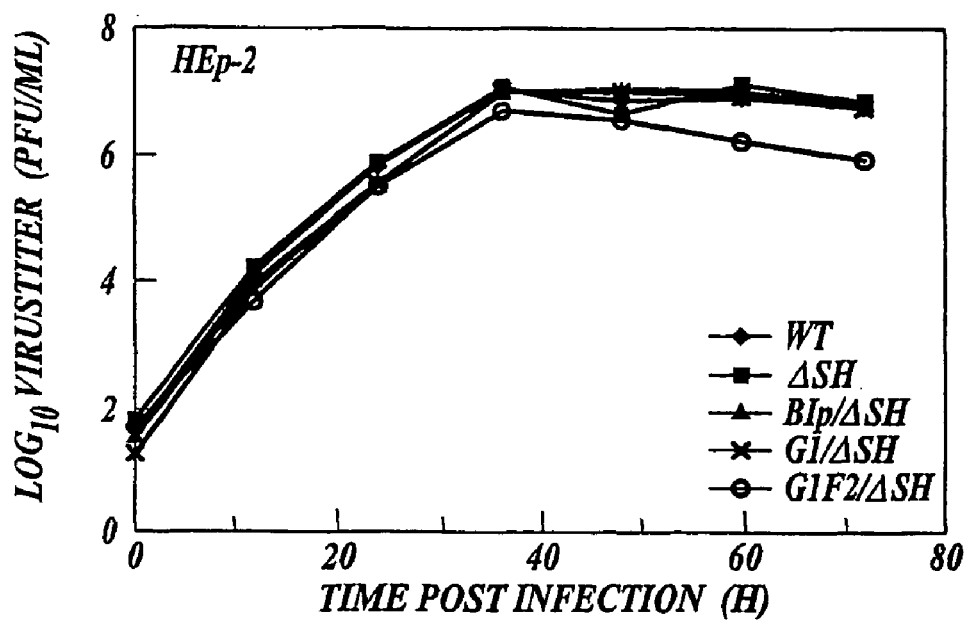
Fig. 3A.

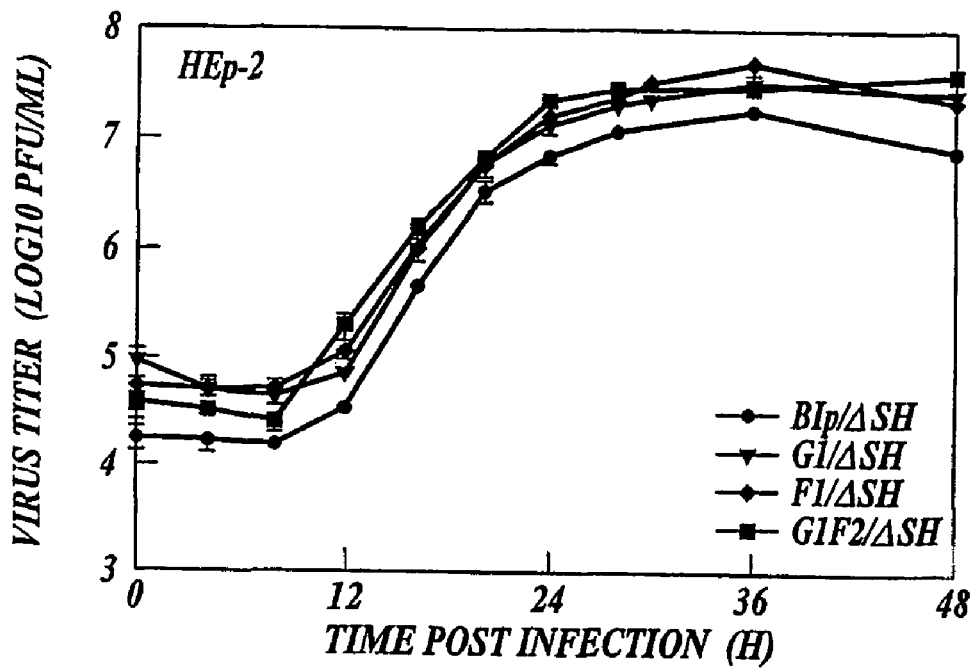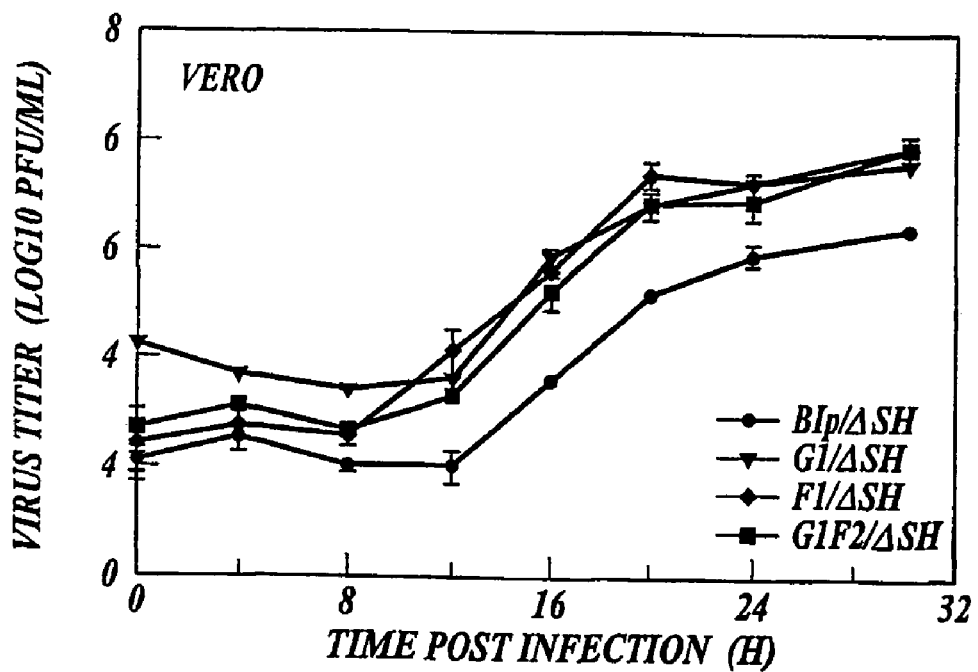
Fig. 3B.

TIME POST INFECTION (H)

| 0 12 24 36 48 60 72 | 0 12 24 36 48 60 72 | 0 12 24 36 48 60 72 |
|---|---|---|
| B1p/ΔSH | G1/ΔSH | G1F2/ΔSH |

*Fig. 4.*

☐ = GENE-START (GS)
▨ = GENE-END (GE)

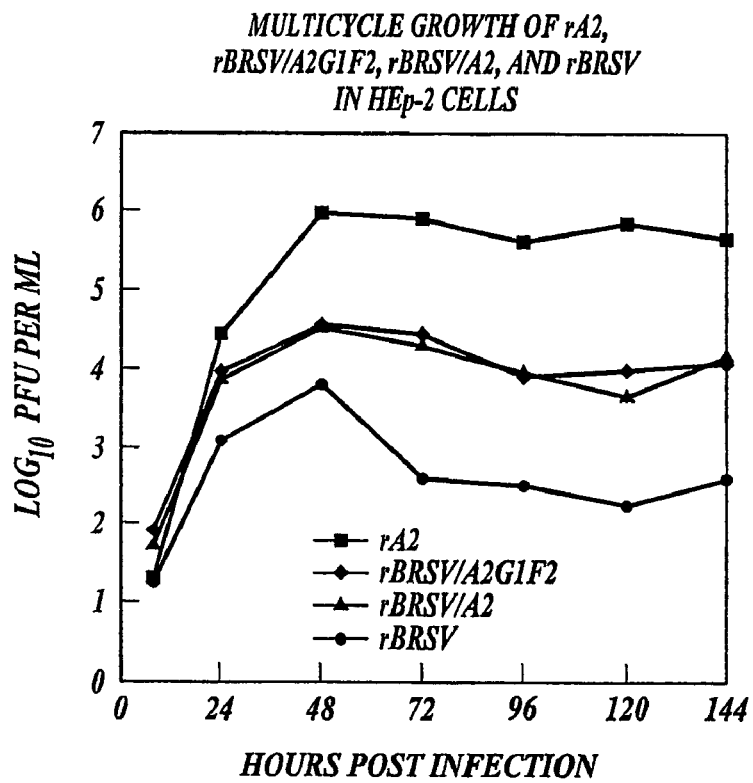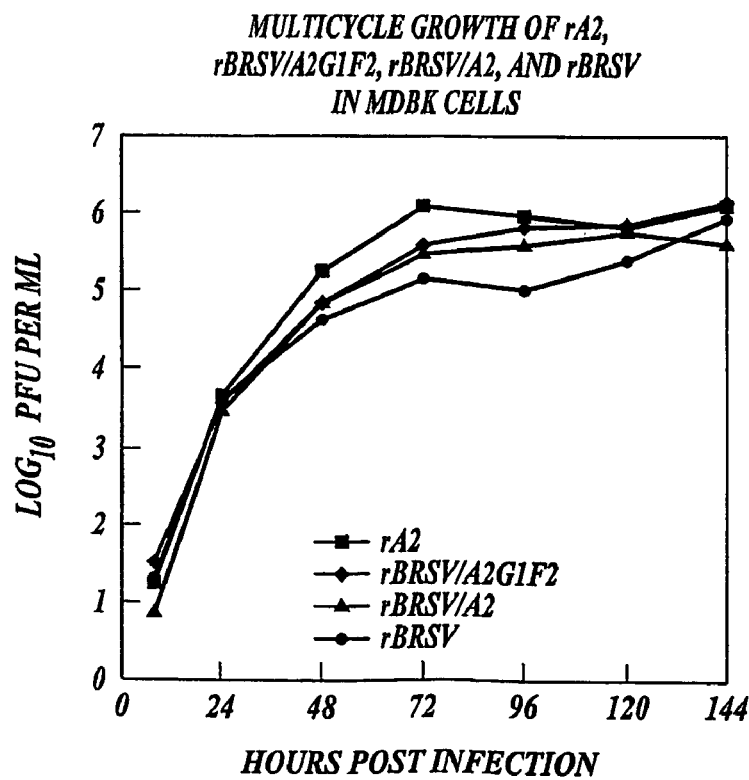
Fig. 7.

|  | ANTI HRSV G | ANTI HRSV F |
|---|---|---|
| rBRSV/A2 G1F2 | | |
| rBRSV/A2 | | |
| rA2 | | |

Fig. 8.

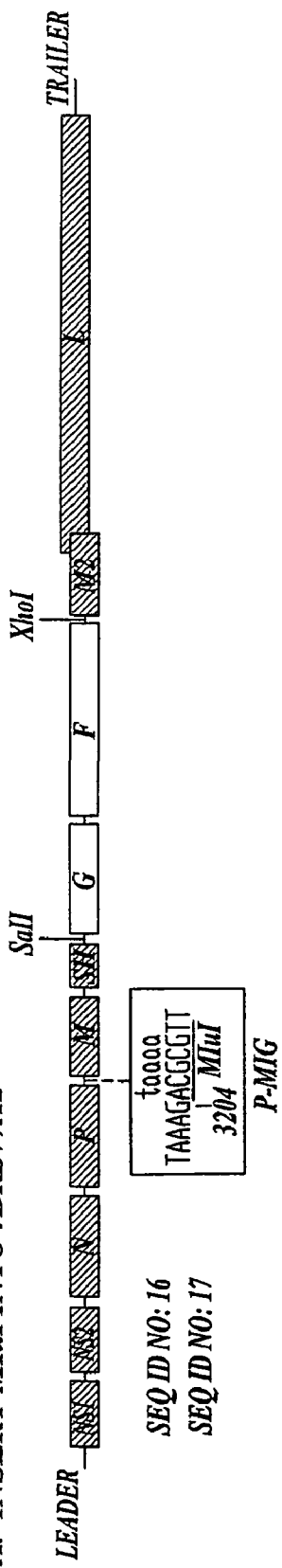
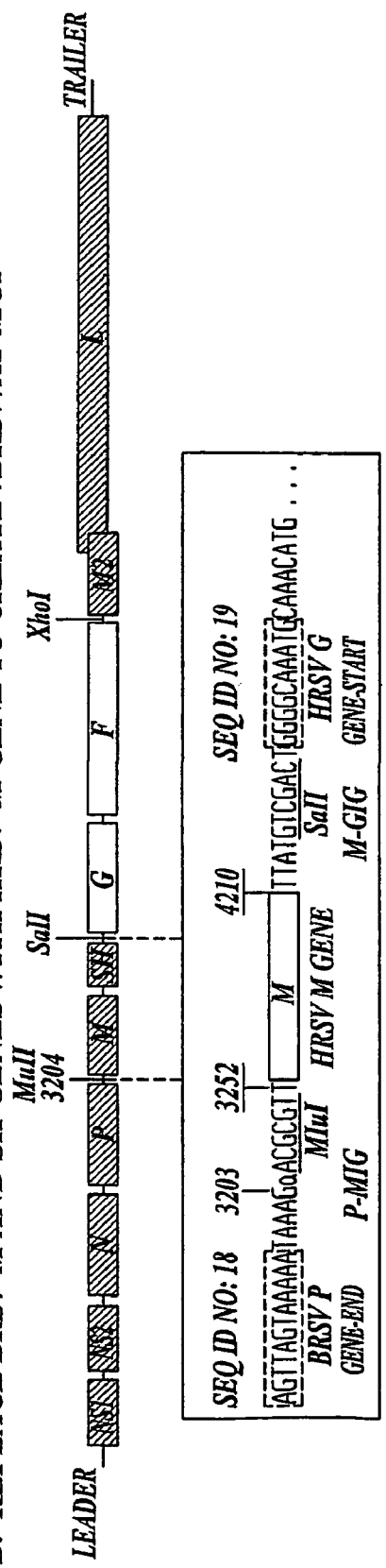
Fig. 9.
A. INSERT MluI INTO rBRSV/A2
B. REPLACE BRSV M

Fig. 12.

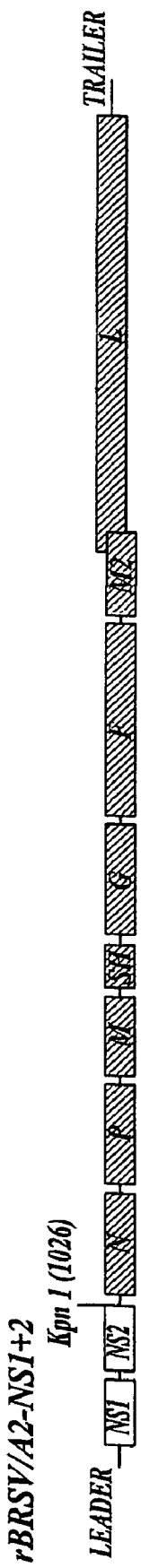
Fig. 13B.

SEQUENCE LISTING

```
<160> NUMBER OF SEQ ID NOS: 24

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence: Artificial
      Respiratory Syncytial Virus 1

<400> SEQUENCE: 1 catatt                                                                     6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence: Artificial
      Respiratory Syncytial Virus 2

<400> SEQUENCE: 2 cacaat                                                                     6

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Artificial
      Respiratory Syncytial Virus 3

<400> SEQUENCE: 3
ttaattaaaa acatattatc acaaa                                               25

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Artificial
      Respiratory Syncytial Virus 4
```

```
<400> SEQUENCE: 4
cacaattgca tgc                                                          13

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Artificial
      Respiratory Syncytial Virus 5

<400> SEQUENCE: 5
ttaattaaaa acacaatt                                                     18

<210> SEQ ID NO 6
<211> LENGTH: 64
<212> TYPE: DNA
<213> ORGANISM: Artificial Sequence
<220> FEATURE:
<223> OTHER INFORMATION: Description of Artificial Sequence: Artificial
      Respiratory Syncytial Virus 6

<400> SEQUENCE: 6
ttaaacttaa aaatggttta tgtcgaggaa taaaatcgat taacaaccaa tcattcaaaa        60
agat                                                                    64

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Artificial
      Respiratory Syncytial Virus 7

<400> SEQUENCE: 7
tcgagttaat acttgataaa gtagttaat                                         29

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Artificial
      Respiratory Syncytial Virus 8

<400> SEQUENCE: 8
taactacttt atcaagtatt aac                                               23

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Artificial
      Respiratory Syncytial Virus 9

<400> SEQUENCE: 9
ggggcaaata agaatttgat aagtaccact taaatttaac tcccttgctt agcgatg          57

<210> SEQ ID NO 10
<211> LENGTH: 9
<212> TYPE: DNA
<213> ORGANISM: Artificial Sequence
<220> FEATURE:
<223> OTHER INFORMATION: Description of Artificial Sequence: Artificial
```

Respiratory Syncytial Virus 10

<400> SEQUENCE: 10 ttagcgatg                                                                     9

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Artificial
      Respiratory Syncytial Virus 11

<400> SEQUENCE: 11
catattgggg caaataagc                                                         19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Artificial
      Respiratory Syncytial Virus 12

<400> SEQUENCE: 12
cacaatgggg caaataagc                                                         19

<210> SEQ ID NO 13
<211> LENGTH: 55
<212> TYPE: DNA
<213> ORGANISM: Artificial Sequence
<220> FEATURE:
<223> OTHER INFORMATION: Description of Artificial Sequence: Artificial
      Respiratory Syncytial Virus 13

<400> SEQUENCE: 13
ggggcaaata caagttaatt cgcggccgcc ccctctcttc tttctacaga aaatg                 55

<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence: Artificial
      Respiratory Syncytial Virus 14

<400> SEQUENCE: 14
gcggccgcta aatttaactc ccttgcttag cgatg                                       35

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Artificial
      Respiratory Syncytial Virus 15

<400> SEQUENCE: 15
cacaatgggg caaaataagc ttagcggccg c                                           31

<210> SEQ ID NO 16
<211> LENGTH: 5
<212> TYPE: DNA
<213> ORGANISM: Artificial Sequence
<220> FEATURE:
<223> OTHER INFORMATION: Description of Artificial Sequence: Artificial
      Respiratory Syncytial Virus 16

```
<400> SEQUENCE: 16 taaaa                                                              5

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Artificial
      Respiratory Syncytial Virus 17

<400> SEQUENCE: 17
taaagacgcg tt                                                     12

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Artificial
      Respiratory Syncytial Virus 18

<400> SEQUENCE: 18
agttagtaaa aataaagacg cgtt                                        24

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Artificial
      Respiratory Syncytial Virus 19

<400> SEQUENCE: 19
ttatgtcgac tggggcaaat gcaaacatg                                   29

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Artificial
      Respiratory Syncytial Virus 20

<400> SEQUENCE: 20

Arg Ala Arg Val Asn Thr
1               5

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Artificial
      Respiratory Syncytial Virus 21

<400> SEQUENCE: 21
agagctcgag tcaacacata gca                                         23

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Artificial
      Respiratory Syncytial Virus 22
```

```
<400> SEQUENCE: 22
tataaagtag ttaattaaaa atag                                          24

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence: Artificial
      Respiratory Syncytial Virus 23

<400> SEQUENCE: 23
agagctcgag ttaatacttg ataaagtagt taattaaaaa tag                     43

<210> SEQ ID NO 24
<211> LENGTH: 13
<212> TYPE: DNA
<213> ORGANISM: Artificial Sequence
<220> FEATURE:
<223> OTHER INFORMATION: Description of Artificial Sequence: BRSV gene
      end signal

<400> SEQUENCE: 24
agttatttaa aaa                                                      13
```

RESPIRATORY SYNCYTIAL VIRUS VACCINES EXPRESSING PROTECTIVE ANTIGENS FROM PROMOTOR-PROXIMAL GENES

This application is a continuation of U.S. patent application Ser. No. 10/312,191, filed Dec. 20, 2002 and now abandoned, which is a national stage filing of PCT/US01/20107, filed Jun. 22, 2001, which in turn claims priority of U.S. provisional application 60/213,708, filed Jun. 22, 2000.

This application is also a continuation-in-part of U.S. patent application Ser. No. 09/602,212, filed Jun. 23, 2000, now abandoned, which in turn claims priority of U.S. provisional application 60/143,132, filed Jul. 9, 1999.

All of the above applications are hereby incorporated by reference in their entirety.

BACKGROUND OF THE INVENTION

Human respiratory syncytial virus (HRSV) is the leading viral agent of serious pediatric respiratory tract disease worldwide (Collins, et al., *Fields Virology* 2:1313-1352, 1996). RSV outranks all other microbial pathogens as a cause of pneumonia and bronchiolitis in infants under one year of age. Virtually all children are infected by two years of age, and reinfection occurs with appreciable frequency in older children and young adults (Chanock et al., in *Viral Infections of Humans* 3rd ed., A. S. Evans, ed., Plenum Press, N.Y., 1989). RSV is responsible for more than one in five pediatric hospital admissions due to respiratory tract disease, and in the United States alone causes nearly 100,000 hospitalizations and 4,500 deaths yearly. (Heilman, *J Infect Dis* 161:402-6, 1990). In addition, there is evidence that serious respiratory tract infection early in life can initiate or exacerbate asthma (Sigurs, et al., *Pediatrics* 95:500-5, 1995).

While human RSV usually is thought of in the context of the pediatric population, it also is recognized as an important agent of serious disease in the elderly (Falsey, et al., *J. Infect. Dis.* 172:389-394, 1995). Human RSV also causes life-threatening disease in certain immunocompromised individuals, such as bone marrow transplant recipients (Fouillard, et al., *Bone Marrow Transplant* 9:97-100, 1992).

For treatment of human RSV, one chemotherapeutic agent, ribavirin, is available. However, its efficacy and use is controversial. There are also licensed products for RSV intervention which are composed of pooled donor IgG (Groothuis, et al., *N Engl J Med* 329:1524-30, 1993) or a humanized RSV-specific monoclonal antibody. These are administered as passive immunoprophylaxis agents to high risk individuals. While these products are useful, their high cost and other factors, such as lack of long term effectiveness, make them inappropriate for widespread use. Other disadvantages include the possibility of transmitting blood-borne viruses and the difficulty and expense in preparation and storage. Moreover, the history of the control of infectious diseases, and especially diseases of viral origin, indicates the primary importance of vaccines.

Despite decades of investigation to develop effective vaccine agents against RSV, no safe and effective vaccine has yet been achieved to prevent the severe morbidity and significant mortality associated with RSV infection. Failure to develop successful vaccines relates in part to the fact that small infants have diminished serum and secretory antibody responses to RSV antigens. Thus, these individuals suffer more severe infections from RSV, whereas cumulative immunity appears to protect older children and adults against more serious impacts of the virus.

The mechanisms of immunity in RSV infection have recently come into focus. Secretory antibodies appear to be most important in protecting the upper respiratory tract, whereas high levels of serum antibodies are thought to have a major role in resistance to RSV infection in the lower respiratory tract. RSV-specific cytotoxic T cells, another effector arm of induced immunity, are also important in resolving an RSV infection. However, while this latter effector can be augmented by prior immunization to yield increased resistance to virus challenge, the effect is short-lived. The F and G surface glycoproteins are the two major protective antigens of RSV, and are the only two RSV proteins which have been shown to induce RSV neutralizing antibodies and long term resistance to challenge (Collins et al., *Fields Virology*, Fields et al., eds., 2:1313-1352, Lippincott-Raven, Philadelphia, 1996; Connors et al., *J. Virol.* 65(3):1634-7, 1991). The third RSV surface protein, SH, did not induce RSV-neutralizing antibodies or significant resistance to RSV challenge.

An obstacle to developing live RSV vaccines is the difficulty in achieving an appropriate balance between attenuation and immunogenicity, partly due to the genetic instability of some attenuated viruses, the relatively poor growth of RSV in cell culture, and the instability of the virus particle. In addition the immunity which is induced by natural infection is not fully protective against subsequent infection. A number of factors probably contribute to this, including the relative inefficiency of the immune system in restricting virus infection on the luminal surface of the respiratory tract, the short-lived nature of local mucosal immunity, rapid and extensive virus replication, reduced immune responses in the young due to immunological immaturity, immunosuppression by trans-placentally derived maternal serum antibodies, and certain features of the virus such as a high degree of glycosylation of the G protein. Also, as will be described below, human RSV exists as two antigenic subgroups A and B, and immunity against one subgroup is of reduced effectiveness against the other.

Although RSV can reinfect multiple times during life, reinfections usually are reduced in severity due to protective immunity induced by prior infection, and thus immunoprophylaxis is feasible. A live-attenuated RSV vaccine would be administered intranasally to initiate a mild immunizing infection. This has the advantage of simplicity and safety compared to a parenteral route. It also provides direct stimulation of local respiratory tract immunity, which plays a major role in resistance to RSV. It also abrogates the immunosuppressive effects of RSV-specific maternally-derived serum antibodies, which typically are found in the very young. Also, while the parenteral administration of RSV antigens can sometimes be associated with immunopathologic complications (Murphy et al., *Vaccine* 8(5):497-502, 1990), this has never been observed with a live virus.

A formalin-inactivated virus vaccine was tested against RSV in the mid-1960s, but failed to protect against RSV infection or disease, and in fact exacerbated symptoms during subsequent infection by the virus. (Kim et al., *Am. J. Epidemiol.*, 89:422434, 1969; Chin et al., *Am J. Epidemiol.*, 89:449-463, 1969; Kapikian et al., *Am. J. Epidemiol.*, 89:405421, 1969).

More recently, vaccine development for RSV has focused on attenuated RSV mutants. Friedewald et al., (*J. Amer. Med. Assoc.* 204:690-694, 1968) reported a cold passaged mutant of RSV (cpRSV) which appeared to be sufficiently attenuated to be a candidate vaccine. This mutant exhibited a slight increased efficiency of growth at 26° C. compared to its wild-type (wt) parental virus, but its replication was neither temperature sensitive nor significantly cold-adapted. The cold-passaged mutant, however, was attenuated for adults.

Although satisfactorily attenuated and immunogenic for infants and children who had been previously infected with RSV (i.e., seropositive individuals), the cpRSV mutant retained a low level virulence for the upper respiratory tract of seronegative infants.

Similarly, Gharpure et al., (*J. Virol.* 3:414-421, 1969) reported the isolation of temperature sensitive RSV (tsRSV) mutants which also were promising vaccine candidates. One mutant, ts-1, was evaluated extensively in the laboratory and in volunteers. The mutant produced asymptomatic infection in adult volunteers and conferred resistance to challenge with wild-type virus 45 days after immunization. Again, while seropositive infants and children underwent asymptomatic infection, seronegative infants developed signs of rhinitis and other mild symptoms. Furthermore, instability of the ts phenotype was detected. Although virus exhibiting a partial or complete loss of temperature sensitivity represented a small proportion of virus recoverable from vaccinees, it was not associated with signs of disease other than mild rhinitis.

These and other studies revealed that certain cold-passaged and temperature sensitive RSV strains were underattenuated and caused mild symptoms of disease in some vaccinees, particularly seronegative infants, while others were overattenuated and failed to replicate sufficiently to elicit a protective immune response, (Wright et al., *Infect. Immun.*, 37:397-400, 1982). Moreover, genetic instability of candidate vaccine mutants has resulted in loss of their temperature sensitive phenotype, further hindering development of effective RSV vaccines. See generally, (Hodes et al., *Proc. Soc. Exp. Biol. Med.* 145:1158-1164, 1974; McIntosh et al., *Pediatr. Res.* 8:689-696, 1974; and Belshe et al., *J. Med. Virol.*, 3:101-110, 1978).

As an alternative to live-attenuated RSV vaccines, investigators have also tested subunit vaccine candidates using purified RSV envelope glycoproteins. The glycoproteins induced resistance to RS virus infection in the lungs of cotton rats, (Walsh et al., *J. Infect. Dis.* 155:1198-1204, 1987), but the antibodies had very weak neutralizing activity and immunization of rodents with purified subunit vaccine led to disease potentiation (Murphy et al., *Vaccine* 8:497-502, 1990).

Recombinant vaccinia virus vaccines which express the F or G envelope glycoprotein have also been explored. These recombinants express RSV glycoproteins which are indistinguishable from the authentic viral counterpart, and rodents infected intradermally with vaccinia-RSV F and G recombinants developed high levels of specific antibodies that neutralized viral infectivity. Indeed, infection of cotton rats with vaccinia-F recombinants stimulated almost complete resistance to replication of RSV in the lower respiratory tract and significant resistance in the upper tract. (Olmsted et al., *Proc. Natl. Acad. Sci. USA* 83:7462-7466, 1986). However, immunization of chimpanzees with vaccinia-F and -G recombinant provided almost no protection against RSV challenge in the upper respiratory tract (Collins et al., *Vaccine* 8:164-168, 1990) and inconsistent protection in the lower respiratory tract (Crowe et al., *Vaccine* 11: 1395-1404, 1993).

Despite these various efforts to develop an effective RSV vaccine, no licensed vaccine has yet been approved for RSV. The unfulfilled promises of prior approaches underscores a need for new strategies to develop RSV vaccines, and in particular methods for manipulating recombinant RSV to incorporate genetic changes that yield new phenotypic properties in viable, attenuated RSV recombinants. However, manipulation of the genomic RNA of RSV and other non-segmented negative-sense RNA viruses has heretofore proven difficult. Major obstacles in this regard include non-infectivity of naked genomic RNA of these viruses, poor viral growth in tissue culture, lengthy replication cycles, virion instability, a complex genome, and a refractory organization of gene products.

Recombinant DNA technology has made it possible to recover infectious non-segmented negative-stranded RNA viruses from cDNA, to genetically manipulate viral clones to construct novel vaccine candidates, and to rapidly evaluate their level of attenuation and phenotypic stability (for reviews, see Conzelmann, *J. Gen. Virol.* 77:381-89, 1996; Palese et al., *Proc. Natl. Acad. Sci. U.S.A.* 93:11354-58, 1996). In this context, recombinant rescue has been reported for infectious respiratory syncytial virus (RSV), parainfluenza virus (PIV), rabies virus (RaV), vesicular stomatitis virus (VSV), measles virus (MeV), rinderpest virus and Sendai virus (SeV) from cDNA-encoded antigenomic RNA in the presence of essential viral proteins (see, e.g., Garcin et al., *EMBO J.* 14:6087-6094, 1995; Lawson et al., *Proc. Natl. Acad. Sci. U.S.A.* 92:4477-81, 1995; Radecke et al., *EMBO J.* 14:5773-5784, 1995; Schnell et al., *EMBO J.* 13:4195-203, 1994; Whelan et al., *Proc. Natl. Acad. Sci. U.S.A.* 92:8388-92, 1995; Hoffman et al., *J Virol.* 71:4272-4277, 1997; Pecters et al., *J. Virol.* 73:5001-5009, 1999; Kato et al., *Genes to Cells* 1:569-579, 1996; Roberts et al., *Virology* 247(1), 1-6, 1998; Baron et al., *J Virol.* 71:1265-1271, 1997; International Publication No. WO 97/06270; U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Collins, et al., *Proc Nat. Acad. Sci. U.S.A.* 92:11563-11567, 1995; Bukreyev, et al., *J Virol* 70:663441, 1996, Juhasz et al., *J. Virol.* 71(8):5814-5819, 1997; Durbin et al., *Virology* 235:323-332, 1997; He et al. *Virology* 237:249-260, 1997; Baron et al. *J. Virol.* 71:1265-1271, 1997; Whitehead et al., *Virology* 247(2):232-9, 1998a; Buchholz et al. *J. Virol.* 73:251-9, 1999; Whitehead et al., *J. Virol.* 72(5):4467-4471, 1998b; Jin et al. *Virology* 251:206-214, 1998; and Whitehead et al., *J. Virol.* 73:(4)3438-3442, 1999, and Bukreyev, et al., *Proc Nat Acad Sci USA* 96:2367-72, 1999, each incorporated herein by reference in its entirety for all purposes).

Based on the foregoing developments, it is now possible to recover infectious RSV from cDNA and to design and implement various genetic manipulations to RSV clones to construct novel vaccine candidates. Thereafter, the level of attenuation and phenotypic stability, among other desired phenotypic characteristics, can be evaluated and adjusted. The challenge which thus remains is to develop a broad and diverse menu of genetic manipulations that can be employed, alone or in combination with other types of genetic manipulations, to construct infectious, attenuated RSV clones that are useful for broad vaccine use. In this context, an urgent need remains in the art for additional tools and methods that will allow engineering of safe and effective vaccines to alleviate the serious health problems attributable to RSV. Surprisingly, the present invention fulfills this need by providing additional tools for constructing infectious, attenuated RSV vaccine candidates.

SUMMARY OF THE INVENTION

The present invention provides recombinant respiratory syncytial viruses (RSVs) which are modified by shifting a relative gene order or spatial position of one or more genes or genome segments within a recombinant RSV genome or antigenome—to generate a recombinant vaccine virus that is infectious, attenuated and immunogenic in humans and other mammals. The recombinant RSVs of the invention typically comprise a major nucleocapsid (N) protein, a nucleocapsid phosphoprotein (P), a large polymerase protein (L), a RNA polymerase elongation factor, and a partial or complete recombinant RSV genome or antigenome having one or more positionally shifted RSV genes or genome segments within the recombinant genome or antigenome. In certain aspects of the invention, the recombinant RSV features one or more positionally shifted genes or genome segments that may be shifted to a more promoter-proximal or promoter-distal position by insertion, deletion, or rearrangement of one or more displacement polynucleotides within the partial or complete recombinant RSV genome or antigenome. Displacement polynucleotides may be inserted or rearranged into a non-coding region (NCR) of the recombinant genome or antigenome, or may be incorporated in the recombinant RSV genome or antigenome as a separate gene unit (GU).

In exemplary embodiments of the invention, isolated infectious recombinant RSV are constructed by addition, deletion, or rearrangement of one or more displacement polynucleotides that may be selected from one or more RSV gene(s) or genome segment(s) selected from RSV NS1, NS2, N, P, M, SH, M2(ORF1), M2(ORF2), L, F and G genes and genome segments and leader, trailer and intergenic regions of the RSV genome and segments thereof. In more detailed embodiments, polynucleotide inserts, and deleted or rearranged elements within the recombinant RSV genome or antigenome are selected, from one or more bovine RSV (BRSV) or human RSV (HRSV) gene(s) or genome segment(s) selected from RSV NS1, NS2, N, P, M, SH, M2(ORF1), M2(ORF2), L, F and G gene(s) or genome segment(s) and leader, trailer and intergenic regions of the RSV genome or segments thereof.

In certain aspects of the invention, displacement polynucleotides are deleted to form the recombinant RSV genome or antigenome. Deletion of a displacement polynucleotide in this manner causes a positional shift of one or more "shifted" RSV genes or genome segments within the recombinant genome or antigenome to a more promoter-proximal position relative to a position of the shifted gene(s) or genome segment(s) within a wild type RSV (e.g., HRSV A2 or BRSV kansas strain) genome or antigenome. Exemplary displacement polynucleotides that may be deleted in this manner to form the recombinant RSV genome or antigenome may be selected from one or more RSV NS1, NS2, SH, M2(ORF2), or G gene(s) or genome segment(s) thereof.

In more detailed embodiments of the invention, a displacement polynucleotide comprising a RSV NS1 gene is deleted to form the recombinant RSV genome or antigenome. Alternatively, a displacement polynucleotide comprising a RSV NS2 gene may be deleted to form the recombinant RSV genome or antigenome. Alternatively, a displacement polynucleotide comprising a RSV SH gene may be deleted to form the recombinant RSV genome or antigenome. Alternatively, a displacement polynucleotide comprising RSV M2(ORF2) can be deleted to form the recombinant RSV genome or antigenome. Alternatively, a displacement polynucleotide comprising a RSV G gene may be deleted to form the recombinant RSV genome or antigenome or antigenome.

In yet additional embodiments, multiple displacement polynucleotides comprising RSV genes or genome segments may be deleted. For example, RSV F and G genes may both be deleted to form the recombinant RSV genome or antigenome or antigenome. Alternatively, the RSV NS1 and NS2 genes may both be deleted to form the recombinant RSV genome or antigenome or antigenome. Alternatively, the RSV SH and NS2 genes may both be deleted to form the recombinant RSV genome or antigenome or antigenome. Alternatively, the RSV SH, NS1 and NS2 genes can all be deleted to form the recombinant RSV genome or antigenome or antigenome.

In different embodiments of the invention, isolated infectious recombinant RSV are provided wherein one or more displacement polynucleotides is/are added, substituted, or rearranged within the recombinant RSV genome or antigenome to cause a positional shift of one or more shifted RSV gene(s) or genome segment(s). Among these modifications, gene and genome segment insertions and rearrangements may introduce or rearrange the subject genes or genome segments to a more promoter-proximal or promoter-distal position relative to a respective position of each subject (inserted or rearranged) gene or genome segment within a corresponding (e.g., bovine or human) wild type RSV genome or antigenome. Displacement polynucleotides which may be added, substituted, or rearranged within the recombinant RSV genome or antigenome can be selected from one or more of the RSV NS1, NS2, SH, M2(ORF2), F, and/or G gene(s) or genome segment(s) thereof.

In more detailed embodiments, displacement polynucleotides are selected for insertion or rearrangement within the recombinant RSV genome or antigenome which comprises one or more RSV genes or genome segments that encoded one or more RSV glycoproteins or immunogenic domains or epitopes of RSV glycoproteins. In exemplary embodiments, these displacement polynucleotides are selected from genes or genome segments encoding RSV F, G, and/or SH glycoproteins or immunogenic domains or epitopes thereof. For example, one or more RSV glycoprotein gene(s) selected from F, G and SH may be added, substituted or rearranged within the recombinant RSV genome or antigenome to a position that is more promoter-proximal or promoter-distal compared to the wild type gene order position of the gene(s).

In exemplary embodiments, the RSV glycoprotein gene G is rearranged within the recombinant RSV genome or antigenome to a gene order position that is more promoter-proximal compared to the wild type gene order position of G. In more detailed aspects, the RSV glycoprotein gene G is shifted to gene order position 1 within said recombinant RSV genome or antigenome. In other exemplary embodiments, the RSV glycoprotein gene F is rearranged within the recombinant RSV genome or antigenome to a more promoter-proximal position, for example by shifting the F gene to gene order position 1 within the recombinant genome or antigenome. In yet additional exemplary embodiments, both RSV glycoprotein genes G and F are rearranged within the recombinant RSV genome or antigenome to gene order positions that are more promoter-proximal compared to their respective wild type gene order positions. In more detailed aspects, the RSV glycoprotein gene G is shifted to gene order position 1 and the RSV glycoprotein gene F is shifted to gene order position 2.

In yet additional constructs featuring glycoprotein gene shifts, recombinant RSV are produced having one or more RSV glycoprotein gene(s) selected from F, G and SH, or a genome segment thereof, added, substituted or rearranged within the recombinant RSV genome or antigenome, wherein one or more RSV NS1, NS2, SH, M2(ORF2), or G gene(s) or genome segment(s) thereof is/are deleted. Thus, a gene or genome segment of RSV F, G, or SH may be added, substituted or rearranged in a background wherein a displacement polynucleotide comprising a RSV NS1 gene is deleted to form the recombinant RSV genome or antigenome. Alternatively, a gene or genome segment of RSV F, G, or SH may be added, substituted or rearranged in a background wherein a displacement polynucleotide comprising a RSV NS2 gene is deleted to form the recombinant RSV genome or antigenome. Alternatively, a gene or genome segment of RSV F, G, or SH may be added, substituted or rearranged in a background wherein a displacement polynucleotide comprising a RSV SH gene is deleted to form the recombinant RSV genome or antigenome.

In one example below, the RSV glycoprotein gene G is rearranged within a recombinant RSV genome or antigenome having an SH gene deletion to a gene order position that is more promoter-proximal compared to the wild type gene order position of G. In more detailed aspects, the RSV glycoprotein gene G is shifted to gene order position 1 within the recombinant RSV genome or antigenome, as exemplified by the recombinant vaccine candidate G1/ΔSH. In another example, the RSV glycoprotein gene F is rearranged within a recombinant RSV genome or antigenome having an SH gene deletion to a more promoter-proximal proximal position. In more detailed aspects, the F gene is shifted to gene order position 1, as exemplified by the recombinant F1ΔSH. In yet another example below, both RSV glycoprotein genes G and F are rearranged within a ΔSH recombinant RSV genome or antigenome to gene order positions that are more promoter-proximal compared to the wild type gene order positions of G and F. In more detailed aspects, the RSV glycoprotein gene G is shifted to gene order position 1 and the RSV glycoprotein gene F is shifted to gene order position 1 within the recombinant RSV genome or antigenome, as exemplified by the recombinant G1F2/ΔSH.

Yet additional examples of gene position-shifted RSV are provided featuring shifts of glycoprotein gene(s) selected from F, G and SH, which are produced within a recombinant RSV genome or antigenome having multiple genes or genome segments selected from RSV NS1, NS2, SH, M2(ORF2), and G gene(s) or genome segment(s) deleted. In one example, the RSV SH and NS2 genes are both deleted to form the recombinant RSV genome or antigenome or antigenome, and one or both RSV glycoprotein genes G and F are rearranged within the recombinant RSV genome to more promoter-proximal gene order positions. In more detailed aspects, G is shifted to gene order position 1 and F is shifted to gene order position 2, as exemplified by the recombinant G1F2/ΔNS2ΔSH. In another example, all of the RSV SH, NS1 and NS2 genes are deleted to form the recombinant RSV genome or antigenome or antigenome, and one or both RSV glycoprotein genes G and F are rearranged within the recombinant RSV genome or antigenome to more promoter-proximal positions, as exemplified by the recombinant vaccine candidate G1F2/ΔNS2ΔNS2ΔSH.

In yet additional aspects of the invention, gene position-shifted RSV are combined with or incorporated within human-bovine chimeric RSV. Within these aspects, the recombinant genome or antigenome comprises a partial or complete human RSV (HRSV) or bovine RSV (BRSV) background genome or antigenome combined with one or more heterologous gene(s) or genome segment(s) from a different RSV to for a human-bovine chimeric RSV genome or antigenome. The heterologous gene or genome segment of the different, HRSV or BRSV may be added or substituted at a position that is more promoter-proximal or promoter-distal compared to a wild type gene order position of a counterpart gene or genome segment within the partial or complete HRSV or BRSV background genome or antigenome. In one such example provided herein, both human RSV glycoprotein genes G and F are substituted at gene order positions 1 and 2, respectively, to replace counterpart G and F glycoprotein genes deleted at wild type positions 7 and 8, respectively in a partial bovine RSV background genome or antigenome, as exemplified by the recombinant virus rBRSV/A2-G1F2. In other embodiments, one or more human RSV envelope-associated genes selected from F, G, SH, and M is/are added or substituted within a partial or complete bovine RSV background genome or antigenome. In more detailed aspects, one or more human RSV envelope-associated genes selected from F, G, SH, and M is/are added or substituted within a partial bovine RSV background genome or antigenome in which one or more envelope-associated genes selected from F, G, SH, and M is/are deleted. In one example described below, human RSV envelope-associated genes F, G, and M are added within a partial bovine RSV background genome or antigenome in which all of the envelope-associated genes F, G, SH, and M are deleted, as exemplified by the recombinant virus rBRSV/A2-MGF.

In another alternate embodiment of the invention, isolated infectious recombinant RSV are provided in which the RSV M2(ORF1) is shifted to a more promoter-proximal position within the recombinant RSV genome or antigenome. The result of this gene shift is to upregulate transcription of the recombinant virus.

In additional aspects of the invention, attenuated, gene position-shifted RSV are produced in which the recombinant genome or antigenome is further modified by introducing one or more attenuating mutations specifying an attenuating phenotype in the resultant virus or subviral particle. These attenuating mutations may be generated de novo and tested for attenuating effects according to a rational design mutagenesis strategy. Alternatively, the attenuating mutations may be identified in existing biologically derived mutant RSV and thereafter incorporated into a gene position-shifted RSV of the invention.

In combination with the gene positional changes introduced in recombinant RSV of the invention, it is often desirable to adjust the attenuation phenotype by introducing additional mutations that increase or decrease attenuation of the chimeric virus. Thus, candidate vaccine strains can be further attenuated by incorporation of at least one, and preferably two or more different attenuating mutations, for example mutations identified from a panel of known, biologically derived mutant RSV strains. Preferred human mutant RSV strains are cold passaged (cp) and/or temperature sensitive (ts) mutants, for example the mutants designated "cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579)" (each deposited under the terms of the Budapest Treaty with the American Type Culture Collection (ATCC) of 10801 University Boulevard, Manassas, Va. 20110-2209, U.S.A., and granted the above identified accession numbers). From this exemplary panel of biologically derived mutants, a large "menu" of attenuating mutations are provided which can each be combined with any other mutation(s) within the panel for calibrating the level of attenuation in the recombinant, human-bovine chimeric RSV for vaccine use. Additional mutations may be derived from RSV having non-ts and non-cp attenuating mutations as identified, e.g., in small plaque (sp), cold-adapted (ca) or host-range restricted (hr) mutant strains. The mutations may be incorporated in either a human or bovine antigenomic sequence, and attenuating mutations identified in a human, bovine or other RSV mutant may be transferred to the heterologous RSV recipient (e.g., bovine or human RSV, respectively) by mapping the mutation to the corresponding, homologous site in the recipient genome and mutating the native sequence in the recipient to the mutant genotype (either by an identical or conservative mutation), as described in U.S. Provisional Patent Application No. 60/129,006, filed by Murphy et al. on Apr. 13, 1999, incorporated herein by reference.

Thus, in more detailed embodiments of the invention, gene position-shifted RSV are provided wherein the recombinant genome or antigenome incorporates at least one and up to a full complement of attenuating mutations present within a panel of mutant human RSV strains, said panel comprising cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In certain embodiments, the recombinant genome or antigenome incorporates attenuating mutations adopted from different mutant RSV strains.

Gene position-shifted RSV designed and selected for vaccine use often have at least two and sometimes three or more attenuating mutations to achieve a satisfactory level of attenuation for broad clinical use. In one embodiment, at least one attenuating mutation occurs in the RSV polymerase gene L (either in the donor or recipient gene) and involves one or more nucleotide substitution(s) specifying an amino acid change in the polymerase protein specifying an attenuation phenotype which may or may not involve a temperature-sensitive (ts) phenotype. Gene position-shifted RSV of the invention may incorporate an attenuating mutation in any additional RSV gene besides L, e.g., in the M2 gene. However, preferred human-bovine chimeric RSV in this context incorporate one or more nucleotide substitutions in the large polymerase gene L resulting in an amino acid change at amino acid Asn43, Cys319, Phe 521, Gln831, Met1169, Tyr1321 and/or His 1690 in the RSV polymerase gene L, as exemplified by the changes, Ile for Asn43, Leu for Phe521, Leu for Gln831, Val for Met1169, and Asn for Tyr1321. Other alternative amino acid changes, particularly conservative changes with respect to identified mutant residues, at these positions can of course be made to yield a similar effect as the identified, mutant substitution. Additional desired mutations for incorporation into human-bovine chimeric RSV of the invention include attenuating mutations specifying an amino acid substitution at Val267 in the RSV N gene, Glu218 and/or Thr523 in the RSV F gene, and a nucleotide substitution in the gene-start sequence of gene M2. Any combination of one or more attenuating mutations identified herein, up to and including a full complement of these mutations, may be incorporated in human-bovine chimeric RSV to yield a suitably attenuated recombinant virus for use in selected populations or broad populations of vaccine recipients.

In other more detailed embodiments of the invention, gene position-shifted RSV are provided wherein the recombinant genome or antigenome incorporates at least one and up to a full complement of attenuating mutations specifying an amino acid substitution at Val267 in the RSV N gene, Glu218 and/or Thr523 in the RSV F gene, Asn43, Cys319, Phe 521, Gln831, Met1169, Tyr1321 and/or His 1690 in the RSV polymerase gene L, and a nucleotide substitution in the gene-start sequence of gene M2. In certain aspects, the recombinant genome or antigenome incorporates at least two, commonly three, four or five, and sometimes a full complement comprising all of these attenuating mutations. Often, at least one attenuating mutation is stabilized by multiple nucleotide changes in a codon specifying the mutation.

Attenuating mutations for incorporation in human-bovine chimeric RSV of the invention may be selected in coding portions of a donor or recipient RSV gene or in non-coding regions such as a cis-regulatory sequence. Exemplary non-coding mutations include single or multiple base changes in a gene start sequence, as exemplified by a single or multiple base substitution in the M2 gene start sequence at nucleotide 7605 (nucleotide 7606 in recombinant sequence).

Infectious RSV according to the invention can incorporate heterologous, coding or non-coding nucleotide sequences from any heterologous RSV or RSV-like virus, e.g., human, bovine, murine pneumonia virus of mice), or avian (turkey rhinotracheitis virus) pneumovirus, or from another enveloped virus, e.g., parainfluenza virus (PIV). Exemplary heterologous sequences include RSV sequences from one human RSV strain combined with sequences from a different human RSV strain, or RSV sequences from a human RSV strain combined with sequences from a bovine RSV strain. Gene position-shifted RSV of the invention may incorporate sequences from two or more wild-type or mutant RSV strains, for example mutant stains selected from cpts RSV 248, cpts 248/404, cpts 248/955, cpts RSV 530, cpts 530/1009, or cpts 530/1030. Alternatively, chimeric RSV may incorporate sequences from two or more, wild-type or mutant human RSV subgroups, for example a combination of human RSV subgroup A and subgroup B sequences. In yet additional aspects, one or more human RSV coding or non-coding polynucleotides are substituted with a counterpart sequence from a heterologous RSV or non-RSV virus, alone or in combination with one or more selected attenuating mutations, e.g., cp and/or ts mutations, to yield novel attenuated vaccine strains.

Mutations incorporated within gene position-shifted RSV cDNAs, vectors and viral particles of the invention can be introduced individually or in combination into a full-length RSV cDNA, and the phenotypes of rescued virus containing the introduced mutations can be readily determined. In exemplary embodiments, amino acid changes displayed by attenuated, biologically-derived viruses versus a wild-type RSV, for example changes exhibited by cpRSV or tsRSV, are incorporated in combination within a gene position-shifted RSV to yield a desired level of attenuation.

In additional aspects of the invention, gene position-shifted RSV can be readily designed as "vectors" to incorporate antigenic determinants from different pathogens, including more than one RSV strain or group (e.g., both human RSV A and RSV B subgroups), human parainfluenza virus (HPIV) including HPIV3, HPIV2 and HPIV1, measles virus and other pathogens (see, e.g., U.S. Provisional Patent Application Ser. No. 60/170,195; U.S. patent application Ser. No. 09/458,813; and U.S. patent application Ser. No. 09/459,062, each incorporated herein by reference). Within various embodiments, the recombinant genome or antigenome comprises a partial or complete RSV "vector genome or antigenome" combined with one or more heterologous genes or genome segments encoding one or more antigenic determinants of one or more heterologous pathogens. The heterologous pathogen may be a heterologous RSV (i.e., a RSV of a different strain or subgroup), and the heterologous gene or genome segment may encode a RSV NS1, NS2, N, P, M, SH, M2(ORF1), M2(ORF2), L, F or G protein or fragment (e.g., a immunogenic domain or epitope) thereof. For example, the vector genome or antigenome may be a partial or complete RSV A genome or antigenome and the heterologous gene(s) or genome segment(s) may encode antigenic determinant(s) of a RSV B subgroup virus.

In alternative embodiments, the gene position-shifted RSV vector genome or antigenome is a partial or complete BRSV genome or antigenome and the heterologous gene(s) or genome segment(s) encoding the antigenic determinant(s) is/are of one or more HRSV(s). For example, the partial or complete BRSV genome or antigenome may incorporate one or more gene(s) or genome segment(s) encoding one or more HRSV glycoprotein genes selected from F, G and SH, or one or more genome segment(s) encoding cytoplasmic domain, transmembrane domain, ectodomain or immunogenic epitope portion(s) of F, G, and/or SH of HRSV.

As noted above, gene position-shifted RSV designed as vectors for carrying heterologous antigenic determinants may incorporate one or more antigenic determinants of a non-RSV pathogen, such as a human parainfluenza virus (HPIV). In one exemplary embodiment, one or more HPIV1, HPIV2, or HPIV3 gene(s) or genome segment(s) encoding one or more HN and/or F glycoprotein(s) or antigenic domain(s), fragment(s) or epitope(s) thereof is/are added to or incorporated within the partial or complete HRSV vector genome or antigenome. In more detailed embodiments, a transcription unit comprising an open reading frame (ORF) of an HPIV1, BPIV2, or HPIV3 HN or F gene is added to or incorporated within the recombinant vector genome or antigenome.

In yet additional alternate embodiments, the vector genome or antigenome comprises a partial or complete HRSV or BRSV genome or antigenome and the heterologous pathogen is selected from measles virus, subgroup A and subgroup B respiratory syncytial viruses, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses. Based on this exemplary list of candidate pathogens, the selected heterologous antigenic determinant(s) may be selected from measles virus HA and F proteins, subgroup A or subgroup B respiratory syncytial virus F, G, SH and M2 proteins, mumps virus HN and F proteins, human papilloma virus L1 protein, type 1 or type 2 human immunodeficiency virus gp160 protein, herpes simplex virus and cytomegalovirus gB, gC, gD, gE, gG, gH, gI, gJ, gK, gL, and gM proteins, rabies virus G protein, Epstein Barr Virus gp350 protein; filovirus G protein, bunyavirus G protein, Flavivirus E and NS1 proteins, and alphavirus E protein, and antigenic domains, fragments and epitopes thereof. In one embodiment, the heterologous pathogen is measles virus and the heterologous antigenic determinant(s) is/are selected from the measles virus HA and F proteins and antigenic domains, fragments and epitopes thereof. To achieve such a chimeric construct, a transcription unit comprising an open reading frame (ORF) of a measles virus HA gene may be added to or incorporated within a HRSV vector genome or antigenome.

The present invention thus provides gene position-shifted RSV clones, polynucleotide expression constructs (also referred to as vectors) and particles which can incorporate multiple, phenotype-specific mutations introduced in selected combinations into the gene position-shifted RSV genome or antigenome to produce an attenuated, infectious virus or subviral particle. This process coupled with routine phenotypic evaluation provides gene position-shifted RSV having such desired characteristics as attenuation, temperature sensitivity, altered immunogenicity, cold-adaptation, small plaque size, host range restriction, etc. Mutations thus identified are compiled into a "menu" and introduced in various combinations to calibrate a vaccine virus to a selected level of attenuation, immunogenicity and stability.

In yet additional aspects of the invention, gene position-shifted RSV, with or without attenuating mutations, are constructed to have a nucleotide modification to yield a desired phenotypic, structural, or functional change. Typically, the selected nucleotide modification will specify a phenotypic change, for example a change in growth characteristics, attenuation, temperature-sensitivity, cold-adaptation, plaque size, host range restriction, or immunogenicity. Structural changes in this context include introduction or ablation of restriction sites into RSV encoding cDNAs for ease of manipulation and identification.

In certain embodiments, nucleotide changes within gene position-shifted RSV include modification of a viral gene by deletion of the gene or ablation of its expression. Target genes for mutation in this context include the attachment (G) protein, fusion (F) protein, small hydrophobic (SH), RNA binding protein (N), phosphoprotein (P), the large polymerase protein (L), the transcription elongation factor (M2 ORF1), the RNA regulatory factor M2 ORF2, the matrix (M) protein, and two nonstructural proteins, NS1 and NS2. Each of these proteins can be selectively deleted, substituted or rearranged, in whole or in part, alone or in combination with other desired modifications, to achieve novel chimeric RSV recombinants.

In one aspect of the invention, an SH, NS1, NS2, G or M2-2 gene is modified in the gene position-shifted RSV. For example, each of these genes may be deleted or its expression ablated (e.g., by introduction of a stop codon) to alter the phenotype of the resultant recombinant RSV clone to improve growth, attenuation, immunogenicity or other desired phenotypic characteristics. For example, deletion of the SH gene in the recombinant genome or antigenome will yield a RSV having novel phenotypic characteristics such as enhanced growth in vitro and/or attenuation in vivo. In a related aspect, an SH gene deletion, or deletion of another selected non-essential gene or genome segment such as a NS1, NS2, G or M2-2 gene deletion is constructed in a gene position-shifted RSV, alone or in combination with one or more different mutations specifying an attenuated phenotype, e.g., a point mutation adopted directly (or in modified form, e.g., by introducing multiple nucleotide changes in a codon specifying the mutation) from a biologically derived attenuated RSV mutant. For example, the SH, NS1, NS2, G or M2-2 gene may be deleted in combination with one or more cp and/or ts mutations adopted from cpts248/404, cpts530/1009, cpts530/1030 or another selected mutant RSV strain, to yield a gene position-shifted RSV having increased yield of virus, enhanced attenuation, improved immunogenicity and genetic resistance to reversion from an attenuated phenotype due to the combined effects of the different mutations.

Alternative nucleotide modifications can include a deletion, insertion, addition or rearrangement of a cis-acting regulatory sequence for a selected gene in the gene position-shifted RSV. In one example, a cis-acting regulatory sequence of one RSV gene is changed to correspond to a heterologous regulatory sequence, which may be a counterpart cis-acting regulatory sequence of the same gene in a different RSV or a cis-acting regulatory sequence of a different RSV gene. For example, a gene end signal may be modified by conversion or substitution to a gene end signal of a different gene in the same RSV strain. In other embodiments, the nucleotide modification may comprise an insertion, deletion, substitution, or rearrangement of a translational start site within the chimeric genome or antigenome, e.g., to ablate an alternative translational start site for a selected form of a protein. In one example, the translational start site for a secreted form of the RSV G protein is ablated to modify expression of this form of the G protein and thereby produce desired in vivo effects.

In addition, a variety of other genetic alterations can be produced in a gene position-shifted RSV genome or antigenome, alone or together with one or more attenuating mutations adopted from a biologically derived mutant RSV. For example, genes or genome segments from non-RSV sources may be inserted in whole or in part. Nontranslated gene sequences can be removed, e.g., to increase capacity for inserting foreign sequences. In yet additional aspects, polynucleotide molecules or vectors encoding the gene position-shifted RSV genome or antigenome can be modified to encode non-RSV sequences, e.g., a cytokine, a T-helper epitope, a restriction site marker, or a protein of a microbial pathogen (e.g., virus, bacterium or fungus) capable of eliciting a protective immune response in an intended host. Different or additional modifications in the gene position-shifted RSV antigenome can be made to facilitate manipulations, such as the insertion of unique restriction sites in various intergenic regions (e.g., a unique StuI site between the G and F genes) or elsewhere.

All of the foregoing modifications within the gene position-shifted RSV genome or antigenome, including nucleotide insertions, rearrangements, deletions or substitutions yielding point mutations, site-specific nucleotide changes, and changes involving entire genes or genome segments, may be made to either a partial or complete RSV genome or antigenome, or within a heterologous donor gene or genome segment or recipient, background genome or antigenome in a chimeric RSV. In each case, these alterations will preferably specify one or more phenotypic change(s) in the resulting recombinant RSV, such as a phenotypic change that results in attenuation, temperature-sensitivity, cold-adaptation, small plaque size, host range restriction, alteration in gene expression, or a change in an immunogenic epitope.

In another aspect of the invention, compositions (e.g., isolated polynucleotides and vectors incorporating an RSV-encoding cDNA) and methods are provided for producing an isolated infectious gene position-shifted RSV. Using these compositions and methods, infectious gene position-shifted RSV particles or subviral particles are generated from a recombinant RSV genome or antigenome coexpressed with a nucleocapsid (N) protein, a nucleocapsid phosphoprotein (P), a large (L) polymerase protein, and an RNA polymerase elongation factor. In related aspects of the invention, compositions and methods are provided for introducing the aforementioned structural and phenotypic changes into a recombinant gene position-shifted RSV to yield infectious, attenuated vaccine viruses.

In one embodiment, an expression vector is provided which comprises an isolated polynucleotide molecule encoding a gene position-shifted RSV genome or antigenome. Also provided is the same or different expression vector comprising one or more isolated polynucleotide molecules encoding N, P, L and RNA polymerase elongation factor proteins. These proteins also can be expressed directly from the genome or antigenome cDNA. The vector(s) is/are preferably expressed or coexpressed in a cell or cell-free lysate, thereby producing an infectious gene position-shifted RSV particle or subviral particle.

The RSV genome or antigenome and the N, P, L and RNA polymerase elongation factor (preferably the product of the M2(ORF1) of RSV) proteins can be coexpressed by the same or different expression vectors. In some instances the N, P, L and RNA polymerase elongation factor proteins are each encoded on different expression vectors. The polynucleotide molecule encoding the gene position-shifted RSV genome or antigenome is operably joined to these control sequences to allow production of infectious virus or viral particles therefrom. In alternative aspects of the invention, the gene position-shifted RSV genome or antigenome can include sequences from multiple human RSV strains or subgroups (A and B), as well as other non-human (e.g., murine) RSV sequences. In other alternate aspects, the gene position-shifted RSV genome or antigenome can incorporate non-RSV sequences, for example a polynucleotide containing sequences from human and bovine RSV operably joined with a nucleotide or polynucleotide encoding a point mutation, protein, protein domain or immunogenic epitope of PIV or another negative stranded RNA virus.

The above methods and compositions for producing gene position-shifted RSV yield infectious viral or subviral particles, or derivatives thereof. An infectious virus is comparable to the authentic RSV virus particle and is infectious as is. It can directly infect fresh cells. An infectious subviral particle typically is a subcomponent of the virus particle which can initiate an infection under appropriate conditions. For example, a nucleocapsid containing the genomic or antigenomic RNA and the N, P, L and M2(ORF1) proteins is an example of a subviral particle which can initiate an infection if introduced into the cytoplasm of cells. Subviral particles provided within the invention include viral particles which lack one or more protein(s), protein segment(s), or other viral component(s) not essential for infectivity.

In other embodiments the invention provides a cell or cell-free lysate containing an expression vector which comprises an isolated polynucleotide molecule encoding a gene position-shifted RSV genome or antigenome as described above, and an expression vector (the same or different vector) which comprises one or more isolated polynucleotide molecules encoding the N, P, L and RNA polymerase elongation factor proteins of RSV. One or more of these proteins also can be expressed from the genome or antigenome cDNA. Upon expression the genome or antigenome and N, P, L, and RNA polymerase elongation factor proteins combine to produce an infectious gene position-shifted RSV viral or subviral particle.

Attenuated gene position-shifted RSV of the invention is capable of eliciting a protective immune response in an infected human host, yet is sufficiently attenuated so as to not cause unacceptable symptoms of severe respiratory disease in the immunized host. The attenuated virus or subviral particle may be present in a cell culture supernatant, isolated from the culture, or partially or completely purified. The virus may also be lyophilized, and can be combined with a variety of other components for storage or delivery to a host, as desired.

The invention further provides novel vaccines comprising a physiologically acceptable carrier and/or adjuvant and an isolated attenuated gene position-shifted RSV. In one embodiment, the vaccine is comprised of a gene position-shifted RSV having at least one, and preferably two or more attenuating mutations or other nucleotide modifications as described above. The vaccine can be formulated in a dose of $10^3$ to $10^6$ PFU of attenuated virus. The vaccine may comprise attenuated gene position-shifted RSV that elicits an immune response against a single RSV strain or antigenic subgroup, e.g. A or B, or against multiple RSV strains or subgroups. In this regard, gene position-shifted RSV of the invention can individually elicit a monospecific immune response or a polyspecific immune response against multiple RSV strains or subgroups. Gene position-shifted RSV can be combined in vaccine formulations with other RSVs having different immunogenic characteristics for more effective protection against one or multiple RSV strains or subgroups.

In related aspects, the invention provides a method for stimulating the immune system of an individual to elicit an immune response against one or more strains or subgroups of RSV in a mammalian subject. The method comprises administering a formulation of an immunologically sufficient amount of an attenuated, gene position-shifted RSV in a physiologically acceptable carrier and/or adjuvant. In one embodiment, the immunogenic composition is a vaccine comprised of gene position-shifted RSV having at least one, and preferably two or more attenuating mutations or other nucleotide modifications specifying a desired phenotype as described above. The vaccine can be formulated in a dose of $10^3$ to $10^6$ PFU of attenuated virus. The vaccine may comprise attenuated gene position-shifted RSV virus that elicits an immune response against a single RSV strain or antigenic subgroup, e.g. A or B, or against multiple RSV strains or subgroups. In this context, the gene position-shifted RSV can elicit a monospecific immune response or a polyspecific immune response against multiple RSV strains or subgroups. Alternatively, gene position-shifted RSV having different immunogenic characteristics can be combined in a vaccine mixture or administered separately in a coordinated treatment protocol to elicit more effective protection against one RSV strain, or against multiple RSV strains or subgroups. Preferably the immunogenic composition is administered to the upper respiratory tract, e.g., by spray, droplet or aerosol. Often, the composition will be administered to an individual seronegative for antibodies to RSV or possessing transplacentally acquired maternal antibodies to RSV.

Figure 1:
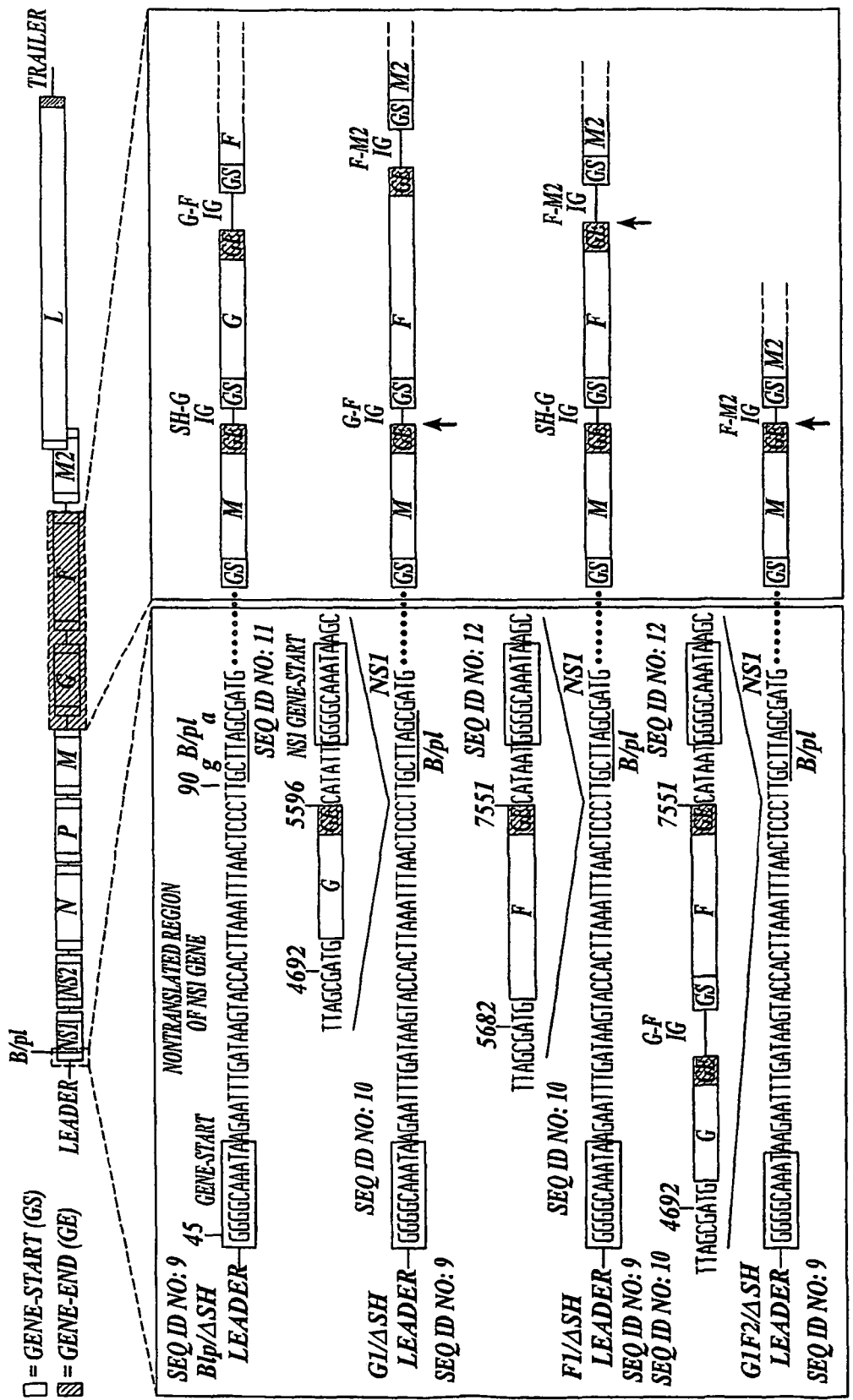
FIG. 1. Shift of the G gene, or the F gene, or the G and F genes together, to a promoter-proximal position within the RSV genome. The diagram at the top illustrates the RSV genome designated Blp/ΔSH, in which the SH gene has been deleted as described previously (Whitehead et al., J. Virol. 73:3438-3442, 1999; incorporated herein by reference) and a BlpI restriction enzyme site has been added to the upstream noncoding region of the promoter-proximal NS1 gene. The gene-end (GE) signal of the M gene has an asterisk to indicate that it contains a single nucleotide change incorporated during deletion of the SH gene that makes it identical to the naturally-occurring SH GE signal, as described previously (Whitehead et al., J. Virol. 73:3438-3442, 1999; incorporated herein by reference). The two boxes underneath the diagram show details of the structure of genome Blp/ΔSH as well as modifications that were made to the promoter-proximal end (left hand box) and M-G-F-M2 region (right hand box) of the ΔSH/Blp genome to create genomes G1/ΔSH, F1/ΔSH and G1F2/ΔSH. All manipulations were performed with a cloned cDNA of RSV antigenomic RNA (Collins et al., Proc. Natl. Acad. Sci. USA 92:11563-11567, 1995; Collins et al., Virology 259:251-255, 1999; and Whitehead et al., J. Virol. 73:3438-3442, 1999; incorporated herein by reference), and nucleotide positions are numbered according to the complete antigenomic sequence of wild type recombinant RSV (containing the SH gene) (Collins et al., Proc. Natl. Acad. Sci. USA 92:11563-11567, 1995; Murphy et al., U.S. Pat. No. 5,993,824; each incorporated herein by reference). Note that "upstream" and "downstream" refer to the promoter-proximal and promoter-distal directions, respectively (the promoter is at the 3' leader end of negative-sense genomic RNA, which is at the left hand end as drawn in FIG. 1).

Genome Blp/ΔSH: nucleotides 92 and 97 of the previously-described SH-deletion mutant of RSV (Whitehead et al., J. Virol. 73:3438-3442, 1999; incorporated herein by reference) were changed from G and A (indicated in the top diagram in the left hand box with small case letters), respectively, to C and C (bold capital letters), thereby creating a BlpI site (underlined) one nucleotide in front of the ATG translational start codon (italicized, bold) of the NS1 open reading frame (ORF). The M-G-F region of the Blp/ΔSH genome (right hand box) illustrates the SH deletion (the SH gene normally lies between the M and G genes).

Genome G1/ΔSH: This genome contains the G gene in the promoter-proximal position, inserted into the BlpI site (left hand box). The G cDNA insert was constructed as follows: the complete G ORF and downstream G noncoding sequence and GE signal (nucleotides 4692 to 5596) were engineered to be followed by a 6-nucleotide IG sequence (representing the first 6 nucleotides of the naturally-occurring G-F IG sequence, CATATT (SEQ ID NO: 1) followed by a copy of the 10-nucleotide GS signal of the NS1 gene (boxed). This cloned sequence was flanked by BlpI sites, and was cloned into the BlpI site of genome Blp/ΔSH. This placed the G ORF, under the control of RSV GS and GE signals, into the promoter-proximal position. In the same genome, the G gene was deleted from its downstream position between the M and F genes (the point of deletion is indicated with a large arrow), and the M and F genes were now separated only by the G-F IG sequence.

Genome F1/ΔSH: This genome contains the F gene in the promoter-proximal position, inserted into the BlpI site. The F cDNA insert was constructed as follows: the complete F ORF and downstream noncoding sequence and GE signal (nucleotides 5662 to 7551) were engineered to be followed by a 6-nucleotide IG sequence (representing the first 6 nucleotides of the naturally-occurring F-M2 IG sequence, CACAAT (SEQ ID NO: 2) followed by the 10-nucleotide GS signal of the NS1 gene. This cloned sequence was flanked by BlpI sites and was cloned into the BlpI site of genome Blp/ΔSH. This placed the F ORF, under the control of RSV GS and GE signals, into the promoter-proximal position. In the same genome, the F gene was deleted from its downstream position between the G and M2 genes (the point of deletion is indicated with a large arrow), and these two genes were now separated only by the F-M2 IG sequence.

Genome G1F2/ΔSH: This genome contains the G and F genes in the first and second promoter-proximal locations, respectively, inserted as a single cDNA into the BlpI site. This G-F cDNA insert was constructed to contain (in upstream to downstream order): the complete G ORF, its downstream noncoding and GE signal, the G-F IG sequence, the complete F gene, 6 nucleotides from the F-M2 IG sequence (CACAAT) (SEQ ID NO: 2), and the NS1 GS signal. This cDNA was flanked by BlpI sites and was cloned into the BlpI site of genome Blp/ΔSH. This placed the G and F genes into positions 1 and 2, respectively, relative to the promoter. In the same genome, the G and F genes were deleted from their downstream positions between the M and M2 genes (the point of deletion is indicated with a large arrow), and M and M2 genes were now separated only by the F-M2 IG sequence.

Figure 2:
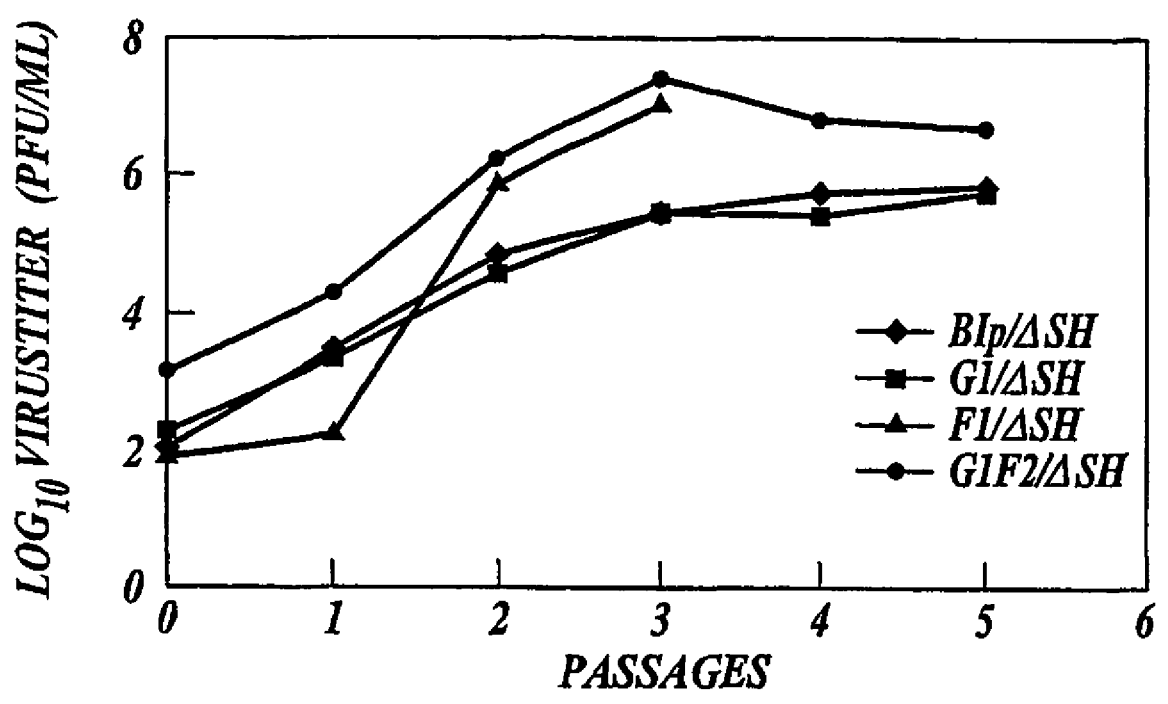

FIG. 2. Production of infectious recombinant virus during the transfection and initial passages in vitro. HEp-2 cells were transfected with the indicated individual antigenomic plasmid and the N, P, L and M2-1 support plasmids as described (Murphy et al., U.S. Pat. No. 5,993,824). The medium supernatants were harvested 3 days later and subjected to serial undiluted passage in HEp-2 cells, with the medium supernatant harvested at 3- to 7-day intervals. Samples of each harvest were taken, flash-frozen, and analyzed later in parallel by plaque assay. The viruses were given the same designations as their respective cDNAs, i.e. Blp/ΔSH, G1/ΔSH etc. Data are shown for Blp/ΔSH, G1/ΔSH, F1/ΔSH and G1F2/ΔSH. Transfection was at 32° C. and subsequent passages were at 37° C.

FIG. 3A Replication in vitro of recombinant wt RSV (containing the SH gene), and the ΔSH (not containing a BlpI site), Blp/ΔSH, G1/ΔSH and G1F2/ΔSH mutant viruses following infection at an input multiplicity of infection (MOI) of 0.1. Replicate cultures of Vero (top panel) or HEp-2 cells (lower panel) were infected and incubated at 37° C. At the indicated time points, duplicate monolayers were harvested for each virus and the medium supernatants were flash-frozen. These were analyzed later in parallel by plaque assay.

FIG. 3B depicts single-step growth of the Blp/SH, G1/SH, F1/SH and G1F2/SH viruses following infection of Hep-2 (top) and Vero (bottom) cell monolayers at an input multiplicity of infection of 3.0. Replicate cell monolayers were infected and incubated at 37° C., and at the indicated time points duplicate monolayers were harvested and the medium supernatants were flash-frozen.

FIG. 4. Western blot analysis of the expression of the G protein by Blp/ΔSH, G1/ΔSH and G1F2/ΔSH viruses in Vero cells. The cells from each time point in the top panel of FIG. 3A were harvested and the total protein was analyzed by gel electrophoresis and Western blotting. The blots were developed by incubation with a rabbit antiserum specific to peptide of the G protein. Bound antibodies were then visualized by chemiluminescence. The G protein migrates as two forms: the 90 kDa mature form and a 50 kDa incompletely-glycosylated form.

FIG. 5. Structures of attenuated RSV's in which the G and F genes have been shifted to positions 1 and 2. Panel A: Structure of recombinant RSV G1F2/ΔNS2ΔSH, in which the SH and NS2 genes were deleted as described (Teng and Collins, *J. Virol.* 73:466-473, 1999; Whitehead et al., *J. Virol.* 73:3438-3442, 1999; incorporated herein by reference), and the G and F genes were moved into positions 1 and 2, respectively, as described above in FIG. 1. Panel B: Structure of recombinant RSV G1F2/ΔNS1ΔNS2ΔSH, in which the SH, NS1 and NS2 genes were deleted and the G and F genes were moved into positions 1 and 2, respectively.

FIG. 6 details construction of a chimeric rBRSV/HRSV genome in which the BRSV G and F genes have been deleted and the G and F genes of HRSV have been placed in a promoter-proximal position. BRSV genes are shaded; HRSV genes are clear. Nucleotide sequence position numbers are relative to the complete rBRSV antigenome (Buchholz et al., *J. Virol.* 73:251-259, 1999; Buchholz et al., *J. Virol.* 74:1187-1199, 2000; GenBank accession number AF092942 or complete rHRSV antigenome in Collins et al., *Proc. Natl. Acad. Sci. USA* 92:11563-11567, 1995; each incorporated herein by reference); sequence position numbers that refer to the HRSV sequence are underlined. FIG. 6, panel A details structure of rBRSV containing NotI, SalI and XhoI sites that were added in previous work (Buchholz et al., J. Virol. 73:251-259, 1999; Buchholz et al., *J. Virol.* 74:1187-1199, 2000). FIG. 6, panel B depicts modifications to rBRSV to create rBRSV/A2-G1F2. The BRSV G and F genes were deleted by digestion with SalI and XhoI and religation of the resulting compatible cohesive ends. The region of the genome of HRSV from nucleotides 4692 to 7557, containing the G and F genes, was amplified by PCR using primers that contained desired changes to be incorporated into each end of the cDNA. The amplified PCR product contained (in upstream to downstream order): a NotI site, a BlpI site, the complete HRSV G ORF, its downstream noncoding and GE signal, the HRSV G-F IG sequence, the complete HRSV F gene, 6 nucleotides from the HRSV F-M2 IG sequence (CACAAT), the NS1 GS signal, a BlpI site and a NotI site. This cDNA was cloned into the unique Notl site at position 67 of rBRSV. FIG. 6, panel C illustrates structure of the genomic RNA of rBRSV/A2-G1 F2.

FIG. 7 depicts multicycle growth of RBRSV, rHRSV(rA2), rBRSV/A2, and rBRSV/A2-G1 F2 in HEp-2 human (left panel) and MDBK bovine (right panel) cells. Duplicate cell monolayers were infected with the indicated virus at an MOI of 0.1 and incubated at 37° C., and medium aliquots were harvested at the indicated times, flash frozen, stored at −70° C. and titrated later in duplicate. Each value is the mean titer of two wells.

FIG. 8 shows indirect immunofluorescence of HEp-2 cells infected with rBRSV/A2-G1F2, rBRSV/A2, or rA2. Cells were infected at an MOI of 0.1, incubated at 37° C. for 96 hours, fixed with acetone, permeabilized and reacted with monoclonal antibody 021/1G, specific to the G protein of HRSV, or with monoclonal antibody 44F, specific to the F protein of HRSV. Antibody binding was visualized by reaction with a tagged antibody specific to murine IgG.

FIG. 9 details construction of a chimeric rBRSV/HRSV containing the M, G and F genes of HRSV. BRSV genes are shaded; HRSV genes are clear. Sequence position numbers that refer to HRSV genes are underlined. FIG. 9, panel A depicts modification of rBRSV/A2 to contain a unique MluI site at position 3204, within the intergenic region between the P and M genes (P-M IG). The sequence of the IG is shown, with small case letters indicating the original nucleotide assignments. The underlined letters indicate the Mlul site created by the 5 nucleotide substitutions. Nucleotide sequence position numbers are relative to the complete rBRSV antigenome (Buchholz et al., *J. Virol.* 73:251-259, 1999; Buchholz et al., *J. Virol.* 74:1187-1199, 2000; GenBank accession number AF092942 or complete rHRSV antigenome in Collins et al., *Proc. Natl. Acad. Sci. USA* 92:11563-11567, 1995); sequence position numbers that refer to the HRSV sequence are underlined. FIG. 9, panel B illustrates modification of rBRSV/A2 to create rBRSV/A2-MGF. The Mlul-SalI fragment containing the BRSV M and SH genes was excised and replaced with an MluI-SalI fragment containing the HRSV M gene. The MluI-SalI fragment containing the HRSV M gene is shown in the box. Also shown is the sequence immediately upstream of the MluI site, including the BRSV P gene-end sequence, and the sequence immediately downstream of the SalI site, including the intergenic sequence between the M and G genes (M-G IG), the HRSV G gene-start signal, and the ATG (bold, italics) that begins the G ORF. FIG, 9, panel C depicts the structure of the genome of rBRSV/A2-MGF.

FIG. 10 depicts the structures of the genomes of recombinant BRSV (rBRSV, top) and five BRSV/HRSV chimeric viruses in which specific BRSV genes (shaded rectangles) were replaced with their HRSV counterparts (open rectangles). In addition, in the bottom two viruses the G and F genes were moved from their normal positions to positions 3 and 4 or 1 and 2. In the diagram of rBRSV, several restriction sites are indicated. Restriction sites used in the various constructions are indicated: the Kpnl site occurs naturally and the others were introduced as necessary (Buchholz, et al., *J. Virol.* 73:251-9, 1999; Buchholz, et al. *J. Virol.* 74:1187-1199, 2000, each incorporated herein by reference).

FIG. 11 depicts multicycle growth of the BRSV/HRSV chimeric viruses rBRSV/A2-G3F4 (top panel) and HEx (bottom panel) compared to rHRSV (rA2) and rBRSV parental viruses as well as the previously-described chimeric viruses rBRSV/A2-GF (previously called rBRSV/A2; Buchholz, 2000, supra) and rBRSV/A2-G1F2. Monolayer cultures of Vero cells were infected at an input multiplicity of infection of 0.1 and incubated at 37° C. Samples from the overlying medium were harvested at the indicated times and virus titers were determined by the limiting dilution method. To 0.1 ml of serial 10-fold virus dilutions per well, 104 BHK-21 cells were added in a 0.1 ml volume. After 48 hours, cells were fixed in 80% acetone, and an indirect immunofluorescence assay using an antibody specific to the BRSV M protein, cross-reactive with the HRSV M protein, was done, and foci of infected cells were counted (see, Buchholz et al., *J. Virol.* 73:251-9, 1999 (incorporated herein by reference).

Figure 12:
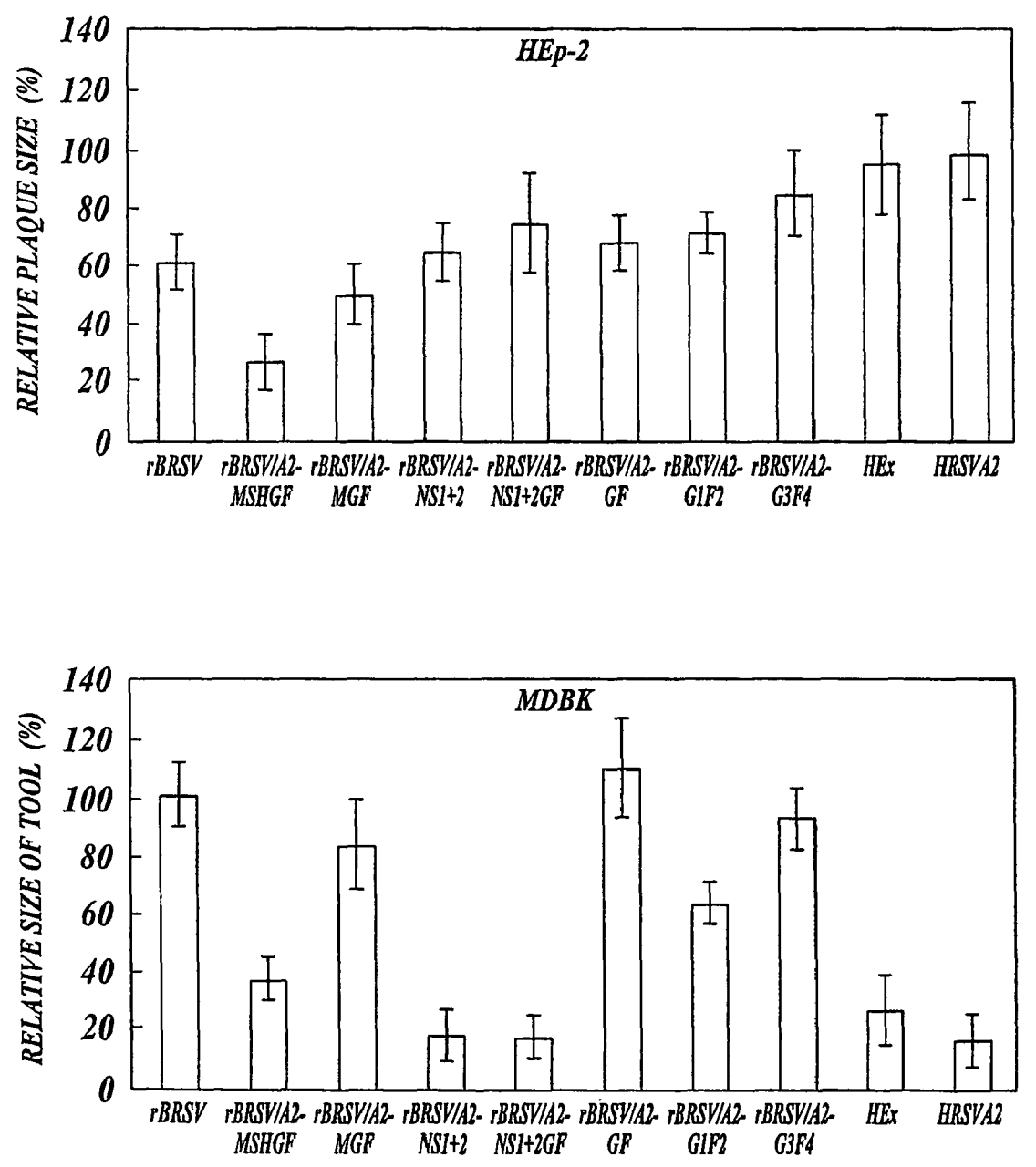

FIG. 12 compares the size of the plaque or focus formed by the indicated viruses on human HEp-2 cells (top panel) versus bovine MDBK cells (bottom panel), expressed as a percentage compared to HRSV (HEp-2 cells) or BRSV (MDBK cells).

Figure 13A:
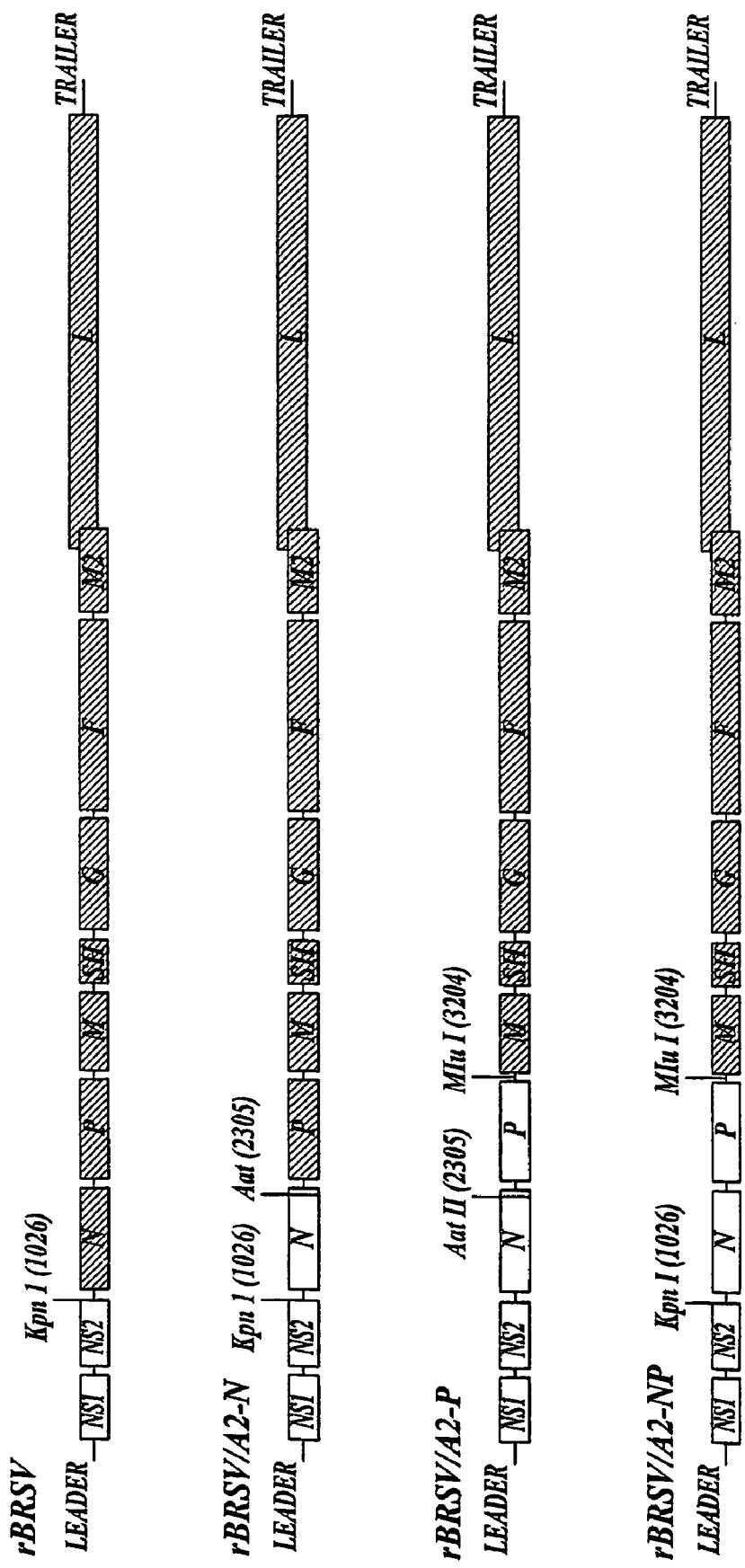

FIGS. 13A and 13B depict the structures of the genomes of recombinant BRSV in which the N and/or P genes were replaced by their HRSV counterparts. FIG. 13A shows chimeras in which these substitutions were made in the rBRSV backbone, and FIG. 13B shows chimeras in which the backbone was the rBRSV/A2-NS1+2 virus.

Figure 14:
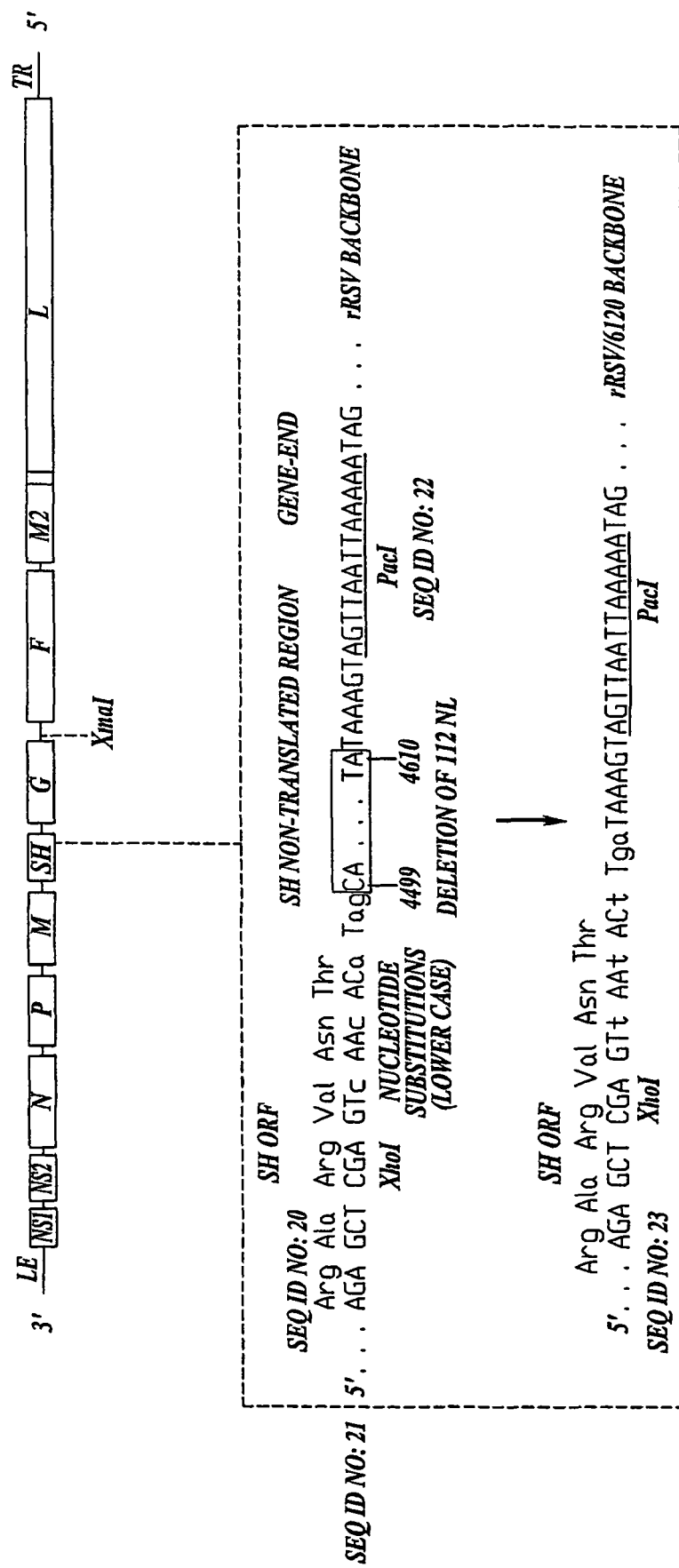

FIG. 14 Diagram of the genomic RNA of the recombinant rRSV/6120 virus containing a deletion in the SH gene, drawn as the negative sense RNA, 3' to 5', with each encoded mRNA indicated with a rectangle and non mRNA-coding extragenic and intergenic regions as a horizontal line. The parent RSV antigenomic cDNA was as described previously (Collins, et al, *Proc. Natl. Acad. Sci. USA* 92:11563-11567, 1995), with the further modification of an XmaI site in the G-F intergenic region (Bukreyev, et al., *J. Virol.* 70:6634-6641, 1996, incorporated herein by reference). This cDNA was modified (i) to contain five translationally-silent nucleotide substitutions in the last four codons of the SH ORF including the translational stop codon and (ii) to delete 112 nucleotides (positions 4499-4610) of the complete antigenomic sequence from the downstream non-translated region of the SH gene (box). The XhoI and PacI sites used in the construction are italicized and labeled, the SH gene-end signal is underlined, the SH codons are shown as triplets, nucleotide substitutions are in small case, and the deleted sequence is represented with a box with the sequence positions indicated.

Figure 15A:
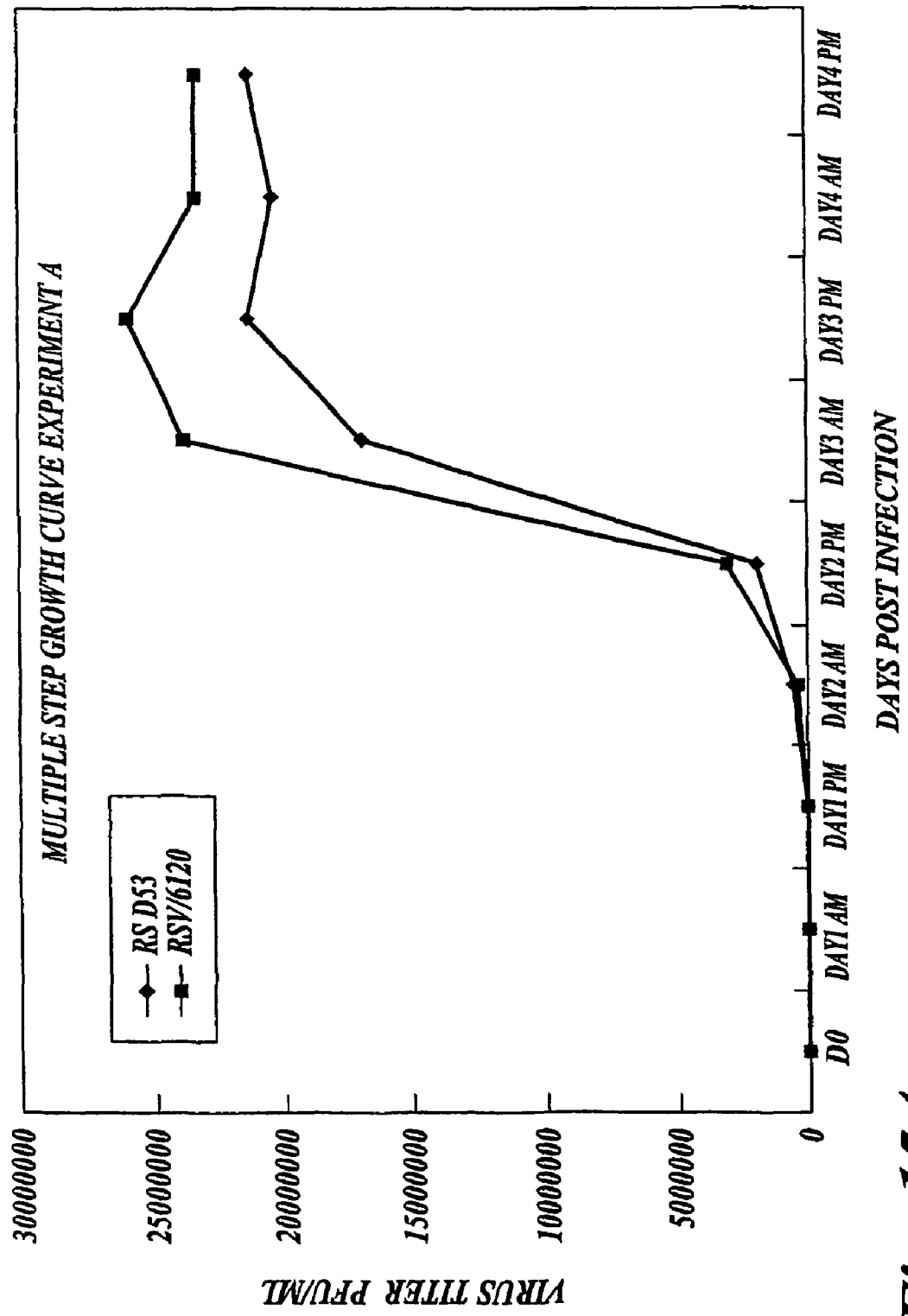
Figure 15B:
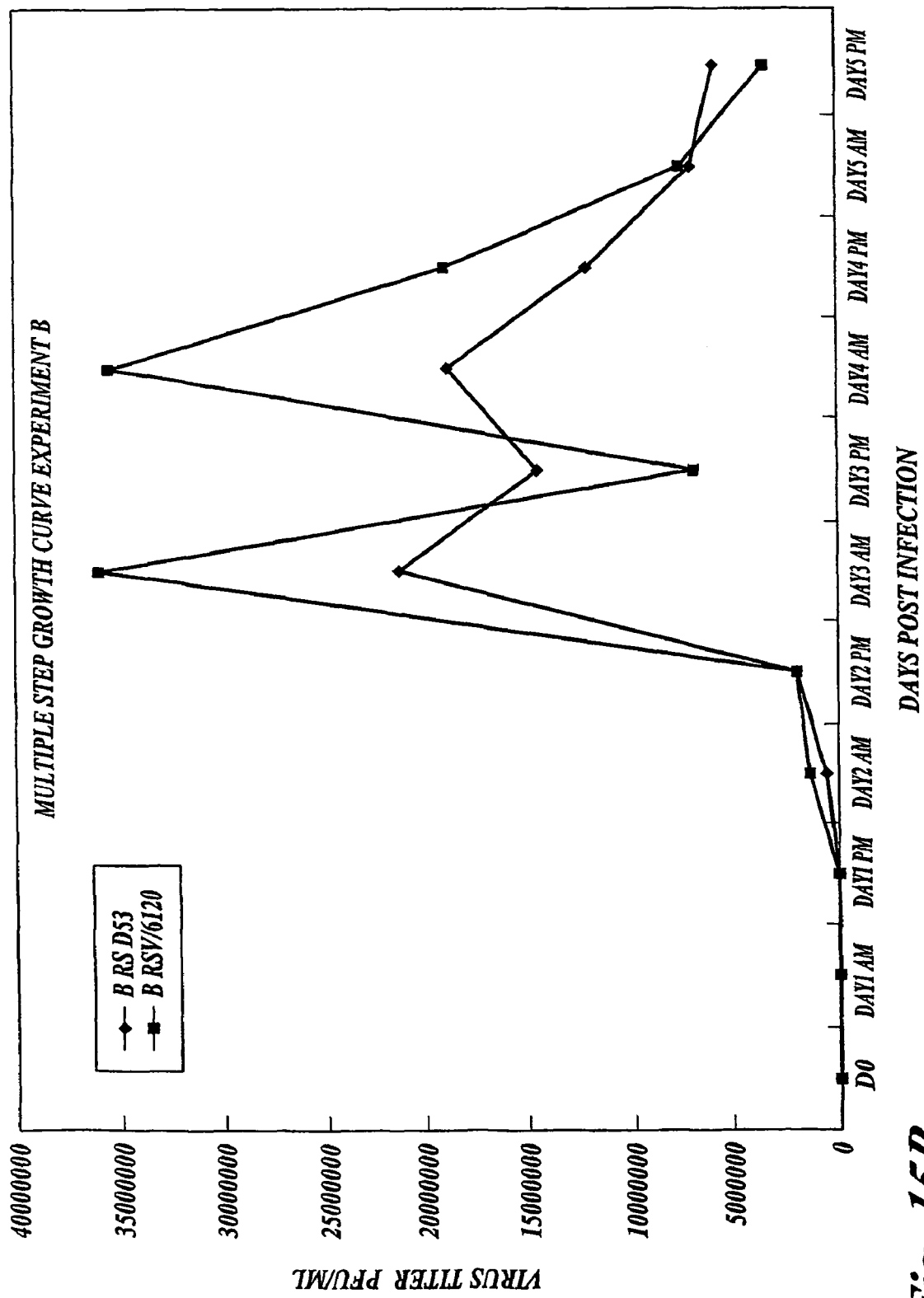

FIGS. 15A-15B Growth kinetics of rRSV/6120, containing a deletion in the SH gene, compared to its full length recombinant rRSV parent D53. Three sets (FIG. 15A, FIG. 15B and FIG. 15C) of monolayer cultures of HEp-2 cells were infected with the indicated virus at an input multiplicity of infection of 0.005. Following an adsorption period, cells were incubated at 37° C. At 12 h intervals, the medium was harvested in its entirety and aliquots were flash-frozen for later titration. The cells were washed three times and fresh medium was added and the incubation continued. At the end of the experiment, the samples were analyzed by plaque assay to determine virus titer.

DESCRIPTION OF THE SPECIFIC EMBODIMENTS

The present invention provides recombinant respiratory syncytial viruses (RSVs) which are modified by shifting a gene order or spatial position of one or more genes within a recombinant RSV genome or antigenome to generate a vaccine virus that is infectious and attenuated in humans and other mammals. Typically, the recombinant RSV genome or antigenome is modified by repositioning one or more "shifted" genes or gene segments, directly or indirectly via introduction, deletion or rearrangement of a second, "displacement polynucleotide" within the genome, resulting in a positional shift of the subject "shifted" gene or genome segment to a more promoter-proximal or promoter-distal position. Shifting of gene or genome segment positions in this context is determined to a position of the subject gene or genome segment in a parent RSV genome or antigenome prior to introduction of the gene shift, for example relative to the position of the subject gene or genome segment in a wild type RSV genome or antigenome (e.g., HRSV A2 or BRSV kansas strains) or in a parental recombinant RSV genome or antigenome as disclosed herein, prior to the gene shift.

In certain aspects of the invention, the gene position-shifted RSV features one or more shifted genes or genome segments that are shifted to a more promoter-proximal or promoter-distal position by insertion, deletion, or rearrangement of one or more displacement polynucleotides within the partial or complete recombinant RSV genome or antigenome. The displacement polynucleotides may comprise an RSV gene or genome segment, including an RSV gene or genome segment from a different or "heterologous" RSV (e.g., in the case of a heterologous gene or genome segment inserted into genome or antigenome of a different RSV). Alternatively, the displacement polynucleotides may be from a non-RSV source, including from a non-RSV pathogen such as parainfluenza virus (PIV) or measles virus. The displacement polynucleotides may encode a protein or a portion of a protein, such an immunogenic domain or epitope of a glycoprotein, or they may represent an incomplete or impaired coding sequence, including non-coding and nonsense polynucleotide sequences.

In certain aspects of the invention, the recombinant RSV features one or or positionally shifted genes or genome segments that may be shifted to a more promoter-proximal or promoter-distal position by insertion, deletion, or rearrangement of one or more displacement polynucleotides within the partial or complete recombinant RSV genome or antigenome. In certain aspects, the displacement polynucleotides are RSV genes or genome segments. In other aspects, displacement polynucleotides lack a complete open reading frame (ORF). Within more detailed embodiments, displacement polynucleotides comprise polynucleotide inserts of between 150 nucleotides (nts) and 4,000 nucleotides in length. Displacement polynucleotides may be inserted or rearranged into a non-coding region (NCR) of the recombinant genome or antigenome, or may be incorporated in the recombinant RSV genome or antigenome as a separate gene unit (GU).

Gene position shifts within the recombinant RSV of the invention are typically determined relative to the genome or antigenome "promoter". The RSV promotor contains the polymerase initiation site, which is a conserved sequence element recognized by the polymerase. The promoter is located at the 3' end of the genome or antigenome, within approximately the thirty 3'-terminal nucleotides. In the case of the RSV genome, the promoter directs both transcription and replication. However, the antigenome "promoter" which lacks transcription signals and only naturally controls replication can be modified to direct transcription by insertion of known transcription signals. For the purposes of describing the invention, the RSV promotor is thus construed to reside at the 3' end of either the genome or antigenome, whereby the terms "promoter-proximal" and "promoter-distal" used herein alternately refer to a direction toward, or away from, respectively, the 3' end of the genome or antigenome.

Thus provided within the invention are isolated polynucleotide molecules, vectors (expression constructs), and recombinant viruses incorporating a recombinant RSV genome or antigenome—wherein one or more genes or gene segments is/are shifted to a more promoter-proximal or promoter-distal position within the recombinant genome or antigenome compared to a parental or wild type position of the gene in the RSV gene map. Shifting the position of genes in this manner provides for a selected increase or decrease in expression of one or more positionally "shifted" genes, depending on the nature and degree of the positional shift. In one embodiment, RSV glycoproteins are upregulated by shifting one or more glycoprotein-encoding genes to a more promoter-proximal position. Genes of interest for manipulation to create gene position-shifted RSV include any of the NS1, NS2, N, P, M, SH, M2(ORF1), M2(ORF2), L, F or G genes or a genome segment that may be part of a gene or extragenic. A variety of additional mutations and nucleotide modifications are provided within the gene position-shifted RSV of the invention to yield desired phenotypic and structural effects.

The recombinant construction of human-bovine RSV yields a viral particle or subviral particle that is infectious in mammals, particularly humans, and useful for generating immunogenic compositions for clinical use. Also provided within the invention are novel methods and compositions for designing and producing attenuated, gene position-shifted RSV, as well as methods and compositions for the prophylaxis and treatment of RSV infection. Gene position-shifted RSV and immunogenic compositions according to the invention may elicit an immune response to a specific RSV subgroup or strain, or they may elicit a polyspecific response against multiple RSV subgroups or strains. Gene position-shifted RSV of the invention are thus infectious and attenuated in humans and other mammals. In related aspects, the invention provides novel methods for designing and producing attenuated, gene position-shifted RSV that are useful in various compositions to generate a desired immune response against RSV in a host susceptible to RSV infection. Included within these aspects of the invention are novel, isolated polynucleotide molecules, vectors, and infected cells incorporating such molecules that comprise a gene position-shifted RSV genome or antigenome. Gene position-shifted RSV according to the invention may elicit an immune response to a specific RSV subgroup or strain, or a polyspecific response against multiple RSV subgroups or strains. Yet additional compositions and methods are provided for designing and producing attenuated, gene position-shifted RSV as vectors for incorporating antigenic determinants of other pathogens to generate a desired immune response against different pathogens of interest. Also provided within the invention are methods and compositions incorporating gene position-shifted RSV for prophylaxis and treatment of infection and disease caused by RSV and other pathogens.

The present invention culminates and supplements a continuing line of discovery founded upon the recent advent and refinement of methods for producing infectious recombinant RSV from cDNA. Based upon this work, it has been possible to directly investigate the roles of RNA and protein structures in RSV gene expression and replication. These investigations are described or reported in U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999; U.S. Provisional Patent Application No. 60/129,006, filed by Murphy et al. on Apr. 13, 1999; Crowe et al., *Vaccine* 12: 691-699, 1994; and Crowe et al., *Vaccine* 12: 783-790, 1994; Collins, et al., *Proc Nat. Acad. Sci. USA* 92:11563-11567, 1995; Bukreyev, et al., *J Virol* 70:6634-41, 1996, Juhasz et al., *J. Virol.* 71(8):5814-5819, 1997; Durbin et al., *Virology* 235: 323-332, 1997; Karron et al., *J. Infect. Dis.* 176:1428-1436, 1997; He et al. *Virology* 237:249-260, 1997; Baron et al. *J. Virol.* 71:1265-1271, 1997; whitehead et al., *Virology* 247(2): 232-9, 1998a; Whitehead et al., *J. Virol.* 72(5):4467-4471, 1998b; Jin et al. *Virology* 251:206-214, 1998; Bukreyev, et al., *Proc. Nat. Acad. Sci. USA* 96:2367-2372, 1999; Bermingham and Collins, *Proc. Natl. Acad. Sci. USA* 96:11259-11264, 1999 Juhasz et al., *Vaccine* 17:1416-1424, 1999; Juhasz et al., *J. Virol.* 73:5176-5180, 1999; Teng and Collins, *J. Virol.* 73:466-473, 1999; Whitehead et al., *J. Virol.* 73:9773-9780, 1999; Whitehead et al., *J. Virol.* 73:871-877, 1999; and Whitehead et al., *J. Virol.* 73:3438-3442, 1999, Jin, et al., *Virology* 273:210-8, 2000; Jin, et al., *J. Virol.* 74:74-82, 2000; Teng, et al., *J. Virol.* 74:9317-21, 2000, each of which are incorporated herein by reference in their entirety for all purposes).

With regard to gene position-shifted RSV of the invention, a number of the foregoing incorporated disclosures have focused on modification of the naturally-occurring gene order in RSV. For example, each of the NS1, NS2, SH and G genes have been successfully deleted individually in infectious RSV recombinants, thereby shifting the position of downstream genes relative to the viral promoter. In other recombinants within the invention, the NS1 and NS2 gene were deleted together, shifting the remaining genes in promoter-proximal direction within the recombinant RSV genome or antigenome. For example, when NS1 and NS2 are deleted together, N is moved from position 3 to position 1, P from position 4 to position 2, and so on. Deletion of any other RSV gene within alternate embodiments of the invention will similarly shift the position (relative to the promoter) of those genes which are located further downstream. For example, SH occupies position 6 in wild type virus, and its deletion does not affect M at position 5 (or any other upstream gene) but moves G from position 7 to 6 relative to the promoter. It should be noted that gene deletion also can occur (rarely) in a biologically-derived mutant virus (Karron et al., *Proc. Natl. Acad. Sci. USA* 94:13961-13966, 1997; incorporated herein by reference). Note that "upstream" and "downstream" refer to the promoter-proximal and promoter-distal directions, respectively (the promoter is at the 3' leader end of negative-sense genomic RNA).

Gene order shifting modifications (i.e., positional modifications moving one or more genes to a more promoter-proximal or promoter-distal location in the recombinant viral genome) with gene position-shifted RSV of the invention result in viruses with altered biological properties. For example, RSV lacking NS1, NS2, SH, G, NS1 and NS2 together, or SH and G together, have been shown to be attenuated in vitro, in vivo, or both. It is likely that this phenotype was due primarily to the loss of expression of the specific viral protein. However, the altered gene map also likely contributed to the observed phenotype. This effect is well-illustrated by the SH-deletion virus, which grew more efficiently than wild type in some cell types, probably due to an increase in the efficiency of transcription, replication or both resulting from the gene deletion and resulting change in gene order and possibly genome size. In other viruses, such as RSV in which NS1 and/or NS2 were deleted, altered growth that might have occurred due to the change in gene order likely was obscured by the more dominant phenotype due to the loss of expression of the RSV protein(s).

Yet additional changes have been successfully introduced to change the gene order of RSV to improve its properties as a live-attenuated vaccine. In specific examples demonstrating efficacy of the invention, the RSV G and F genes were shifted, singly and in tandem, to a more promoter-proximal position relative to their wild-type gene order. These two proteins normally occupy positions 7 (G) and 8 (F) in the RSV gene order (NS1-NS2-N-P-M-SH-G-F-M2-L). In order to increase the possibility of successful recovery, these positional manipulations of G and F were performed in a version of RSV in which the SH gene had been deleted (see, e.g., Whitehead et al., *J. Virol.*, 73:3438-42 (1999), incorporated herein by reference). This facilitates viral recovery because this virus makes larger plaques in vitro (Bukreyev et al., *J. Virol.* 71:8973-82, 1997, incorporated herein by reference). G and F were then moved individually to position 1, or were moved together to positions 1 and 2, respectively.

Surprisingly, recombinant RSV were readily recovered in which G or F were moved to position 1, or in which G and F were moved to positions 1 and 2, respectively. This result differed greatly from previous reported studies with vesicular stomatitis virus (VSV), where movement of the single VSV glycoprotein gene by only two positions was very deleterious to virus growth (Ball et al., *J. Virol.* 73:4705-4712, 1999, incorporated herein by reference). The ability to recover these altered viruses also was surprising because RSV replicates inefficiently and because RSV has a complex gene order and movement of the glycoprotein genes involved a large number of position changes. Indeed, the rearranged RSV's grew at least as well as their immediate parent having the wild type order of genes. As indicated above, this is particularly important for RSV, since the wild type virus grows inefficiently in cell culture and a further reduction in replication in vitro would likely render vaccine preparation unfeasible. Thus, it is remarkable that all of the NS1-NS2-N-P-M proteins could be displaced by one or two positions relative to the promoter without a significant decrease in growth fitness. In addition, examination of the expression of the G glycoprotein showed that it was increased up to several-fold over that of its parent virus. This indicated that a vaccine virus containing G and/or F in the first position expresses a higher molar amount of these protective antigens compared to the other viral proteins, and thus represent a virus with desired vaccine properties.

Similarly extensive modifications in gene order also were achieved with two highly attenuated RSV vaccine candidates in which the NS2 gene was deleted on its own, or in which the NS1 and NS2 genes were deleted together, as described in more detail in the above-incorporated references. In these two vaccine candidates, the G and F glycoproteins were moved together to positions 1 and 2 respectively, and the G, F and SH glycoproteins were deleted from their original downstream position. Thus, the recovered viruses G1F2ΔNS2ΔSH and G1F2/ΔNS1ΔNS2ΔSH had two and three genes deleted respectively in addition to the shift of the G and F genes. To illustrate the extent of the changes involved, the gene orders of wild type RSV (NS1-NS2-N-P-M-SH-G-F-M2-L) and the G1F2/ΔNS2ΔSH virus (G-F-NS1-N-P-M-M2-L) or the ΔNS1ΔNS2ΔSH (G-F-N-P-M-M2-L) can be compared. This shows that the positions of most or all of the genes relative to the promoter were changed. Nonetheless, these highly attenuated derivatives retained the capacity to be grown in cell culture.

Yet additional changes have been successfully introduced to change the gene order of RSV in a human-bovine chimeric RSV to improve its properties as a live-attenuated vaccine (See, U.S. patent application Ser. No. 09/602,212, filed by Bucholz et al. on Jun. 23, 2000, its corresponding PCT application published as WO 01/04335 on Jan. 18, 2001, and its priority provisional U.S. Application No. 60/143,132 filed on Jul. 9, 1999, each incorporated herein by reference). As illustrated in the examples below, an infectious recombinant human-bovine chimeric RSV (rBRSV/HRSV) was successfully constructed and recovered in which the HRSV G and F genes are substituted into a recombinant bovine RSV (rBRSV) background. The resulting human-bovine chimera contains two genes of HRSV, namely G and F, and eight genes from BRSV, namely NS1, NS2, N, P, M, SH, M2 and L. In addition to this basic substituted glycoprotein construction, the HRSV G and F genes are shifted to a more promoter-proximal position in the rBRSV backbone, i.e., relative to the wild-type gene order position of the F and G genes in the RSV genome. More specifically, the F and G genes were moved from their usual location relative to the promoter, namely gene positions 7 and 8, respectively, to positions 1 and 2, respectively. The resulting chimeric recombinant virus, rBRSV/A2-G1F2, is very similar in its levels of F and G protein expression as detected by immunofluorescence to that of wt HRSV, which result is interpreted to show increased expression of the G and F glycoproteins attributed to the promoter-proximal shift of the genes. Since the present rBRSV/A2-G1F2 virus bears the same constellation of BRSV genes in its genetic background, it is likely to share this strong host range restriction phenotype. In this context, the increased expression of the two protective antigens in vivo will increase the immunogenicity of this virus to produce highly desirable vaccine properties.

RSV is a nonsegmented negative strand RNA virus of Order Mononegavirales. The mononegaviruses constitute a large and diverse Order that includes four families: Family Rhabdoviridae, represented by vesicular stomatitis virus (VSV) and rabies virus; Family Bornaviridae, represented by borna disease virus; Family Filoviridae, represented by Marburg and Ebola viruses, and Family Paramyxoviridae. This latter family is further divided into two subfamilies: Paramyxovirinae, which includes Sendai, measles, mumps and parainfluenza viruses, and Pneumovirinae, which includes respiratory syncytial virus.

The genome of a mononegavirus is a single strand of RNA that contains from 5 (VSV) to 11 (RSV) genes arranged in a linear array. The mononegavirus genome does not encode protein directly (hence the designation "negative sense"), but rather encodes complementary positive-sense mRNAs that each encode one or more proteins. Typically, a gene begins with a short gene-start signal and ends with a short gene-end signal. These signals usually consist of 8 to 12 nucleotides and usually are highly conserved between genes of a given virus and to a lesser extent between related viruses.

In the case of RSV, the genome is more than 15.2 kb in length and is transcribed into 10 separate major mRNAs that encode 11 identified proteins. Specifically, the RSV gene order is 3'-NS1-NS2-N-P-M-SH-G-F-M2-L-5', and the M2 mRNA encodes two proteins, M2-1 and M2-2 from overlapping ORFs. The gene-start and gene-end signals of RSV, together with sequences involved in RNA replication and in promoter function, also have been identified and analyzed in ongoing work (Bukreyev et al., *J. Virol.* 70:6634-6641, 1996; Collins et al., *Proc. Natl. Acad. Sci. USA* 88:9663-9667, 1991; Mink et al., *Virology* 185:615-624, 1991; Grosfeld et al., *J. Virol.* 69:5677-5686, 1995; Hardy and Wertz, *J. Virol.* 72:520-526, 1998; Hardy et al., *J. Virol.* 73:170-176, 1999; Kuo et al., *J. Virol.* 70:6143-6150, 1996; Kuo et al., *J. Virol.*

70:6892-6901, 1996; Samal and Collins, *J. Virol.* 70:5075-5082, 1996; Kuo et al., *J. Virol.* 71:4944-4953, 1997; Fearns and Collins, *J. Virol.* 73:388-397, 1999; each incorporated herein by reference).

The 3' end of a mononegavirus genome contains a promoter that directs entry of the polymerase Lamb and Kolakofsky, *Fields Virology* 1:1177-1204, 1996; and Wagner and Rose, *Fields Virology* 121-1136, 1996; each incorporated herein by reference). This promoter is contained completely or in part in an extragenic leader region at the 3' end of the genome. The polymerase then transcribes the genome 3'-to-5' in a linear, stop-restart manner guided by the gene-start and gene-end signals. The gene-start signal of each gene directs initiation of the synthesis of the corresponding mRNA and the gene-end signal directs polyadenylation, termination and release of the corresponding mRNA. The polymerase then remains template-bound and reinitiates at the next downstream gene-start signal. This process is repeated to transcribe one gene after another in their 3'-to-5' order (Lamb and Kolakofsky, *Fields Virology* 1:1177-1204, 1996; Wagner and Rose, *Fields Virology*, 1121-1136, 1996; Abraham and Banerjee, *Proc. Natl. Acad. Sci. USA* 73:1504-1508, 1976; Ball and White, *Proc. Natl. Acad. Sci. USA*, 73:442-446, 1976; Ball, *J. Virol.* 21:411-414, 1977; Banerjee et al., *J. Gen. Virol.* 34:1-8, 1977; Iverson and Rose, *Cell* 23:477-484, 1981; Iverson and Rose, *J. Virol.* 44:356-365, 1982; Banerjee et al., *Pharmacol. Ther.* 51:47-70, 1991; each incorporated herein by reference).

Four of the RSV proteins enumerated above are nucleocapsid/polymerase proteins, namely the major nucleocapsid N protein, the phosphoprotein P, and polymerase protein L, and the transcription antitermination protein M2-1. Three are surface glycoproteins, namely the attachment G protein, the fusion F glycoprotein responsible for penetration and syncytium formation, and the small hydrophobic SH protein of unknown function. The matrix M protein is an internal virion protein involved in virion formation. There are two nonstructural proteins NS1 and NS2 of unknown function. Finally, there is a second open reading frame (ORF) in the M2 mRNA which encodes an RNA regulatory factor M2-2.

The G and F proteins are the major neutralization and protective antigens (Collins, et al., *Fields Virology* 2:1313-1352, 1996; Connors, et al., *J. Virol.* 66:1277-81, 1992). Resistance to reinfection by RSV is largely mediated by serum and mucosal antibodies specific against these proteins. RSV-specific cytotoxic T cells are also induced by RSV infection and can be directed against a number of different proteins, but this effector has not yet been shown to be an important contributor to long term resistance to reinfection. However, both CD8+ and CD4+ cells can be important in regulating the immune response, and both may be involved in viral pathogenesis (Johnson, et al., *J. Virol.* 72:2871-80, 1998; Srikiatkhachorn and Braciale, *J. Exp. Med.* 186:421-32, 1997). Thus, F and G are the most important antigenic determinants, but other proteins can also play important roles in the immune response.

RSV isolates can be segregated into two antigenic subgroups, A and B, by reactivity with monoclonal antibodies (Anderson, et al., *J. Infect. Dis.* 151:626-33, 1985, Mufson, et al., *J. Gen. Virol.* 66:2111-24, 1985). The two subgroups exhibit differences across the genome, but are the most divergent in the ectodomain of the G protein where the percent amino acid sequence divergence can exceed 50% and the antigenic divergence is 95% based on reactivity of monospecific polyclonal antisera (Johnson, et al., *Proc. Natl. Acad. Sci. USA* 84:5625-9, 1987; Johnson, et al., *J. Virol.* 61:3163-6, 1987). The F protein is approximately 10% divergent by amino acid sequence and 50% divergent antigenically between RSV A and B subgroups (Johnson, et al., *J. Virol.* 61:3163-6, 1987; Johnson and Collins, *J. Gen. Virol.* 69:2623-8, 1988). Thus, both subgroups should be represented in a vaccine.

RSV and other mononegaviruses have been reported to exhibit a gradient of decreasing gene transcription, such that the most promoter-proximal gene is transcribed the most efficiently, and each gene thereafter displays an incrementally-decreasing efficiency of transcription (Lamb and Kolakofsky, *Fields Virology*, 1:1177-1204, 1996; Wagner and Rose, *Fields Virology* 1121-1136, 1996; Abraham and Banerjee, *Proc. Natl. Acad. Sci. USA* 73:1504-1508, 1976; Ball and White, *Proc. Natl. Acad. Sci. USA* 73:442-446, 1976; Ball, *J. Virol.* 21:411-414, 1977; Banerjee et al., *J. Gen. Virol.*, 34:1-8, 1977; Iverson and Rose, *Cell* 23:477-484, 1981; Iverson and Rose, *J. Virol.* 44:356-365, 1982; Banerjee et al., *Pharmacol. Ther.* 51:47-70, 1991; each incorporated herein by reference). This gradient of gene expression has been reported and partially characterized for RSV (Collins and Wertz, *Proc. Natl. Acad. Sci. USA* 80:3208-3212, 1983; Collins et al., *J. Virol.* 49:572-578, 1984; Dickens et al., *J. Virol.* 52:364-369, 1984; each incorporated herein by reference). This gradient is thought to be partially attributed to "fall-off" of the polymerase during sequential transcription. Studies with the rhabdovirus VSV, one of the simplest of the mononegaviruses, suggest that fall-off occurs primarily at the intergenic regions (Iverson and Rose, *Cell* 23:477-484, 1981; Iverson and Rose, *J. Virol.* 44:356-365, 1982; each incorporated herein by reference), although the disproportionately low abundance of the large L mRNA suggests that there also is significant fall-off within genes.

The gradient of gene transcription reported among mononegaviruses is thought to be a major factor that determines the relative molar ratios of the various viral mRNAs within an infected cell. This phenomenon in turn is thought to be a major factor determining the relative molar ratios of viral proteins. All mononegaviruses have genes encoding the following five proteins or counterparts thereof: an RNA-binding nucleocapsid protein N, a phosphoprotein P, an internal virion matrix protein M, an attachment protein G, HA, or HN, and a large polymerase protein L. Furthermore, these are always found in the 3'-to-5' order N-P-M-G-L. One interpretation is that this genomic organization reflects a common need among the mononegaviruses for large amounts of the N and P proteins, a small amount of L, and intermediate amounts of M and G. Alternatively, it has been suggested that the lack of homologous recombination in mononegaviruses has resulted in the retention of an ancestral gene order that is not necessarily optimal for the virus (Ball et al., *J. Virol.*, 73:4705-4712, 1999; incorporated herein by reference).

The constrained gene order and polar nature of transcription has been proposed as an important factor in the regulation of gene expression among mononegaviruses. However, other secondary factors are also believed to affect the relative levels of expression of one or more of the mononegaviral proteins, including differences in the efficiencies of cis-acting RNA signals, differences in efficiencies of translation of various mRNAs, and differences in processing and stability of proteins.

The simple, prototypic mononegavirus, VSV, has 5 genes (Wagner and Rose, *Fields Virology*, 1121-1136, 1996; Schubert et al., *J. Virol.* 51:505-514, 1984; each incorporated herein by reference). However, other mononegaviruses have as many as 11 (RSV) or 12 (pneumonia virus of mice) genes (Barr et al., *J. Virol.*, 68:5330-5334, 1994; incorporated herein by reference). These include proteins such as the fusion F gene found in all paramyxoviruses and pneumoviruses, the C, D and V genes found in some paramyxoviruses, and the NS1, NS2, SH and M2 genes found in most pneumoviruses. Also, even among the five proteins that may be common to VSV and RSV (N, P, M, G and L), there is clear sequence relatedness only for L, and that relatedness is low (Poch et al., *Embo. J.* 8:3867-3674, 1989; Stec et al., *Virology* 183:273-287, 1991; each incorporated herein by reference).

Given this extensive difference in the array and structure of gene products, taken together with differences in the structure and function of trans- and cis-acting components, the features and properties of one mononegavirus, e.g., VSV, cannot be directly extrapolated to other mononegaviruses, such as RSV. This uncertainty is exemplified by the finding that the RSV polymerase consists of 4 rather than 3 proteins, with the additional one being the M2-1 transcription antitermination factor that has no counterpart in VSV (Hardy and Wertz, *J. Virol.* 72:520-526, 1998; Hardy et al., *J. Virol.* 73:170-176, 1999; Collins et al., *Proc. Natl. Acad. Sci. USA* 93:81-85, 1996; Fearns and Collins, *J. Virol.* 73:5852-5864, 1999; each incorporated herein by reference). This proved to be critical for the efficient recovery of recombinant RSV (Collins et al., *Virology* 259:251-255, 1999; incorporated herein by reference). In addition, RSV RNA synthesis is further regulated by at least two proteins, NS1 and M2-2, which do not have counterparts in VSV (Bermingham and Collins, *Proc. Natl. Acad. Sci. USA* 96:11259-64, 1999; Whitehead et al., *J. Virol.* 73:3438-3442, 1999; Atreya et al., *J. Virol.* 72:1452-61, 1998; Jin et al., *J. Virol.* 74:74-82, 2000; each incorporated herein by reference).

A number of important features of VSV gene expression and regulation also do not appear to have any relevance to many other mononegaviruses and in particular to RSV, such as the involvement of terminal complementarily in control of VSV gene expression (Wertz et al., *Proc. Natl. Acad. Sci. USA* 91:8587-8591, 1994; Whelan and Wertz, *J. Virol.* 73:297-306, 1999; Peeples and Collins, *J. Virol.* 74:146-155, 2000; each incorporated herein by reference), the highly conserved VSV intergenic regions that are directly involved in gene expression (Barr et al., *J. Virol.* 71:1794-1801, 1997; incorporated herein by reference) whereas those of RSV are not (Kuo et al., *J. Virol.* 70:6143-6150, 1996; incorporated herein by reference), a VSV genomic packaging signal (Whelan and Wertz, *J. Virol.* 73:307-315, 1999; incorporated herein by reference) not found in other mononegavirus groups, and a control of VSV gene expression and replication by N protein (Wagner and Rose, *Fields Virology*, 1121-1136, 1996; Fearns et al., *Virology* 236:188-201, 1997; incorporated herein by reference). These features do not appear to occur in RSV (Peeples and Collins, *J. Virol.* 74:146-155, 2000; incorporated herein by reference), while in contrast RSV has important features of gene expression and regulation that do not occur in VSV, including divergent intergenic sequences that lack cis-acting functional elements (Kuo et al., *J. Virol.* 70:6143-6150, 1996; incorporated herein by reference), a gene overlap that mediates site-specific attenuation (Fearns and Collins, *J. Virol.* 73:388-397, 1999; Collins et al., *Proc. Natl. Acad. Sci. USA* 84:5134-5138, 1987; incorporated herein by reference), and the existence of a polymerase back-tracking mechanism critical for expression of the L gene (Fearns and Collins, *J. Virol.* 73:388-397, 1999; incorporated herein by reference). In particular, the existence of a transcription antitermination factor that modulates sequential transcription (Fearns and Collins, *J. Virol.* 73:5852-5864, 1999; incorporated herein by reference), specific regulatory proteins, site-specific attenuation, and gene-junction-specific modulation of transcription (Hardy et al., *J. Virol.* 73:170-176, 1999; incorporated herein by reference) contrast sharply with the situation with VSV.

In certain embodiments of the invention, gene position shifts are achieved by deletion of one or more of the RSV NS1, NS2, SH and/or G genes, which deletions are disclosed individually in the above-incorporated references. Alternative gene or genome segment deletions can be constructed involving any of the above identified RSV genes or genome segments, to alter gene position for remaining RSV genes. In more detailed embodiments, multiple genes or genome segments are deleted, as exemplified in the above-incorporated references by pairwise deletion of the NS1 and NS2 genes (Bukreyev et al., *J. Virol.* 71:8973-8982, 1997; Teng and Collins, *J. Virol.* 73:466-473, 1999; Whitehead et al., *J. Virol.* 73:3438-3442, 1999; incorporated herein by reference).

Deletion of one or more genes or genome segments within a recombinant RSV genome or antigenome has the effect of moving all downstream genes closer to the promoter (e.g., by shifting the downstream genes one or more gene positions in a promoter-proximal direction). For example, the RSV NS1 and NS2 genes are the first and second genes in the genome map, and their coordinate deletion alters the position of all of the remaining genes. Thus, when NS1 and NS2 are deleted together, N is moved from position 3 to position 1, P from position 4 to position 2, and so on. Alternatively, deletion of any other gene within the gene order will affect the position (relative to the promoter) only of those genes which are located even further downstream. For example, SH occupies position 6 in wild type virus, and its deletion does not affect M at position 5 (or any other upstream gene) but moves G from position 7 to 6 relative to the promoter. It should be noted that gene deletion also can occur (rarely) in biologically-derived virus. For example, a subgroup B RSV that had been passaged extensively in cell culture spontaneously deleted the SH and G genes (Karron et al., *Proc. Natl. Acad. Sci. USA* 94:13961-13966, 1997; incorporated herein by reference). Note that "upstream" and "downstream" refer to the promoter-proximal and promoter-distal directions, respectively (the promoter is at the 3' leader end of negative-sense genomic RNA).

A second example of gene order rearrangement useful within the invention involves the insertion of a gene, genome segment or heterologous polynucleotide sequence into the recombinant RSV genome or antigenome to alter gene order or introduce a promoter-relative gene position shift in the recombinant genome or antigenome (see, e.g., Bukreyev et al., *J. Virol.* 70:6634-6641, 1996; Bukreyev et al., *Proc. Natl. Acad. Sci. USA* 96:2367-2372, 1999; Moriya et al., *FEBS Lett.* 425:105-111, 1998; Singh and Billeter, *J. Gen. Virol.* 80:101-106, 1999; incorporated herein by reference). Each inserted gene displaces all downstream genes by one position relative to the promoter. These and other displacement polynucleotides may be inserted or rearranged into a non-coding region (NCR) of the recombinant genome or antigenome, or may be incorporated in the recombinant RSV genome or antigenome as a separate gene unit (GU).

As used herein, "RSV gene" generally refers to a portion of the RSV genome encoding an mRNA and typically begins at the upstream end with the 10-nucleotide gene-start (GS) signal and ends at the downstream end with the 12 to 13-nucleotide gene-end (GE) signal. Ten such genes for use within the invention are known for RSV, namely NS1, NS2, N, P, M, SH, G, F, M2 and L. The term "gene" is also used herein to refer to a "translational open reading frame" (ORF). ORF is more specifically defined as a translational open reading frame encoding a significant RSV protein, of which 11 are currently recognized: NS1, NS2, N, P, M, SH, G, F, M2-1 (alternatively, M2(ORF1)), M2-2 (alternatively, M2(ORF2)), and L. Thus, the term "gene" interchangeably refers to a genomic RNA sequence that encodes a subgenomic RNA, and to a ORF (the latter term applies particularly in a situation such as in the case of the RSV M2 gene, where a single mRNA contains two overlapping ORFs that encode distinct proteins). Collins et al., *J. Gen. Virol.* 71:3015-3020, 1990; Bermingham and Collins, *Proc. Natl. Acad. Sci. USA* 96:11259-11264, 1999; Ahmadian et al., *EMBO J.* 19:2681-2689, 2000; Jin et al., *J. Virol.* 74:74-82, 2000 (each incorporated herein by reference). When the term "gene" is used in the context of determining gene position relative to a promoter position, the term ordinarily refers strictly to an mRNA-encoding sequence bordered by transcription gene-start and gene-end signal motifs (Collins et al., *Proc. Natl. Acad. Sci. USA* 83:4594-4598, 1986; Kuo et al., *J. Virol.* 70:6892-6901, 1996; each incorporated herein by reference).

By "genome segment" is meant any length of continuous nucleotides from the RSV genome, which may be part of an ORF, a gene, or an extragenic region, or a combination thereof.

Genes and genome segments that may be selected for use as inserts, substitutions, deleted elements, or rearranged elements within gene position-shifted RSV of the invention include genes or genome segments encoding a NS1, NS2, N, P, M, SH, M2(ORF1), M2(ORF2), L, F or G protein or portion thereof. Regulatory regions, such as the extragenic leader or trailer regions, can also be considered. In preferred embodiments of the invention, chimeric RSV incorporates one or more heterologous gene(s) that encode an RSV F, G or SH glycoprotein. Alternatively, the recombinant RSV may incorporate a genome segment encoding a cytoplasmic domain, transmembrane domain, ectodomain or immunogenic epitope of a RSV F, G or SH glycoprotein. These immunogenic proteins, domains and epitopes are particularly useful within gene position-shifted RSV because they generate novel immune responses in an immunized host. In particular, the G and F proteins, and immunogenic domains and epitopes therein, provide major neutralization and protective antigens. In addition, genes and genome segments encoding non-RSV proteins, for example, an SH protein as found in mumps and SV5 viruses, may be incorporated within gene position-shifted RSV of the invention. Regulatory regions, such as the extragenic 3' leader or 5' trailer regions, and gene-start, gene-end, intergenic regions, or 3' or 5' non-coding regions, are also useful as heterologous (originating from a different RSV strain or subgroup or from a non-RSV source such as PIV, measles, mumps, etc.) substitutions or additions.

For example, addition or substitution of one or more immunogenic gene(s) or genome segment(s) from a human RSV subgroup or strain to or within a bovine recipient genome or antigenome yields a recombinant, chimeric virus or subviral particle capable of generating an immune response directed against the human donor virus, including one or more specific human RSV subgroups or strains, while the bovine backbone confers an attenuated phenotype making the chimera a useful candidate for vaccine development. In one such exemplary embodiment, one or more human RSV glycoprotein genes F, SH, and/or G are added to or substituted within a partial or complete bovine genome or antigenome to yield an attenuated, infectious human-bovine chimera that elicits an anti-human RSV immune response in a susceptible host. In other "chimeric" embodiments gene position-shifted RSV incorporate a heterologous gene or genome segment encoding an immunogenic protein, protein domain or epitope from multiple human RSV strains, for example two F or G proteins or immunogenic portions thereof from both RSV subgroups A and B. In yet additional alternate embodiments a gene position-shifted RSV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human RSV F, SH or G glycoprotein may be joined with a genome segment encoding corresponding bovine F, SH or G glycoprotein cytoplasmic and endodomains in the background bovine genome or antigenome.

According to the methods of the invention, human-bovine chimeric RSV may be constructed by substituting the heterologous gene or genome segment for a counterpart gene or genome segment in a partial RSV background genome or antigenome. Alternatively, the heterologous gene or genome segment may be added as a supernumerary gene or genome segment in combination with a complete (or partial if another gene or genome segment is deleted) RSV background genome or antigenome. For example, two human RSV G or F genes or genome segments can be included, one each from RSV subgroups A and B.

Often, displacement genes or genome segments (including heterologous genes or genome segments) are added at an intergenic position within a partial or complete RSV genome or antigenome. Alternatively, the gene or genome segment can be placed in other noncoding regions of the genome, for example, within the 5' or 3' noncoding regions or in other positions where noncoding nucleotides occur within the partial or complete genome or antigenome. In one aspect, noncoding regulatory regions contain cis-acting signals required for efficient replication, transcription, and translation, and therefore represent target sites for modification of these functions by introducing a displacement gene or genome segment or other mutation as disclosed herein. In more detailed aspects of the invention, attenuating mutations are introduced into cis-acting regulatory regions to yield, e.g., (1) a tissue specific attenuation (Gromeier et al., *J. Virol.* 73:958-64, 1999; Zimmermann et al., *J. Virol.* 71:4145-9, 1997), (2) increased sensitivity to interferon (Zimmermann et al., *J. Virol.* 71:4145-9, 1997), (3) temperature sensitivity (Whitehead et al., *Virology* 247:232-9, 1998), (4) a general restriction in level of replication (Men et al., *J. Virol.* 70:3930-7, 1996; Muster et al., *Proc. Natl. Acad. Sci. USA* 88:5177-5181, 1991), and/or (5) host specific restriction of replication (Cahour et al., *Virology* 207:68-76, 1995). These attenuating mutations can be achieved in various ways to produce an attenuated gene position-shifted RSV of the invention, for example by point mutations, exchanges of sequences between related viruses, or deletions.

In other alternative embodiments of the invention, gene position-shifted RSV are provided wherein the recombinant RSV is modified by deletion, insertion substitution, or rearrangement of a plurality of genes or genome segments. In certain embodiments selected "gene sets" are coordinately transferred by one of these means into, within, or from the recombinant RSV genome or antigenome. Exemplary RSV genes from which individual or coordinately transferred groups of genes may be selected include the RSV N, P, NS1, NS2, M2-1 and M genes, which may be transferred singly or in any combination in a human or bovine RSV genome or antigenome to yield an attenuated, gene-shifted derivative. In more detailed aspects, both N and P genes of a human or bovine RSV are deleted, inserted, substituted or rearranged coordinately (e.g., by coordinate deletion or substitution in a HRSV genome or antigenome by counterpart N and P genes from a bovine RSV). This coordinate gene transfer is facilitated by functional cooperativity between certain genes in the RSV genome, which often arises in the case of neighboring gene pairs in the genome. Thus, in other alternative embodiments, both NS1 and NS2 genes are coordinately transferred, e.g., by substitution in a human RSV by counterpart NS1 and NS2 genes from a bovine RSV. In yet additional embodiments, two or more of the M2-1, M2-2 and L genes of a RSV are coordinately transferred. For certain vaccine candidates within the invention for which a high level of host-range restriction is desired, each of the N, P, NS1, NS2, M2-1 and M genes of a human RSV are replaced by counterpart N, P, NS1, NS2, M2-1 and M genes from a bovine RSV.

Coordinate gene transfers within human-bovine chimeric RSV are also directed to introduction of human antigenic genes within a bovine background genome or antigenome. In certain embodiments, one or more human RSV envelope-associated genes selected from F, G, SH, and M is/are added or substituted within a partial or complete bovine RSV background genome or antigenome. For example, one or more human RSV envelope-associated genes selected from F, G, SH, and M may be added or substituted within a partial bovine RSV background genome or antigenome in which one or more envelope-associated genes selected from F, G, SH, and M is/are deleted. In more detailed aspects, one or more genes from a gene set defined as human RSV envelope-associated genes F, G, and M are added within a partial bovine RSV background genome or antigenome in which envelope-associated genes F, G, SH, and M are deleted. An exemplary human-bovine chimeric RSV bearing these features describe in the examples below is rBRSV/A2-MGF.

In other aspects of the invention, insertion of heterologous nucleotide sequences into RSV vaccine candidates are employed separately to modulate the level of attenuation of candidate vaccine recombinants, e.g., for the upper respiratory tract. Thus, it is possible to insert nucleotide sequences into a rRSV that both direct the expression of a foreign protein and that attenuate the virus in an animal host, or to use nucleotide insertions separately to attenuate candidate vaccine viruses. General tools and methods for achieving these aspects of the invention are provided, e.g., in U.S. Provisional Patent Application Ser. No. 60/170,195, U.S. patent application Ser. No. 09/458,813, and U.S. patent application Ser. No. 09/459,062 (each incorporated herein by reference). In one exemplary embodiment of the invention thus provided, insertion of the measles HA ORF between a selected RSV gene junction will restrict viral replication in vivo. In these aspects of the invention, the selected gene insert may be relatively large (approximately 1900 nts or greater). In this context, size of the insert specifies a selectable level of attenuation of the resulting recombinant virus. Displacement sequences of various lengths derived from a heterologous virus, e.g., introduced as single gene units (GUs) and designed specifically to lack any significant ORF, reveal selectable attenuation effects due to increased genome length (i.e., versus expression of an additional mRNA). Other constructs in which inserts of similar sizes are introduced into a downstream noncoding region (NCR) of a RSV gene are also useful within the invention.

To define some of the rules that govern the effect of gene insertion on attenuation, gene units of varying lengths can be inserted into a wild type RSV backbone and the effects of gene unit length on attenuation examined. Gene unit insertions engineered to not contain a significant ORF permit evaluation of the effect of gene unit length independently of an effect of the expressed protein of that gene. These heterologous sequences were inserted in a PIV backbone as an extra gene unit of sizes between 168 nt and 3918 nt between the HN and L genes. In addition, control cDNA constructions and viruses were made in which insertions of similar sizes were placed in the 3'-noncoding region of the HN gene of PIV and hence did not involve the addition of an extra gene. These viruses were made to assess the effect of an increase in the overall genome length and in gene number on attenuation. The insertion of an extra gene unit is expected to decrease the transcription of genes downstream of the insertion site which will affect both the overall abundance and ratios of the expressed proteins. As demonstrated herein, gene insertions or extensions larger than about 3000 nts in length attenuated the wild type virus for the upper and lower respiratory tract of hamsters. Gene insertions of about 2000 nts in length further attenuated the rHPIV3cp45L vaccine candidate for the upper respiratory tract. Comparable gene insertions in RSV thus can have the dual effect of both attenuating a candidate vaccine virus and inducing a protective effect against a second virus. Gene extensions in the 3'-noncoding region of a gene, which cannot express additional proteins, can also be attenuating in and of themselves. Within these methods of the invention, gene insertion length is a determinant of attenuation.

A separate example of gene order rearrangement for use within the invention involves changing the position of one or more naturally-occurring genes relative to other naturally-occurring genes, without the introduction or deletion of substantial lengths of polynucleotides (e.g., greater than 100 nucleotides). For example, the F and G genes of a human or human-bovine chimeric RSV can be shifted from their natural gene order position to a more promotor proximal position by excision and reinsertion of the genes into the recombinant genome or antigenome, without substantially altering the length of the recombinant RSV genome or antigenome.

These modifications in gene position and/or gene order typically result in viruses with altered biological properties. For example, recombinant RSV of the invention lacking one or more selected genes, for example NS1, NS2, SH, or G, NS1 and NS2 together, and SH and G together, may be attenuated in vitro, in vivo, or both. Whereas this phenotype is likely attributable primarily to the loss of expression of specific viral protein, it is also likely that the altered gene map contributed to the phenotype. This is supported by the results observed with the SH-deletion virus, which grew more efficiently than wild type in some cell types—probably due to an increase in the efficiency of transcription, replication or both resulting from the gene deletion and resulting change in gene order and possibly genome size.

The ability to generate infectious RSV from cDNA provides a method for introducing predetermined changes into infectious virus via the cDNA intermediate. This method has been used to produce a series of infectious attenuated derivatives of wild type recombinant RSV strain A2 that contain attenuating mutations including, for example, one or more nucleotide substitutions in cis-acting RNA signals and/or one or more amino acid substitutions in one or more viral proteins and/or deletion of one or more genes or ablation its/their expression (Bukreyev et al., *J. Virol.* 71:8973-8982, 1997; Whitehead et al., *J. Virol.* 72:4467-4471, 1998; Whitehead et al., *Virology* 247:232-239, 1998; Bermingham and Collins, *Proc. Natl. Acad. Sci. USA* 96:11259-11264, 1999; Juhasz et al., *Vaccine* 17:1416-1424, 1999; Juhasz et al., *J. Virol.* 73:5176-5180, 1999; Teng and Collins, *J. Virol.* 73:466-473, 1999; Whitehead et al., *J. Virol.* 73:871-877, 1999; Whitehead et al., *J. Virol.* 73:3438-3442, 1999; Collins et al., *Adv. Virus Res.* 54:423-451, 1999; U.S. Provisional Patent Application 60/143,097, filed Jul. 9, 1999, U.S. patent application Ser. No. 09/611,829 and its corresponding PCT application published as WO 01/04321; each incorporated herein by reference).

Strain A2 represents antigenic subgroup A, and an effective RSV vaccine also should represent the other antigenic subgroup, subgroup B. The G and F glycoproteins are the major antigenic determinants and the major protective RSV antigens (Connors et al., *J. Virol.* 65:1634-1637, 1991; Murphy et al., *Virus Research* 32:13-36, 1994; Collins et al., *Fields Virology* 2:1313-1352, 1996, and Crowe et al., *New Generation Vaccines,* 711-725, 1997; each incorporated herein by reference). Therefore, the G and F genes of recombinant strain A2 were replaced with their counterparts from the B1 strain of antigenic subgroup B (Whitehead et al., *J. Virol.* 73:9773-9780, 1999, incorporated herein by reference). This was done using wild type and attenuated strain. A2 backbones. Recombinant virus was obtained, and the "chimerization" did not detectably interfere with virus replication. This demonstrated an expedited method for making vaccine virus: specifically, to use attenuated strain A2 backbones to express the antigenic determinants of subgroup B (pending application). Thus, once an appropriately-attenuated subgroup A gene position-shifted RSV vaccine virus is identified in clinical trials, its backbone can be modified to produce a comparable subgroup B vaccine in an expedited manner, and the two viruses can be combined to make a bivalent vaccine.

It has also been demonstrated in the above-incorporated references that RSV useful within the invention can express a foreign gene added as an extra, supernumerary gene placed at any of a variety of genomic locations, preferably in an intergenic region. This concept has been used to make a recombinant strain A2 virus that also expressed the G glycoprotein of subgroup B as a supernumerary gene. Thus, a single virus expressed antigenic determinants of the two subgroups. Another example incorporated herein involves the expression of interferon gamma as an added gene, which resulted in attenuation without a reduction in immunogenicity, and also provided a method to reduce the relative level of stimulation of T helper lymphocyte subset 2, which has been proposed to mediate immunopathogenic responses to RSV (see, e.g., U.S. Provisional Application No. 60/143,425, filed Jul. 13, 1999, U.S. patent application Ser. No. 09/614,285 and its corresponding PCT application published as WO 01/04271, each incorporated herein by reference).

In alternate embodiments of the invention, a different basis for attenuation of a live virus vaccine incorporating a gene positional shift is provided, which attenuation is based in part on host range effects. In this regard, the instant disclosure provides attenuated, chimeric RSV by the introduction of genome segments, entire genes or multiple genes between HRSV and BRSV. Host range differences between HRSV and BRSV are exemplified by the highly permissive growth of HRSV in chimpanzees compared to the barely detectable or undetectable growth of BRSV in the same animal. The chimpanzee is a widely accepted model of RSV infection and immunogenic activity in humans, exhibiting virus replication and disease comparable to that of humans. As illustrated herein below, host range differences of chimeric RSV observed in chimpanzees are correlated with host range differences observed in cell culture, providing a convenient preliminary assay.

Host range effects observed in chimeric, human-bovine RSV of the invention are generally related to nucleotide and amino acid sequence differences observed between HRSV and BRSV. For example, the percent amino acid identity between HRSV and BRSV for each of the following proteins is: NS1 (69%), NS2 (84%), N (93%), P (81%), M (89%), SH (38%), G (30%), F (81%), M2-1 (80%), L (77%). Because of the extensive genetic divergence between HRSV and BRSV (replacement of the N gene of HRSV with that of BRSV, for example, involves approximately 26 amino acid differences), chimeric bovine-human RSV of the invention are particularly useful vaccine candidates. As exemplified herein below, replacement of the BRSV G and F glycoproteins with those of HRSV increases the permissivity of recombinant BRSV for replication in chimpanzees. The involvement of multiple genes and genome segments each conferring multiple amino acid or nucleotide differences provides a broad basis for attenuation which is highly stable to reversion. This mode of attenuation contrasts sharply to HRSV viruses attenuated by one or several point mutations, where reversion of an individual mutation will yield a significant or complete reacquisition of virulence. In addition, known attenuating point mutations in HRSV typically yield a temperature sensitive phenotype. This is because the temperature sensitive phenotype was specifically used as the first screen to identify altered progeny following exposure of HRSV to mutagens. One problem with attenuation associated with temperature sensitivity is that the virus can be overly restricted for replication in the lower respiratory tract while being under attenuated in the upper respiratory tract. This is because there is a temperature gradient within the respiratory tract, with temperature being higher (and more restrictive) in the lower respiratory tract and lower (less restrictive) in the upper respiratory tract. The ability of an attenuated virus to replicate in the upper respiratory tract can result in complications including congestion, rhinitis, fever and otitis media. Thus, attenuation achieved solely by temperature sensitive mutations may not be ideal. In contrast, host range mutations present in gene position-shifted RSV of the invention will not in most cases confer temperature sensitivity. Therefore, this novel method of attenuation will (i) be more stable genetically and phenotypically, and (ii) be less likely to be associated with residual virulence in the upper respiratory tract than other live vaccine approaches.

The amount of sequence divergence between BRSV and HRSV is about twice as much as between the HRSV A and B subgroups noted above. Thus, the F proteins have approximately 20% amino acid divergence between BRSV and HRSV, and the G proteins approximately 70% divergence (Lerch, et al., *J. Virol.* 64:5559-69, 1990; Lerch, et al., *Virology* 181:118-31, 1991; Mallipeddi and Samal, *J. Gen. Virol.* 74:2001-4, 1993; Mallipeddi and Samal, *Vet. Microbiol.* 36:359-67, 1993; Samal et al., *Virology* 180:453456, 1991; Samal and Zamora, *J. Gen. Virol.* 72:1717-1720, 1991; Zamora and Samal, *Virus Res.* 24:115-121, 1992; ibid, *J. Gen. Virol.* 73:737-741, 1992; Mallipeddi and Samal, *J. Gen. Virol.* 73:2441-2444, 1992, Pastey and Samal, *J. Gen. Virol.* 76:193-197, 1995; Walravens et al., *J. Gen. Virol.* 71:3009-3014, 1990; Yunnus et al., *J. Gen. Virol.* 79:2231-2238, 1998, each incorporated herein by reference).

In the prior disclosures incorporated herein, recombinant BRSV was modified to replace the G and F BRSV genes with their human RSV counterparts. The resulting chimeric BRSV/HRSV virus, bearing the antigenic determinants of human RSV on the BRSV backbone, replicated more efficiently in chimpanzees than did its BRSV parent, but remained highly attenuated. This indicated that the G and P genes contributed to the host range restriction of BRSV, but showed that one or more other genes also specified the host range restriction. This represents a starting point for constructing an optimal BRSV/HRSV chimeric virus that features a gene positional change as described above and which contains the human RSV G and F antigenic determinants, wherein the resulting recombinant RSV is attenuated by the presence of one or more BRSV genes to confer a host range restriction (Buchholz et al., *J. Virol.* 74:1187-1199, 2000; U.S. Patent Application No. 60/143,132, filed Jul. 9, 1999; each incorporated herein by reference).

Detailed descriptions of the materials and methods for producing recombinant RSV from cDNA, and for making and testing the full range of mutations and nucleotide modifications disclosed herein as supplemental aspects of the present invention, are set forth in, e.g., U.S. Provisional Patent Application No. 60/007,083, filed Sep. 27, 1995; U.S. patent application Ser. No. 08/720,132, filed Sep. 27, 1996; U.S. Provisional Patent Application No. 60/021,773, filed Jul. 15, 1996 and U.S. patent application Ser. No. 08/892,403, now issued as U.S. Pat. No. 5,993,824; U.S. Provisional Patent Application No. 60/046,141, filed May 9, 1997; U.S. Provisional Patent Application No. 60/047,634, filed May 23, 1997; U.S. Pat. No. 5,993,824, issued Nov. 30, 1999 (corresponding to International Publication No. WO 98/02530); U.S. patent application Ser. No. 09/291,894, filed by Collins et al. on Apr. 13, 1999 and corresponding to published PCT application WO 00/61737; U.S. Provisional Patent Application No. 60/129,006, filed by Murphy et al. on Apr. 13, 1999; Crowe et al., Vaccine 12: 691-699, 1994; and Crowe et al., Vaccine 12: 783-790, 1994; Collins, et al., Proc Nat. Acad. Sci. USA 92:11563-11567, 1995; Bukreyev, et al., J Virol 70:6634-41, 1996, Juhasz et al., J. Virol. 71(8):5814-5819, 1997; Durbin et al., Virology 235:323-332, 1997; Karron et al., J. Infect. Dis. 176:1428-1436, 1997; He et al. Virology 237:249-260, 1997; Baron et al. J. Virol. 71:1265-1271, 1997; Whitehead et al., Virology 247(2):232-9, 1998a; Whitehead et al., J. Virol. 72(5):4467-4471, 1998b; Jin et al. Virology 251: 206-214, 1998; Bukreyev, et al., Proc. Nat. Acad. Sci. USA 96:2367-2372, 1999; Bermingham and Collins, Proc. Natl. Acad. Sci. USA 96:11259-11264, 1999 Juhasz et al., Vaccine 17:1416-1424, 1999; Juhasz et al., J. Virol. 73:5176-5180, 1999; Teng and Collins, J. Virol. 73:466473, 1999; Whitehead et al., J. Virol. 73:9773-9780, 1999; Whitehead et al., J. Virol. 73:871-877, 1999; and Whitehead et al., J. Virol. 73:3438-3442, 1999.

Exemplary methods for producing recombinant RSV from cDNA involve intracellular coexpression, typically from plasmids cotransfected into tissue culture cells, of an RSV antigenomic RNA and the RSV N, P, M2-1 and L proteins. This launches a productive infection that results in the production of infectious cDNA-derived virus, which is termed recombinant virus. Once generated, recombinant RSV is readily propagated in the same manner as biologically-derived virus, and a recombinant virus and a counterpart biologically-derived virus cannot be distinguished unless the former had been modified to contain one or more introduced changes as markers.

In more detailed aspects, the foregoing incorporated documents describe methods and procedures useful within the invention for mutagenizing, isolating and characterizing RSV to obtain attenuated mutant strains (e.g., temperature sensitive (ts), cold passaged (cp) cold-adapted (ca), small plaque (sp) and host-range restricted (hr) mutant strains) and for identifying the genetic changes that specify the attenuated phenotype. In conjunction with these methods, the foregoing documents detail procedures for determining replication, immunogenicity, genetic stability and protective efficacy of biologically derived and recombinantly produced attenuated human RSV, including human RSV A and B subgroups, in accepted model systems, including murine and non-human primate model systems. In addition, these documents describe general methods for developing and testing immunogenic compositions, including monovalent and bivalent vaccines, for prophylaxis and treatment of RSV infection.

The ability to generate infectious RSV from cDNA provides a method for introducing predetermined changes into infectious virus via the cDNA intermediate. This method has been demonstrated to produce a wide range of infectious, attenuated derivatives of RSV, for example recombinant vaccine candidates containing one or more amino acid substitutions in a viral protein, deletion of one or more genes or ablation of gene expression, and/or one or more nucleotide substitutions in cis-acting RNA signals yielding desired effects on viral phenotype (see, e.g., Bukreyev et al., J. Virol. 71:8973-8982, 1997; Whitehead et al., J. Virol. 72:44674471, 1998; Whitehead et al., Virology 247:232-239, 1998; Bermingham and Collins, Proc. Natl. Acad. Sci. USA 96:11259-11264, 1999; Juhasz et al., Vaccine 17:1416-1424, 1999; Juhasz et al., J. Virol. 73:5176-5180, 1999; Teng and Collins, J. Virol. 73:466-473, 1999; Whitehead et al., J. Virol. 73:871-877, 1999; Whitehead et al., J. Virol. 73:3438-3442, 1999; and Collins et al., Adv. Virus Res. 54:423-451, 1999, each incorporated herein by reference).

Exemplary of the foregoing teachings are methods for constructing and evaluating infectious recombinant RSV modified to incorporate phenotype-specific mutations identified in biologically-derived RSV mutants, e.g., cp and ts mutations adopted in recombinant RSV from biologically derived designated cpts RSV 248 (ATCC VR 2450), cpts RSV 248/404 (ATCC VR 2454), cpts RSV 248/955 (ATCC VR 2453), opts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). These methods are readily adapted for construction of recombinant gene position-shifted RSV of the invention. The recombinant RSV thus provided may incorporate two or more ts mutations from the same, or different, biologically derived RSV mutant(s), for example one or more of the 248/404, 248/955, 530/1009, or 530/1030 biological mutants. In the latter context, multiply attenuated recombinants may have a combination of attenuating mutations from two, three or more biological mutants, e.g., a combination of attenuating mutations from the RSV mutants 530/1009/404, 248/404/1009, 248/404/1030, or 248/404/1009/1030 mutants. In exemplary embodiments, one or more attenuating mutations specify a temperature-sensitive substitution at amino acid Asn43, Phe521, Gln831, Met1169, or Tyr1321 in the RSV polymerase gene or a temperature-sensitive nucleotide substitution in the gene-start sequence of gene M2. Preferably, these mutations involve identical or conservative changes with the following changes identified in biologically derived mutant RSV, for example changes conservative to the following substitutions identified in the L polymerase gene: Ile for Asn43, Leu for Phe521, Leu for Gln831, Val for Met1169, and Asn for Tyr1321.

Yet additional mutations that may be incorporated in gene position-shifted RSV of the invention are mutations, e.g., attenuating mutations, identified in heterologous RSV or more distantly related negative stranded RNA viruses. In particular, attenuating and other desired mutations identified in one negative stranded RNA virus may be "transferred", e.g., copied, to a corresponding position within a human or bovine RSV genome or antigenome, either within the gene position-shifted RSV or as a means of constructing the gene position-shifted RSV. Briefly, desired mutations in one heterologous negative stranded RNA virus are transferred to the RSV recipient (e.g., bovine or human RSV, respectively). This involves mapping the mutation in the heterologous virus, thus identifying by sequence alignment the corresponding site in human or bovine RSV, and mutating the native sequence in the RSV recipient to the mutant genotype (either by an identical or conservative mutation), as described in U.S. Provisional Patent Application No. 60/129,006, filed by Murphy et al. on Apr. 13, 1999, incorporated herein by reference.

As this disclosure teaches, it is preferable to modify the chimeric genome or antigenome to encode an alteration at the subject site of mutation that corresponds conservatively to the alteration identified in the heterologous mutant virus. For example, if an amino acid substitution marks a site of mutation in the mutant virus compared to the corresponding wild-type sequence, then a similar substitution should be engineered at the corresponding residue(s) in the recombinant virus. Preferably the substitution will involve an identical or conservative amino acid to the substitute residue present in the mutant viral protein. However, it is also possible to alter the native amino acid residue at the site of mutation non-conservatively with respect to the substitute residue in the mutant protein (e.g., by using any other amino acid to disrupt or impair the function of the wild-type residue). Negative stranded RNA viruses from which exemplary mutations are identified and transferred into a gene position-shifted RSV of the invention include other RSVs (e.g., murine), PIV, Sendai virus (SeV), Newcastle disease virus (NDV), simian virus 5 (SV5), measles virus (MeV), rindepest virus, canine distemper virus (CDV), rabies virus (RaV) and vesicular stomatitis virus (VSV). A variety of exemplary mutations are disclosed, including but not limited to an amino acid substitution of phenylalanine at position 521 of the RSV L protein (corresponding to a substitution of phenylalanine at position 456 of the HPIV3 L protein). In the case of mutations marked by deletions or insertions, these can be introduced as corresponding deletions or insertions into the recombinant virus, however the particular size and amino acid sequence of the deleted or inserted protein fragment can vary.

A variety of additional types of mutations are also disclosed in the foregoing incorporated references and can be readily engineered into a recombinant gene position-shifted RSV of the invention to calibrate attenuation, immunogenicity or provide other advantageous structural and/or phenotypic effects. For example, restriction site markers are routinely introduced within the gene position-shifted genome or antigenome to facilitate cDNA construction and manipulation. Also described in the incorporated references are a wide range of nucleotide modifications other than point or site-specific mutations that are useful within the instant invention. For example, methods and compositions are disclosed for producing recombinant RSV expressing an additional foreign gene, e.g., a chloramphenicol acetyl transferase (CAT) or luciferase gene. Such recombinants generally exhibit reduced growth associated with the inserted gene. This attenuation appears to increase with increasing length of the inserted gene. The finding that insertion of a foreign gene into recombinant RSV reduces level of replication and is stable during passage in vitro provides another effective method for attenuating RSV for vaccine use. Similar or improved effects can thus be achieved by insertion of other desired genes, for example cytokines such as interferon-γ, interleukin-2, interleukin-4 and GM-CSF, among others.

Within the methods of the invention, additional genes or genome segments may be inserted into or proximate to the gene position-shifted RSV genome or antigenome. These genes may be under common control with recipient genes, or may be under the control of an independent set of transcription signals. Genes of interest include the RSV genes identified above, as well as non-RSV genes. Non-RSV genes of interest include those encoding cytokines (e.g., IL-2 through IL-18, especially IL-2, IL-6 and IL-12, IL-18, etc.), gamma-interferon, and proteins rich in T helper cell epitopes. These additional proteins can be expressed either as a separate protein, or as a chimera engineered from a second copy of one of the RSV proteins, such as SH. This provides the ability to modify and improve the immune responses against RSV both quantitatively and quantitatively.

Increased genome length results in attenuation of the resultant RSV, dependent in part upon the length of the insert. In addition, the expression of certain proteins, e.g. a cytokine, from a non-RSV gene inserted into gene position-shifted RSV will result in attenuation of the virus due to the action of the protein. Exemplary cytokines that yield an infectious, attenuated viral phenotype and high level cytokine expression from RSV transfected cells include interleukin-2 (IL-2), IL-4, GM-CSF, and γ-interferon. Additional effects including augmentation of cellular and or humoral immune responses will also attend introduction of cytokines into gene position-shifted RSV of the invention.

Deletions, insertions, substitutions and other mutations involving changes of whole viral genes or genome segments within gene position-shifted RSV of the invention yield highly stable vaccine candidates, which are particularly important in the case of immunosuppressed individuals. Many of these changes will result in attenuation of resultant vaccine strains, whereas others will specify different types of desired phenotypic changes. For example, accessory (i.e., not essential for in vitro growth) genes are excellent candidates to encode proteins that specifically interfere with host immunity (see, e.g., Kato et al., *EMBO. J.* 16:578-87, 1997, incorporated herein by reference). Ablation of such genes in chimeric vaccine viruses is expected to reduce virulence and pathogenesis and/or improve immunogenicity.

Additional, independent nucleotide modifications disclosed in the foregoing references for incorporation into recombinant gene position-shifted RSV of the invention include partial or complete deletion or ablation of a selected RSV gene. Thus, RSV genes or genome segments may be deleted, including partial or complete deletions of open reading frames and/or cis-acting regulatory sequences of the RSV NS1, NS2, N, P, M, G, F, SH, M2(ORF1), M2(ORF2) and/or L genes. In one example, a recombinant RSV was generated in which expression of the SH gene was been ablated by removal of a polynucleotide sequence encoding the SH mRNA and protein. Deletion of the SH gene yielded not only recoverable, infectious RSV, but one which exhibited substantially improved growth in tissue culture based on both yield of infectious virus and plaque size. This improved growth in tissue culture specified by the SH deletion provides useful tools for developing gene position-shifted RSV vaccines, for example by overcoming problems of poor RSV yields in culture. Moreover, these deletions are highly stable against genetic reversion, rendering RSV clones derived therefrom particularly useful as vaccine agents.

SH-minus RSV recombinants also exhibit site-specific attenuation in the upper respiratory tract of mice, which presents novel advantages for vaccine development. Current RSV strains under evaluation as live virus vaccines, for example cp mutants, do not exhibit significantly altered growth in tissue culture. These are host range mutations and they restrict replication in the respiratory tract of chimpanzees and humans approximately 100-fold in the lower respiratory tract. Another exemplary type of mutation, ts mutations, tend to preferentially restrict virus replication in the lower respiratory tract due to the gradient of increasing body temperature from the upper to the lower respiratory tract. In contrast to these cp and ts mutants, SH-minus RSV mutants have distinct phenotypes of greater restriction in the upper respiratory tract. This is particularly desirable for vaccine viruses for use in very young infants, because restriction of replication in the upper respiratory tract is required to ensure safe vaccine administration in this vulnerable age group whose members breathe predominantly through the nose. Further, in any age group, reduced replication in the upper respiratory tract will reduce morbidity from otitis media. In addition to these advantages, the nature of SH deletion mutations, involving e.g., nearly 400 nt and ablation of an entire mRNA, represents a type of mutation which will be highly refractory to reversion. The utility of the SH-minus deletion as a "displacement polynucleotide" for simultaneously directing a gene position-shift, e.g., to upregulate F and G glycoprotein gene expression, is amply evinced in the examples below.

Also discussed in the context of SH gene modifications is a comparison of SH genes among different RSVs, including human and bovine RSVs, and other pneumoviruses to provide additional tools and methods for generating useful RSV recombinant vaccines. For example, the two RSV antigenic subgroups, A and B, exhibit a relatively high degree of conservation in certain SH domains. In two such domains, the N-terminal region and putative membrane-spanning domains of RSV A and B display 84% identity at the amino acid level, while the C-terminal putative ectodomains are more divergent (approx. 50% identity). Comparison of the SH genes of two human RSV subgroup B strains, 8/60 and 18537, identified only a single amino acid difference (Anderson et al., supra). The SH proteins of human versus bovine RSV are approximately 40% identical, and share major structural features including (i) an asymmetric distribution of conserved residues; (ii) very similar hydrophobicity profiles; (iii) the presence of two N-linked glycosylation sites with one site being on each side of the hydrophobic region; and (iv) a single cysteine residue on the carboxyterminal side of the central hydrophobic region of each SH protein. (Anderson et al., supra). By evaluating these and other sequence similarities and differences, selections can be made of heterologous sequence(s) that can be substituted or inserted within infectious gene position-shifted RSV clones, for example to yield vaccines having multi-specific immunogenic effects or, alternatively or in addition, desirable effects such as attenuation.

In alternate embodiments of the invention, partial gene deletions or other limited nucleotide deletions are engineered into recombinant RSV to yield desired phenotypic changes. In one example, the length of the RSV genome is reduced by deleting sequence from the downstream noncoding region of the SH gene. This exemplary partial gene deletion was constructed using a version of the antigenome cDNA containing an XmaI site in the G-F intergenic region, a change which of itself would not be expected to affect the encoded virus. The encoded virus, designated RSV/6120, has silent nucleotide substitutions in the last three codons and termination codon of the SH ORF and has a deletion of 112 nucleotides from the SH downstream non-translated region (positions 44994610 in the recombinant antigenome). This deletion leaves the gene-end signal (Bukreyev, et al., *J. Virol.* 70:6634-41, 1996, incorporated herein by reference) intact. These point mutations and 112-nt deletion do not alter the encoded amino acids of any of the viral proteins, nor do they interrupt any of the known viral RNA signals or change the number of encoded mRNAs.

The 6120 virus was analyzed for the efficiency of multistep growth in parallel with its full-length counterpart, D53, and showed a peak titer that was reproducibly higher than that of the D53 virus by a factor of 1.5- to 2-fold. Thus, the small, partial deletion in the SH gene of a 112-nt noncoding sequence resulted in a substantial increase in growth efficiency in vitro.

Other partial gene deletions and small nucleotide deletions can be readily engineered in recombinant RSV of the invention to alter viral phenotype, including nucleotide deletions in: (1) nontranslated sequence at the beginning and/or end of the various ORFs apart from the cis-acting RNA signal, (2) intergenic regions, and (3) the regions of the 3'leader and 5' trailer that are not essential for promoter activity. Examples of nontranslated gene sequence for deletion or insertion include the following regions of the downstream untranslated region of the NS1, NS2, P, M, F, and M2 genes: namely, sequence positions 519-563, 1003-1086, 3073-3230, 4033-4197, 7387-7539 and 8433-8490, respectively, numbered according to the recombinant antigenome. Also, as additional examples, nt 55-96, nt 606-624, nt 4231 4300 can be deleted from the upstream nontranslated region of the NS1, NS2 and SH genes respectively. Any partial or complete deletion in one or more of these sequences can be achieved in accordance with the teachings herein to provide candidates that are readily screened for beneficial phenotypic changes specified by selected deletions. Additional nontranslated regions within the RSV genome are also useful in this regard. Since the gene-start and gene-end signals have been mapped and characterized with regard to important positions (Kuo, et al., *J. Virol.*, 71:49444953; 1997; Harmon, et al., *J. Virol.*, 75:36-44, 2001, each incorporated herein by reference), deletions or modifications that involve one or a few (e.g., 3-10, 10-20, 20-45) nt can be considered. In some cases, specific additional advantages may be obtained. For example, in the G gene, deletion of nt 4683 to 4685, which includes one nt of the gene-start signal and two nt of nontranslated sequence, ablates the first AUG in the mRNA, which does not initiate a significant ORF but is thought to divert ribosomes from the next AUG which initiates the G ORF. In addition, this deletion restores the GS signal and retains the translation start site of the G ORF. Thus, nontranslated sites for modification can be selected based on knowledge of the genome, or can be selected at random and tested expeditiously by the methods of the present invention.

With regard to intergenic sequences, studies with minigenomes show that an intergenic region can be reduced to a single nt or deleted altogether without affecting transcription and RNA replication. The intergenic regions of strain A2 represent another 207 nt in aggregate (noting that the NS2-N intergenic region of the recombinant antigenome was engineered to be 1 nt longer than its biological equivalent; see, e.g., Collins, et al., *Proc. Natl. Acad. Sci. USA*, 92:11563-11567, 1995, incorporated herein by reference).

The RSV 5' trailer region is 155 nt in length and thus is approximately 100 nt longer than the corresponding region of most mononegaviruses and is 11 nt longer than the RSV leader region. Studies with minigenomes suggest that much of this sequence is not essential and is a candidate for modification (Kuo, et al., *J. Virol.*, 70:6892-901, 1996, incorporated herein by reference). For example, the region of trailer that immediately follows the L gene could be reduced in size by 75 nt, 100 nt, 125 nt or more, leaving intact the 5' genomic terminus (which encodes the 3' end of the antigenome, including the antigenome promoter). Similarly, the 44-nt leader region might be modified. For example, the first 11 nt at the 3' leader end form the core of the viral promoter, and thus sequence from the remainder of the leader region might be deleted or otherwise modified.

In certain embodiments of the invention, deleting one or more of the nontranslated sequences (partially or completely) described above for the NS1, NS2, SH, F and M2 genes will result in an adjustable reduction in genome length of up to 806 nt—more than 7-fold greater than the 112-nt deletion described in the instant example. Deleting partially or completely one or more of the intergenic regions between the first nine genes (e.g., down to a minimal length of one nt each) would yield up to an additional 198 nt of adjustable deletion. Partial or complete deletions from the trailer and/or leader can yield up to 50, 75, 100, or more nt in additional deletion. Thus, for example, combining 806 nt from nontranslated gene sequence with 198 nt from the intergenic regions and 100 nt from the trailer yields 1104 nt in aggregate, representing nearly a 10-fold greater deletion than 112-nt deletion described here (and representing more than 7% of the RSV genome).

In another example described in the above-incorporated references, expression of the NS2 gene is ablated by introduction of stop codons into the translational open reading frame (ORF). The rate of release of infectious virus was reduced for this NS2 knock-out virus compared to wild-type. In addition, comparison of the plaques of the mutant and wild-type viruses showed that those of the NS2 knock-out were greatly reduced in size. This type of mutation can thus be incorporated within viable recombinant gene position-shifted RSV to yield altered phenotypes, in this case reduced rate of virus growth and reduced plaque size in vitro. These and other knock-out methods and mutants will therefore provide for yet additional recombinant RSV vaccine agents, based on the known correlation between reduced plaque size in vitro and attenuation in vivo. Expression of the NS2 gene also was ablated by complete removal of the NS2 gene, yielding a virus with a similar phenotype.

Other RSV genes which have been successfully deleted include the NS1 and M2-2 genes. The former was deleted by removal of the polynucleotide sequence encoding the respective protein, and the latter by introducing a frame-shift or altering translational start sites and introducing stop codons. Interestingly, recovered NS1-minus virus produce small plaques in tissue culture albeit not as small as those of the NS2 deletion virus. The fact that the NS1-minus virus can grow, albeit with reduced efficiency, identifies the NS1 protein as an accessory protein, one that is dispensable to virus growth. The plaque size of the NS1-minus virus was similar to that of NS2 knock-out virus in which expression of the NS2 protein was ablated by introducing translational stop codons into its coding sequence The small plaque phenotype is commonly associated with attenuating mutations. This type of mutation can thus be independently incorporated within viable recombinant RSV to yield altered phenotypes. These and other knock-out methods and mutants will therefore provide for yet additional recombinant gene position-shifted RSV vaccine agents, based on the known correlation between plaque size in vitro and attenuation in vivo. The NS2 knock-out mutant exhibited a moderately attenuated phenotype in the upper respiratory tract and a highly attenuated phenotype in the lower respiratory tract in naive chimpanzees. This mutant also elicited greatly reduced disease symptoms in chimps while stimulating significant resistance to challenge by the wild-type virus (Whitehead et al., *J. Virol.* 73:3438-3442, 1999, incorporated herein by reference).

Yet additional methods and compositions provided within the incorporated references and useful within the invention involve different nucleotide modifications within gene position-shifted RSV that alter cis-acting regulatory sequences within the chimeric genome or antigenome. For example, a translational start site for a secreted form of the RSV G glycoprotein can be deleted to disrupt expression of this form of the G glycoprotein The RSV G protein is synthesized in two forms: as an anchored type II integral membrane protein and as a N-terminally resected form which lacks essentially all of the membrane anchor and is secreted (Hendricks et al., *J. Virol.* 62:2228-2233, 1988). The two forms have been shown to be derived by translational initiation at two different start sites: the longer form initiates at the first AUG of the G ORF, and the second initiates at the second AUG of the ORF at codon 48 and is further processed by proteolysis (Roberts et al., *J. Virol.* 68: 4538-4546, 1994). The presence of this second start site is highly conserved, being present in all strains of human, bovine and ovine RSV sequenced to date. It has been suggested that the soluble form of the G protein might mitigate host immunity by acting as a decoy to trap neutralizing antibodies. Also, soluble G has been implicated in preferential stimulation of a Th2-biased response, which in turn appears to be associated with enhanced immunopathology upon subsequent exposure to RSV. With regard to an RSV vaccine virus, it is highly desirable to minimize antibody trapping or imbalanced stimulation of the immune system, and so it would be desirable to ablate expression of the secreted form of the G protein. This has been achieved in recombinant virus. Thus, this mutation is particularly useful to qualitatively and/or quantitatively alter the host immune response elicited by the recombinant virus, rather than to directly attenuate the virus.

The incorporated references also describe modulation of the phenotype of recombinant RSV by altering cis-acting transcription signals of exemplary genes, e.g., NS1 and NS2. The results of these nucleotide modifications are consistent with modification of gene expression by altering cis-regulatory elements, for example to decrease levels of readthrough mRNAs and increase expression of proteins from downstream genes. The resulting recombinant viruses will preferably exhibit increased growth kinetics and increased plaque size. Exemplary modifications to cis-acting regulatory sequences include modifications to gene end (GE) and gene start (GS) signals associated with RSV genes. In this context, exemplary changes include alterations of the GE signals of the NS1 and NS2 genes rendering these signals identical to the naturally-occurring GE signals of the RSV N gene. The resulting recombinant virus exhibits increased growth kinetics and plaque size and therefore provide yet additional means for beneficially modifying phenotypes of gene position-shifted RSV vaccine candidates.

Methods and compositions provided in the above-incorporated references also allow production of attenuated gene position-shifted RSV vaccine viruses comprising sequences from both RSV subgroups A and B, e.g., to yield a RSV A or B vaccine or a bivalent RSV A/B vaccine (see, e.g., U.S. patent application Ser. No. 09/291,894, filed by Collins et al. on Apr. 13, 1999, incorporated herein by reference). Further augmenting the invention in this context, specific attenuating mutations have been incorporated into chimeric RSV A/B viruses include: (i) three of the five cp mutations, namely the mutation in N (V267I) and the two in L (C319Y and H1690Y), but not the two in F since these are removed by substitution with the B1 F gene; (ii) the 248 (Q831L), 1030 (Y1321N) and, optionally, 404-L (D1183E) mutations which have been identified in attenuated strain A2 viruses; (iii) the single nucleotide substitution at position 9 in the gene-start signal of the M2 gene, and (iv) deletion of the SH gene. Other immediately available mutations in gene position-shifted RSV carrying RSV A and or RSV B genes or genome segments include, but are not limited to, NS1, NS2, G, or M2-2' gene deletions, and the 530 and 1009 mutations, alone or in combination.

In other detailed aspects of the invention, gene position-shifted RSV are employed as "vectors" for protective antigens of heterologous pathogens, including other RSVs and non-RSV viruses and non-viral pathogens. Within these aspects, the gene position-shifted RSV genome or antigenome comprises a partial or complete RSV "vector genome or antigenome" combined with one or more heterologous genes or genome segments encoding one or more antigenic determinants of one or more heterologous pathogens (see, e.g., U.S. Provisional Patent Application Ser. No. 60/170,195; U.S. patent application Ser. No. 09/458,813; and U.S. patent application Ser. No. 09/459,062, each incorporated herein by reference). The heterologous pathogen in this context may be a heterologous RSV (e.g., a different RSV strain or subgroup) and the heterologous gene(s) or genome segment(s) can be selected to encode one or more of the above identified RSV proteins, as well as protein domains, fragments, and immunogenic regions or epitopes thereof. RSV vector vaccines thus constructed may elicit a polyspecific immune response and may be administered simultaneously or in a coordinate administration protocol with other vaccine agents.

Gene position-shifted RSV engineered as vectors for other pathogens may comprise a vector genome or antigenome that is a partial or complete HRSV genome or antigenome, which is combined with or is modified to incorporate one or more heterologous genes or genome segments encoding antigenic determinant(s) of one or more heterologous RSV(s), including heterologous HRSVs selected from HRSV A or HRSV B. In alternative aspects, the vector genome or antigenome is a partial or complete HRSV genome or antigenome and the heterologous gene(s) or genome segment(s) encoding the antigenic determinant(s) is/are of one or more non-RSV pathogens. The vector genome or antigenome may further incorporate one or more gene(s) or genome segment(s) of a BRSV that specifies attenuation. Alternatively, the vector virus may be comprise a partial or complete BRSV background genome or antigenome incorporating one or more HRSV genes or genome segments, wherein the gene position-shifted RSV vector virus is modified to include one or more donor gene(s) or genome segment(s) encoding an antigenic determinant of a non-RSV pathogen.

Thus, in certain detailed aspects of the invention, gene position-shifted RSV are provided as vectors for a range of non-RSV pathogens (see, e.g., U.S. Provisional Patent Application Ser. No. 60/170,195; U.S. patent application Ser. No. 09/458,813; and U.S. patent application Ser. No. 09/459,062, each incorporated herein by reference). The vector genome or antigenome for use within these aspects of the invention may comprise a partial or complete BRSV or HRSV genome or antigenome incorporating, respectively, a heterologous HRSV or BRSV gene or genome segment, and the heterologous pathogen may be selected from measles virus, subgroup A and subgroup B respiratory syncytial viruses, HPIV1, HPIV2, BPIV3, mumps virus, human papilloma viruses, type 1 and type 2 human immunodeficiency viruses, herpes simplex viruses, cytomegalovirus, rabies virus, Epstein Barr virus, filoviruses, bunyaviruses, flaviviruses, alphaviruses and influenza viruses.

For example, a HRSV or BRSV vector genome or antigenome for constructing gene position-shifted RSV of the invention may incorporate heterologous antigenic determinant(s) selected from the measles virus HA and F proteins, or antigenic domains, fragments and epitopes thereof. In exemplary embodiments, a transcription unit comprising an open reading frame (ORF) of a measles virus HA gene is added to or incorporated within a BRSV or HRSV3 vector genome or antigenome. Alternatively gene position-shifted RSV of the invention may used as vectors to incorporate heterologous antigenic determinant(s) from a parainfluenza virus (P), for example by incorporating one or more genes or genome segments that encode(s) a HPIV1, HPIV2, or HPIV3 HN or F glycoprotein or immunogenic domain(s) or epitope(s) thereof.

The introduction of heterologous immunogenic proteins, domains and epitopes within gene position-shifted RSV is particularly useful to generate novel immune responses in an immunized host. For example, addition or substitution of an immunogenic gene or genome segment from one, donor RSV subgroup or strain within a recipient genome or antigenome of a different RSV subgroup or strain can generate an immune response directed against the donor subgroup or strain, the recipient subgroup or strain, or against both the donor and recipient subgroup or strain. To achieve this purpose, gene position-shifted RSV may also be constructed that express a chimeric protein, e.g., an immunogenic glycoprotein having a cytoplasmic tail and/or transmembrane domain specific to one RSV fused to an ectodomain of a different RSV to provide, e.g., a human-bovine fusion protein, or a fusion protein incorporating domains from two different human RSV subgroups or strains. In a preferred embodiment, a gene position-shifted RSV genome or antigenome encodes a chimeric glycoprotein in the recombinant virus or subviral particle having both human and bovine glycoprotein domains or immunogenic epitopes. For example, a heterologous genome segment encoding a glycoprotein ectodomain from a human RSV F, SH or G glycoprotein may be joined with a polynucleotide sequence (i.e., a genome segment) encoding the corresponding bovine F, SH or G glycoprotein cytoplasmic and endo domains to form the gene position-shifted RSV genome or antigenome.

In other embodiments, gene position-shifted RSV useful in a vaccine formulation can be conveniently modified to accommodate antigenic drift in circulating virus. Typically the modification will be in the G and/or F proteins. An entire G or F gene, or a genome segment encoding a particular immunogenic region thereof, from one RSV strain is incorporated into a gene position-shifted RSV genome or antigenome cDNA by replacement of a corresponding region in a recipient clone of a different RSV strain or subgroup, or by adding one or more copies of the gene, such that several antigenic forms are represented. Progeny virus produced from the modified RSV clone can then be used in vaccination protocols against emerging RSV strains.

A variety of additional embodiments of the invention involve the addition or substitution of only a portion of a donor gene of interest to the recipient gene position-shifted RSV genome or antigenome. Commonly, non-coding nucleotides such as cis-acting regulatory elements and intergenic sequences need not be transferred with the donor gene coding region. Thus, a coding sequence (e.g., a partial or complete open reading frame (ORF)) of a particular gene may be added or substituted to the partial or complete background genome or antigenome under control of a heterologous promoter (e.g., a promoter existing in the background genome or antigenome) of a counterpart gene or different gene as compared to the donor sequence. A variety of additional genome segments provide useful donor polynucleotides for inclusion within a chimeric genome or antigenome to express gene position-shifted RSV having novel and useful properties. For example, heterologous genome segments may encode part or all of a glycoprotein cytoplasmic tail region, transmembrane domain or ectodomain, an epitopic site or region, a binding site or region containing a binding site, an active site or region containing an active site, etc., of a selected protein from a human or bovine RSV. These and other genome segments can be added to a complete background genome or antigenome or substituted therein for a counterpart genome segment to yield novel chimeric RSV recombinants. Certain recombinants will express a chimeric protein, e.g., a protein having a cytoplasmic tail and/or transmembrane domain of one RSV fused to an ectodomain of another RSV.

Genes and genome segments for use within the gene position-shifted RSV of the invention embrace an assemblage of alternate polynucleotides having a range of size and sequence variation. Useful genome segments in this regard range from about 15-35 nucleotides in the case of genome segments encoding small functional domains of proteins, e.g., epitopic sites, to about 50, 75, 100, 200-500, and 500-1,500 or more nucleotides for genome segments encoding larger domains or protein regions. Selection of counterpart genes and genome segments relies on sequence identity or linear correspondence in the genome between the subject counterparts. In this context, a selected human or bovine polynucleotide "reference sequence" is defined as a sequence or portion thereof present in either the donor or recipient genome or antigenome. This reference sequence is used as a defined sequence to provide a rationale basis for sequence comparison with the counterpart heterologous sequence. For example, the reference sequence may be a defined a segment of a cDNA or gene, or a complete cDNA or gene sequence. Generally, a reference sequence for use in defining counterpart genes and genome segments is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of (Smith & Waterman, *Adv. Appl. Math.* 2:482, 1981), by the homology alignment algorithm of (Needleman & Wunsch, *J. Mol. Biol.* 48:443, 1970), by the search for similarity method of (Pearson & Lipman, *Proc. Natl. Acad. Sci. USA* 85:2444, 1988) (each of which is incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity.

Corresponding residue positions, e.g., two different human RSVs or between a bovine and human RSV, may be divergent, identical or may differ by conservative amino acid substitutions. Conservative amino acid substitutions refer to the interchangeability of residues having similar side chains. For example, a conservative group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, ω-N-methylarginine, and other amino and imino acids (e.g., 4-hydroxyproline). Moreover, amino acids may be modified by glycosylation, phosphorylation and the like.

The present invention employs cDNA-based methods to construct a variety of recombinant, gene position-shifted RSV viruses and subviral particles. These recombinant RSV offer improved characteristics of attenuation and immunogenicity for use as vaccine agents. Desired phenotypic changes that are engineered into gene position-shifted RSV include, but are not limited to, attenuation in culture or in a selected host environment, resistance to reversion from the attenuated phenotype, enhanced immunogenic characteristics (e.g., as determined by enhancement, or diminution, of an elicited immune response), upregulation or downregulation of transcription and/or translation of selected viral products, etc. In preferred aspects of the invention, attenuated, gene position-shifted RSV are produced in which the chimeric genome or antigenome is further modified by introducing one or more attenuating mutations specifying an attenuating phenotype. These mutations may be generated de novo and tested for attenuating effects according to a rational design mutagenesis strategy as described in the above-incorporated references. Alternatively, the attenuating mutations can be identified in a biologically derived mutant RSV and thereafter incorporated into the gene position-shifted RSV of the invention.

Attenuating mutations in biologically derived RSV for incorporation within a gene position-shifted RSV vaccine strain may occur naturally or may be introduced into wild-type RSV strains by well known mutagenesis procedures. For example, incompletely attenuated parental RSV strains can be produced by chemical mutagenesis during virus growth in cell cultures to which a chemical mutagen has been added, by selection of virus that has been subjected to passage at suboptimal temperatures in order to introduce growth restriction mutations, or by selection of a mutagenized virus that produces small plaques (sp) in cell culture, as generally described herein and in U.S. Pat. No. 5,922,326, issued Jul. 13, 1999, incorporated herein by reference.

By "biologically derived RSV" is meant any RSV not produced by recombinant means. Thus, biologically derived RSV include naturally occurring RSV of all subgroups and strains, including, e.g., naturally occurring RSV having a wild-type genomic sequence and RSV having genomic variations from a reference wild-type RSV sequence, e.g., RSV having a mutation specifying an attenuated phenotype. Likewise, biologically derived RSV include RSV mutants derived from a parental RSV strain by, inter alia, artificial mutagenesis and selection procedures.

To produce a satisfactorily attenuated RSV from biologically derived strains, mutations are preferably introduced into a parental strain which has been incompletely or partially attenuated, such as the well known ts-1 or ts-1NG or cpRSV mutants of the A2 strain of RSV subgroup A, or derivatives or subclones thereof. Using these and other partially attenuated strains additional mutation(s) can be generated that further attenuate the strain, e.g., to a desired level of restricted replication in a mammalian host, while retaining sufficient immunogenicity to confer protection in vaccinees.

Partially attenuated mutants of the subgroup A or B virus can be produced by well known methods of biologically cloning wild-type virus in an acceptable cell substrate and developing, e.g., cold-passaged mutants thereof, subjecting the virus to chemical mutagenesis to produce ts mutants, or selecting small plaque or similar phenotypic mutants (see, e.g., Murphy et al., International Publication WO 93/21310, incorporated herein by reference). For virus of subgroup B, an exemplary, partially attenuated parental virus is cp 23, which is a mutant of the B1 strain of subgroup B.

Various known selection techniques may be combined to produce partially attenuated mutants from non-attenuated subgroup A or B strains which are useful for further derivatization as described herein. Further, mutations specifying attenuated phenotypes may be introduced individually or in combination in incompletely attenuated subgroup A or B virus to produce vaccine virus having multiple, defined attenuating mutations that confer a desired level of attenuation and immunogenicity in vaccinees.

As noted above, production of a sufficiently attenuated biologically derived RSV mutant can be accomplished by several known methods. One such procedure involves subjecting a partially attenuated virus to passage in cell culture at progressively lower, attenuating temperatures. For example, whereas wild-type virus is typically cultivated at about 34-37° C., the partially attenuated mutants are produced by passage in cell cultures (e.g., primary bovine kidney cells) at suboptimal temperatures, e.g., 20-26° C. Thus, the cp mutant or other partially attenuated strain, e.g., ts-1 or spRSV, is adapted to efficient growth at a lower temperature by passage in MRC-5 or Vero cells, down to a temperature of about 20-24° C., preferably 20-22° C. This selection of mutant RSV during cold-passage substantially reduces any residual virulence in the derivative strains as compared to the partially attenuated parent.

Alternatively, specific mutations can be introduced into biologically derived RSV by subjecting a partially attenuated parent virus to chemical mutagenesis, e.g., to introduce ts mutations or, in the case of viruses which are already ts, additional ts mutations sufficient to confer increased attenuation and/or stability of the ts phenotype of the attenuated derivative. Means for the introduction of ts mutations into RSV include replication of the virus in the presence of a mutagen such as 5-fluorouridine or 5-fluorouracil in a concentration of about $10^{-3}$ to $10^{-5}$ M, preferably about $10^{-4}$ M, exposure of virus to nitrosoguanidine at a concentration of about 100 µg/ml, according to the general procedure described in, e.g., (Gharpure et al., J. Virol. 3:414-421, 1969 and Richardson et al., J. Med. Virol. 3:91-100, 1978), or genetic introduction of specific ts mutations. Other chemical mutagens can also be used. Attenuation can result from a ts mutation in almost any RSV gene, although a particularly amenable target for this purpose has been found to be the polymerase (L) gene.

The level of temperature sensitivity of replication in exemplary attenuated RSV for use within the invention is determined by comparing its replication at a permissive temperature with that at several restrictive temperatures. The lowest temperature at which the replication of the virus is reduced 100-fold or more in comparison with its replication at the permissive temperature is termed the shutoff temperature. In experimental animals and humans, both the replication and virulence of RSV correlate with the mutant's shutoff temperature. Replication of mutants with a shutoff temperature of 39° C. is moderately restricted, whereas mutants with a shutoff of 38° C. replicate less well and symptoms of illness are mainly restricted to the upper respiratory tract. A virus with a shutoff temperature of 35° C. to 37° C. will typically be fully attenuated in chimpanzees and substantially attenuated in humans. Thus, attenuated biologically derived mutant and gene position-shifted RSV of the invention which are ts will have a shutoff temperature in the range of about 35° C. to 39° C., and preferably from 35° C. to 38° C. The addition of a ts mutation into a partially attenuated strain produces a multiply attenuated virus useful within vaccine compositions of the invention.

A number of attenuated RSV strains as candidate vaccines for intranasal administration have been developed using multiple rounds of chemical mutagenesis to introduce multiple mutations into a virus which had already been attenuated during cold-passage (e.g., Connors et al., Virology 208: 478-484, 1995; Crowe et al., Vaccine 12: 691-699, 1994; and Crowe et al., Vaccine 12: 783-790, 1994, incorporated herein by reference). Evaluation in rodents, chimpanzees, adults and infants indicate that certain of these candidate vaccine strains are relatively stable genetically, are highly immunogenic, and may be satisfactorily attenuated. Nucleotide sequence analysis of some of these attenuated viruses indicates that each level of increased attenuation is associated with specific nucleotide and amino acid substitutions. The above-incorporated references also disclose how to routinely distinguish between silent incidental mutations and those responsible for phenotype differences by introducing the mutations, separately and in various combinations, into the genome or antigenome of infectious RSV clones. This process coupled with evaluation of phenotype characteristics of parental and derivative virus identifies mutations responsible for such desired characteristics as attenuation, temperature sensitivity, cold-adaptation, small plaque size, host range restriction, etc.

Mutations thus identified are compiled into a "menu" and are then introduced as desired, singly or in combination, to calibrate a gene position-shifted RSV vaccine virus to an appropriate level of attenuation, immunogenicity, genetic resistance to reversion from an attenuated phenotype, etc., as desired. Preferably, the chimeric RSV of the invention are attenuated by incorporation of at least one, and more preferably two or more, attenuating mutations identified from such a menu, which may be defined as a group of known mutations within a panel of biologically derived mutant RSV strains. Preferred panels of mutant RSV strains described herein are cold passaged (cp) and/or temperature sensitive (ts) mutants, for example a panel comprised of RSV mutants designated cpts RSV 248 (ATCC VR 2450), cpts RSV 248/404 (ATCC VR 2454), cpts RSV 2481955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579) (each deposited under the terms of the Budapest Treaty with the American Type Culture Collection (ATCC) of 10801 University Boulevard, Manassas, Va. 20110-2209, U.S.A., and granted the above identified accession numbers).

From this exemplary panel of biologically derived mutants, a large menu of attenuating mutations are provided which can each be combined with any other mutation(s) within the panel for calibrating the level of attenuation in a recombinant, gene position-shifted RSV for vaccine use. Additional mutations may be derived from RSV having non-ts and non-cp attenuating mutations as identified, e.g., in small plaque (sp), cold-adapted (ca) or host-range restricted (hr) mutant strains. Attenuating mutations may be selected in coding portions of a donor or recipient RSV gene or in non-coding regions such as a cis-regulatory sequence. For example, attenuating mutations may include single or multiple base changes in a gene start sequence, as exemplified by a single or multiple base substitution in the M2 gene start sequence at nucleotide 7605.

Gene position-shifted RSV designed and selected for vaccine use often have at least two and sometimes three or more attenuating mutations to achieve a satisfactory level of attenuation for broad clinical use. In one embodiment, at least one attenuating mutation occurs in the RSV polymerase gene (either in the donor or recipient gene) and involves a nucleotide substitution specifying an amino acid change in the polymerase protein specifying a temperature-sensitive (ts) phenotype. Exemplary gene position-shifted RSV in this context incorporate one or more nucleotide substitutions in the large polymerase gene L resulting in an amino acid change at amino acid Asn43, Phe521, Gln831, Met1169, or Tyr1321, as exemplified by the changes, Leu for Phe521, Leu for Gln831, Val for Met1169, and Asn for Tyr1321. Alternately or additionally, gene position-shifted RSV of the invention may incorporate a ts mutation in a different RSV gene, e.g., in the M2 gene. Preferably, two or more nucleotide changes are incorporated in a codon specifying an attenuating mutation, e.g., in a codon specifying a ts mutation, thereby decreasing the likelihood of reversion from an attenuated phenotype.

In accordance with the methods of the invention, gene position-shifted RSV can be readily constructed and characterized that incorporate at least one and up to a full complement of attenuating mutations present within a panel of biologically derived mutant RSV strains. Thus, mutations can be assembled in any combination from a selected panel of mutants, for example, cpts RSV 248 (ATCC VR 2450), cpts RSV 248/404 (ATCC VR 2454), cpts RSV 248/955 (ATCC VR 2453), cpts RSV 530 (ATCC VR 2452), cpts RSV 530/1009 (ATCC VR 2451), cpts RSV 530/1030 (ATCC VR 2455), RSV B-1 cp52/2B5 (ATCC VR 2542), and RSV B-1 cp-23 (ATCC VR 2579). In this manner, attenuation of recombinant vaccine candidates can be finely calibrated for use in one or more classes of patients, including seronegative infants.

In more specific embodiments, gene position-shifted RSV for vaccine use incorporate at least one and up to a full complement of attenuating mutations specifying a temperature-sensitive and/or attenuating amino acid substitution at Asn43, Phe521, Gln831, Met1169 or Tyr1321 in the RSV polymerase gene L, or a temperature-sensitive nucleotide substitution in the gene-start sequence of gene M2. Alternatively or additionally, gene position-shifted RSV of claim may incorporate at least one and up to a full complement of mutations from cold-passaged attenuated RSV, for example one or more mutations specifying an amino acid substitution at Val267 in the RSV N gene, Glu218 or Thr523 in the RSV F gene, Cys319 or His1690 in the RSV polymerase gene L.

In other detailed embodiments, the gene position-shifted RSV of the invention is further modified to incorporate attenuating mutations selected from (i) a panel of mutations specifying temperature-sensitive amino acid substitutions Gln831 to Leu, and Tyr1321 to Asn in the RSV polymerase gene L; (ii) a temperature-sensitive nucleotide substitution in the gene-start sequence of gene M2; (iii) an attenuating panel of mutations adopted from cold-passaged RSV specifying amino acid substitutions Val267 Ile in the RSV N gene, and Cys319 Tyr and His1690 Tyr in the RSV polymerase gene L; or (iv) deletion or ablation of expression of one or more of the RSV SH, NS1, NS2, G and M2-2 genes. Preferably, these and other examples of gene position-shifted RSV incorporate at least two attenuating mutations adopted from biologically derived mutant RSV, which may be derived from the same or different biologically derived mutant RSV strains. Also preferably, these exemplary mutants have one or more of their attenuating mutations stabilized by multiple nucleotide changes in a codon specifying the mutation.

In accordance with the foregoing description, the ability to produce infectious RSV from cDNA permits introduction of specific engineered changes within gene position-shifted RSV. In particular, infectious, recombinant RSV are employed for identification of specific mutation(s) in biologically derived, attenuated RSV strains, for example mutations which specify ts, ca, att and other phenotypes. Desired mutations are thus identified and introduced into recombinant, gene position-shifted RSV vaccine strains. The capability of producing virus from cDNA allows for routine incorporation of these mutations, individually or in various selected combinations, into a full-length cDNA clone, whereafter the phenotypes of rescued recombinant viruses containing the introduced mutations to be readily determined.

By identifying and incorporating specific, biologically derived mutations associated with desired phenotypes, e.g., a cp or ts phenotype, into infectious chimeric RSV clones, the invention provides for other, site-specific modifications at, or within close proximity to, the identified mutation. Whereas most attenuating mutations produced in biologically derived RSV are single nucleotide changes, other "site specific" mutations can also be incorporated by recombinant techniques into biologically derived or recombinant RSV. As used herein, site-specific mutations include insertions, substitutions, deletions or rearrangements of from 1 to 3, up to about 5-15 or more altered nucleotides (e.g., altered from a wild-type RSV sequence, from a sequence of a selected mutant RSV strain, or from a parent recombinant RSV clone subjected to mutagenesis). Such site-specific mutations may be incorporated at, or within the region of, a selected, biologically derived mutation. Alternatively, the mutations can be introduced in various other contexts within an RSV clone, for example at or near a cis-acting regulatory sequence or nucleotide sequence encoding a protein active site, binding site, immunogenic epitope, etc. Site-specific RSV mutants typically retain a desired attenuating phenotype, but may additionally exhibit altered phenotypic characteristics unrelated to attenuation, e.g., enhanced or broadened immunogenicity, and/or improved growth. Further examples of desired, site-specific mutants include recombinant RSV designed to incorporate additional, stabilizing nucleotide mutations in a codon specifying an attenuating mutation. Where possible, two or more nucleotide substitutions are introduced at codons that specify attenuating amino acid changes in a parent mutant or recombinant RSV clone, yielding a biologically derived or recombinant RSV having genetic resistance to reversion from an attenuated phenotype. In other embodiments, site-specific nucleotide substitutions, additions, deletions or rearrangements are introduced upstream (N-terminal direction) or downstream (C-terminal direction), e.g., from 1 to 3, 5-10 and up to 15 nucleotides or more 5' or 3', relative to a targeted nucleotide position, e.g., to construct or ablate an existing cis-acting regulatory element.

In addition to single and multiple point mutations and site-specific mutations, changes to gene position-shifted RSV disclosed herein include deletions, insertions, substitutions or rearrangements of whole genes or genome segments. These mutations may alter small numbers of bases (e.g., from 15-30 bases, up to 35-50 bases or more), large blocks of nucleotides (e.g., 50-100, 100-300, 300-500, 500-1,000 bases), or nearly complete or complete genes (e.g., 1,000-1,500 nucleotides, 1,500-2,500 nucleotides, 2,500-5,000, nucleotides, 5,00-6, 5000 nucleotides or more) in the donor or recipient genome or antigenome, depending upon the nature of the change (i.e., a small number of bases may be changed to insert or ablate an immunogenic epitope or change a small genome segment, whereas large block(s) of bases are involved when genes or large genome segments are added, substituted, deleted or rearranged.

In alternative aspects of the invention, the infectious gene position-shifted RSV produced from a cDNA-expressed genome or antigenome can be any of the RSV or RSV-like strains, e.g., human, bovine, murine, etc., or of any pneumovirus, e.g., pneumonia virus of mice avian pneumovirus (previously called turkey rhinotracheitis virus). To engender a protective immune response, the RSV strain may be one which is endogenous to the subject being immunized, such as human RSV being used to immunize humans. The genome or antigenome of endogenous RSV can be modified, however, to express RSV genes or genome segments from a combination of different sources, e.g., a combination of genes or genome segments from different RSV species, subgroups, or strains, or from an RSV and another respiratory pathogen such as PIV.

Introduction of the foregoing defined mutations into an infectious, gene position-shifted RSV clone can be achieved by a variety of well known methods. By "infectious clone" with regard to DNA is meant cDNA or its product, synthetic or otherwise, which can be transcribed into genomic or antigenomic RNA capable of serving as template to produce the genome of an infectious virus or subviral particle. Thus, defined mutations can be introduced by conventional techniques (e.g., site-directed mutagenesis) into a cDNA copy of the genome or antigenome. The use of antigenome or genome cDNA subfragments to assemble a complete antigenome or genome cDNA as described herein has the advantage that each region can be manipulated separately (smaller cDNAs are easier to manipulate than large ones) and then readily assembled into a complete cDNA. Thus, the complete antigenome or genome cDNA, or any subfragment thereof, can be used as template for oligonucleotide-directed mutagenesis. This can be through the intermediate of a single-stranded phagemid form, such as using the Muta-gene® kit of Bio-Rad Laboratories (Richmond, Calif.) or a method using a double-stranded plasmid directly as template such as the Chameleon mutagenesis kit of Stratagene (La Jolla, Calif.), or by the polymerase chain reaction employing either an oligonucleotide primer or template which contains the mutation(s) of interest. A mutated subfragment can then be assembled into the complete antigenome or genome cDNA. A variety of other mutagenesis techniques are known and available for use in producing the mutations of interest in the RSV antigenome or genome cDNA. Mutations can vary from single nucleotide changes to replacement of large cDNA pieces containing one or more genes or genome regions.

Thus, in one illustrative embodiment mutations are introduced by using the Muta-gene phagemid in vitro mutagenesis kit available from Bio-Rad. In brief, cDNA encoding a portion of an RSV genome or antigenome is cloned into the plasmid pTZ18U, and used to transform CJ236 cells (Life Technologies). Phagemid preparations are prepared as recommended by the manufacturer. Oligonucleotides are designed for mutagenesis by introduction of an altered nucleotide at the desired position of the genome or antigenome. The plasmid containing the genetically altered genome or antigenome fragment is then amplified and the mutated piece is then reintroduced into the full-length genome or antigenome clone.

The invention also provides methods for producing an infectious gene position-shifted RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2(ORF1) protein. In an RSV minigenome system, genome and antigenome were equally active in rescue, whether complemented by RSV or by plasmids, indicating that either genome or antigenome can be used and thus the choice can be made on methodologic or other grounds.

A native RSV genome typically comprises a negative-sense polynucleotide molecule which, through complementary viral mRNAs, encodes eleven species of viral proteins, i.e., the nonstructural species NS1 and NS2, N, P, matrix (M), small hydrophobic (SH), glycoprotein (G), fusion (F), M2(ORF1), M2(ORF2), and L, substantially as described in (Mink et al., Virology 185:615-624, 1991; Stec et al., Virology 183:273-287, 1991; and Connors et al., Virol. 208:478-484, 1995; Collins et al., Proc. Nat. Acad. Sci. USA 93:81-85, 1996), each incorporated herein by reference. For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule, or can be expressed directly from the genome or antigenome cDNA.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Alternatively, additional RSV proteins needed for a productive infection can be supplied by coexpression.

An RSV antigenome may be constructed for use in the present invention by assembling cloned cDNA segments, representing in aggregate the complete antigenome, by polymerase chain reaction (PCR; described in, e.g., U.S. Pat. Nos. 4,683,195 and 4,683,202, and *PCR Protocols: A Guide to Methods and Applications*, Innis et al., eds., Academic Press, San Diego, 1990, incorporated herein by reference) of reverse-transcribed copies of RSV mRNA or genome RNA. For example, cDNAs containing the lefthand end of the antigenome, spanning from an appropriate promoter (e.g., T7 RNA polymerase promoter) and the leader region complement to the SH gene, are assembled in an appropriate expression vector, such as a plasmid (e.g., pBR322) or various available cosmid, phage, or DNA virus vectors. The vector may be modified by mutagenesis and/or insertion of synthetic polylinker containing unique restriction sites designed to facilitate assembly. For example, a plasmid vector described herein was derived from pBR322 by replacement of the PstI-EcoR1 fragment with a synthetic DNA containing convenient restriction enzyme sites. Use of pBR322 as a vector stabilized nucleotides 3716-3732 of the RSV sequence, which otherwise sustained nucleotide deletions or insertions, and propagation of the plasmid was in bacterial strain DH10B to avoid an artifactual duplication and insertion which otherwise occurred in the vicinity of nt 4499. For ease of preparation the G, F and M2 genes can be assembled in a separate vector, as can be the L and trailer sequences. The right-hand end (e.g., L and trailer sequences) of the antigenome plasmid may contain additional sequences as desired, such as a flanking ribozyme and tandem T7 transcriptional terminators. The ribozyme can be hammerhead type (e.g., Grosfeld et al., *J. Virol.* 69:5677-5686, 1995), which would yield a 3' end containing a single nonviral nucleotide, or can any of the other suitable ribozymes such as that of hepatitis delta virus (Perrotta et al., *Nature* 350:434436, 1991) which would yield a 3' end free of non-RSV nucleotides. A middle segment (e.g., G-to-M2 piece) is inserted into an appropriate restriction site of the leader-to-SH plasmid, which in turn is the recipient for the L-trailer-ribozyme-terminator piece, yielding a complete antigenome. In an illustrative example described herein, the leader end was constructed to abut the promoter for T7 RNA polymerase which included three transcribed G residues for optimal activity; transcription donates these three nonviral G's to the 5' end of the antigenome. These three nonviral G residues can be omitted to yield a 5' end free of nonviral nucleotides. To generate a nearly correct 3' end, the trailer end was constructed to be adjacent to a hammerhead ribozyme, which upon cleavage would donate a single 3'-phosphorylated U residue to the 3' end of the encoded RNA.

In certain embodiments of the invention, complementing sequences encoding proteins necessary to generate a transcribing, replicating RSV nucleocapsid are provided by one or more helper viruses. Such helper viruses can be wild-type or mutant. Preferably, the helper virus can be distinguished phenotypically from the virus encoded by the RSV cDNA. For example, it is desirable to provide monoclonal antibodies which react immunologically with the helper virus but not the virus encoded by the RSV cDNA. Such antibodies can be neutralizing antibodies. In some embodiments, the antibodies can be used to neutralize the helper virus background to facilitate identification and recovery of the recombinant virus, or in affinity chromatography to separate the helper virus from the recombinant virus. Mutations can be introduced into the RSV cDNA which render the recombinant RSV nonreactive or resistant to neutralization with such antibodies.

A variety of nucleotide insertions and deletions can be made in the gene position-shifted RSV genome or antigenome to generate a properly attenuated clone. The nucleotide length of the genome of wild-type human RSV (15,222 nucleotides) is a multiple of six, and members of the Paramyxovirus and Morbillivirus genera typically abide by a "rule of six," i.e., genomes (or minigenomes) replicate efficiently only when their nucleotide length is a multiple of six (thought to be a requirement for precise spacing of nucleotide residues relative to encapsidating NP protein). Alteration of RSV genome length by single residue increments had no effect on the efficiency of replication, and sequence analysis of several different minigenome mutants following passage showed that the length differences were maintained without compensatory changes. Thus, RSV lacks the strict requirement of genome length being a multiple of six, and nucleotide insertions and deletions can be made in the RSV genome or antigenome without defeating replication of the recombinant RSV of the present invention.

Alternative means to construct cDNA encoding a gene position-shifted RSV genome or antigenome include by reverse transcription-PCR using improved PCR conditions (e.g., as described in Cheng et al., *Proc. Natl. Acad. Sci. USA* 91:5695-5699, 1994; Samal et al., *J. Virol.* 70:5075-5082, 1996, each incorporated herein by reference) to reduce the number of subunit cDNA components to as few as one or two pieces. In other embodiments different promoters can be used (e.g., T3, SP6) or different ribozymes (e.g., that of hepatitis delta virus. Different DNA vectors (e.g., cosmids) can be used for propagation to better accommodate the large size genome or antigenome.

The N, P and L proteins, necessary for RNA replication, require an RNA polymerase elongation factor such as the M2(ORF1) protein for processive transcription. Thus M2(ORF1) or a substantially equivalent transcription elongation factor for negative strand RNA viruses is required for the production of infectious RSV and is a necessary component of functional nucleocapsids during productive infection.

The need for the M2(ORF1) protein is consistent with its role as a transcription elongation factor. The need for expression of the RNA polymerase elongation factor protein for negative strand RNA viruses is a feature of the present invention. M2(ORF1) can be supplied by expression of the complete M2-gene, either by the chimeric genome or antigenome or by coexpression therewith, although in this form the second ORF2 may also be expressed and have an inhibitory effect on RNA replication. Therefore, for production of infectious virus using the complete M2 gene the activities of the two ORFs should be balanced to permit sufficient expression of M2(ORF1) to provide transcription elongation activity yet not so much of M2(ORF2) to inhibit RNA replication. Alternatively, the ORF1 protein is provided from a cDNA engineered to lack ORF2 or which encodes a defective ORF2. Efficiency of virus production may also be improved by coexpression of additional viral protein genes, such as those encoding envelope constituents (i.e., SH, M, G, F proteins).

In accordance with these results concerning M2(ORF2), another exemplary embodiment of the invention is provided comprising a gene position-shifted RSV that incorporate a mutation of M2(ORF2) (Collins and Wertz, *J. Virol.* 54:65-71, 1985; Collins et al., *J. Gen. Virol.* 71:3015-3020, 1990, Collins et al., *Proc. Natl. Acad. Sci. USA* 93:81-85, 1996, each incorporated herein by reference) to yield novel RSV vaccine candidates (see U.S. Provisional Patent Application No. 60/143,097, filed by Collins et al. on Jul. 9, 1999, incorporated herein by reference). In certain aspects, expression of M2 ORF2 is reduced or ablated by modifying the recombinant RSV genome or antigenome to incorporate a frame shift mutation or one or stop codons in M2 ORF2 yielding a "knock out" viral clone. Alternatively, M2 ORF2 is deleted in whole or in part to render the M2-2 protein partially or entirely non-functional or to disrupt its expression altogether to yield a M2 ORF2 "deletion mutant" chimeric RSV. Alternatively, the M2-2 ORF may be transpositioned in the genome or antigenome to a more promoter-proximal or promoter-distal position compared to the natural gene order position of M2-2 gene to up-regulate or down-regulate expression of the M2-2 ORF. In additional embodiments, the M2-2 ORF is incorporated in the genome or antigenome as a separate gene having a gene start and gene end gene end signal, which modification results in up-regulation of the M2-2 ORF.

The gene position-shifted RSV of the invention that incorporate mutations in M2 ORF2 possess highly desirable phenotypic characteristics for vaccine development. The above identified modifications in the recombinant genome or antigenome specify one or more desired phenotypic changes in the resulting virus or subviral particle. Vaccine candidates are thus generated that exhibit one or more characteristics identified as (i) a change in mRNA transcription, (ii) a change in the level of viral protein expression; (iii) a change in genomic or antigenomic RNA replication, (iv) a change in viral growth characteristics, (v), a change in viral plaque size, and/or (vi) a change in cytopathogenicity.

In exemplary RSV recombinants incorporating an M2 ORF 2 deletion or knock out mutation, desired phenotypic changes include attenuation of viral growth compared to growth of a corresponding wild-type or mutant parental RSV strain. In more detailed aspects, viral growth in cell culture may be attenuated by approximately 10-fold or more attributable to mutations in M2 ORF2. Kinetics of viral growth are also shown to be modified in a manner that is beneficial for vaccine development.

Also included within the invention are M2-ORF 2 deletion and knock out mutant RSV that exhibit delayed kinetics of viral mRNA synthesis compared to kinetics of mRNA synthesis of corresponding wild-type or mutant parental RSV strains. Despite these delayed transcription kinetics, these novel vaccine candidates exhibit an increase in cumulative mRNA synthesis compared to parental virus. These phenotypic changes typically are associated with an increase in viral protein accumulation in infected cells compared to protein accumulation in cells infected with wild-type or other parental RSV strains. At the same time, viral RNA replication is reduced in M2 ORF2 gene position-shifted RSV compared to that of a parental RSV strain having normal M2 ORF2 function, whereby accumulation of genomic or antigenomic RNA is reduced.

Within preferred aspects of the invention, chimeric M2 ORF2 deletion and "knock out" RSV are engineered to express undiminished or, more typically, increased levels of viral antigen(s) while also exhibiting an attenuated phenotype. Immunogenic potential is thus preserved due to the undiminished or increased mRNA transcription and antigen expression, while attenuation is achieved through incorporation of the heterologous gene(s) or gene segment(s) and concomitant reductions in RNA replication and virus growth attributable to the M2-ORF 2 deletion and knock out mutation. This novel suite of phenotypic traits is highly desired for vaccine development. Other useful phenotypic changes that are observed in M2 ORF2 deletion and knock out gene position-shifted RSV include a large plaque phenotype and altered cytopathogenicity compared to corresponding wild-type or mutant parental RSV strains.

Isolated polynucleotides (e.g., cDNA) encoding a gene position-shifted RSV genome or antigenome and, separately, or in cis, or expressed from the antigenome or genome cDNA, the N, P, L and M2(ORF1) proteins, are inserted by transfection, electroporation, mechanical insertion, transduction or the like, into cells which are capable of supporting a productive RSV infection, e.g., HEp-2, FRhL-DBS2, MRC, and Vero cells. Transfection of isolated polynucleotide sequences may be introduced into cultured cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., (ed.) *Current Protocols in Molecular Biology*, John Wiley and Sons, Inc., NY, 1987, cationic lipid-mediated transfection (Hawley-Nelson et al., *Focus* 15:73-79, 1993) or a commercially available transfection regent, e.g., LipofectACE® (Life Technologies) (each of the foregoing references are incorporated herein by reference).

The N, P, L and M2(ORF1) proteins are encoded by one or more cDNAs and expression vectors which can be the same or separate from that which encodes the genome or antigenome, and various combinations thereof. Additional proteins may be included as desired, encoded by its own vector or by a vector encoding a N, P, L, or M2(ORF1) protein and/or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., *Virology,* 210:202-205, 1995, incorporated herein by reference). The viral proteins, and/or T7 RNA polymerase, can also be provided from transformed mammalian cells, or by transfection of preformed mRNA or protein.

Alternatively, synthesis of antigenome or genome can be conducted in vitro (cell-free) in a combined transcription-translation reaction, followed by transfection into cells. Or, antigenome or genome RNA can be synthesized in vitro and transfected into cells expressing RSV proteins.

To select candidate vaccine viruses according to the invention, the criteria of viability, attenuation and immunogenicity are determined according to well known methods. Viruses which will be most desired in vaccines of the invention must maintain viability, have a stable attenuation phenotype, exhibit replication in an immunized host (albeit at lower levels), and effectively elicit production of an immune response in a vaccinee sufficient to confer protection against serious disease caused by subsequent infection from wild-type virus. Clearly, the heretofore known and reported RS virus mutants do not meet all of these criteria Indeed, contrary to expectations based on the results reported for known attenuated RSV, viruses of the invention are not only viable and more appropriately attenuated than previous mutants, but are more stable genetically in vivo than those previously studied mutants—retaining the ability to stimulate a protective immune response and in some instances to expand the protection afforded by multiple modifications, e.g., induce protection against different viral strains or subgroups, or protection by a different immunologic basis, e.g., secretory versus serum immunoglobulins, cellular immunity, and the like. Prior to the invention, genetic instability of the ts phenotype following replication in vivo has been common for ts viruses (Murphy et al., Infect. Immun. 37:235-242, 1982).

To propagate a gene position-shifted RSV virus for vaccine use and other purposes, a number of cell lines which allow for RSV growth may be used. RSV grows in a variety of human and animal cells. Preferred cell lines for propagating attenuated RS virus for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0 or more, and are cultivated under conditions permissive for replication of the virus, e.g., at about 30-37° C. and for about 3-5 days, or as long as necessary for virus to reach an adequate titer. Virus is removed from cell culture and separated from cellular components, typically by well known clarification procedures, e.g., centrifugation, and may be further purified as desired using procedures well known to those skilled in the art.

Gene position-shifted RSV which has been attenuated and otherwise modified as described herein can be tested in various well known and generally accepted in vitro and in vivo models to confirm adequate attenuation, resistance to phenotypic reversion, and immunogenicity for vaccine use. In in vitro assays, the modified virus (e.g., a multiply attenuated, biologically derived or recombinant RSV) is tested for temperature sensitivity of virus replication, i.e. ts phenotype, and for the small plaque phenotype. Modified viruses are further tested in animal models of RSV infection. A variety of animal models have been described and are summarized in (Meignier et al., eds., Animal Models of Respiratory Syncytial Virus Infection, Merieux Foundation Publication, 1991, which is incorporated herein by reference). A cotton rat model of RSV infection is described in (U.S. Pat. No. 4,800,078 and Prince et al., Virus Res. 3:193-206, 1985), which are incorporated herein by reference, and is considered predictive of attenuation and efficacy in humans and non-human primates. In addition, a primate model of RSV infection using the chimpanzee is predictive of attenuation and efficacy in humans, as is described in detail in (Richardson et al., J. Med. Virol. 3:91-100, 1978; Wright et al., Infect. Immun. 37:397-400, 1982; Crowe et al., Vaccine 11:1395-1404, 1993, each incorporated herein by reference).

RSV model systems, including rodents and chimpanzees for evaluating attenuation and infectivity of RSV vaccine candidates are widely accepted in the art and the data obtained therefrom correlate well with RSV infection and attenuation. The mouse and cotton rat models are especially useful in those instances in which candidate RSV viruses display inadequate growth in chimpanzees, for example in the case of RSV subgroup B viruses.

In accordance with the foregoing description and based on the examples below, the invention also provides isolated, infectious gene position-shifted RSV compositions for vaccine use. The attenuated chimeric virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium where it can be propagated and characterized in a controlled setting. For example, attenuated RSV of the invention may be produced by an infected cell culture, separated from the cell culture and added to a stabilizer.

RSV vaccines of the invention contain as an active ingredient an immunogenically effective amount of RSV produced as described herein. Biologically derived or recombinant RSV can be used directly in vaccine formulations, or lyophilized. Lyophilized virus will typically be maintained at about 4° C. When ready for use the lyophilized virus is reconstituted in a stabilizing solution, e.g., saline or comprising SPG, Mg++ and HEPES, with or without adjuvant, as further described below. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. Acceptable adjuvants include incomplete Freund's adjuvant, aluminum phosphate, aluminum hydroxide, or alum, which are materials well known in the art. Preferred adjuvants also include Stimulon® QS-21 (Aquila Biopharmaceuticals, Inc., Framingham, Mass.), MPL®(3-0-deacylated monophosphoryl lipid A; Corixa, Hamilton, Mont.), and interleukin-12 (Genetics Institute, Cambridge, Mass.).

Upon immunization with a gene position-shifted RSV vaccine composition as described herein, via aerosol, droplet, oral, topical or other route, the immune system of the host responds to the vaccine by producing antibodies specific for one or more RSV virus proteins, e.g., F and/or G glycoproteins. As a result of the vaccination the host becomes at least partially or completely immune to RSV infection, or resistant to developing moderate or seyere RSV disease, particularly of the lower respiratory tract.

Gene position-shifted RSV vaccines of the invention may comprise attenuated virus that elicits an immune response against a single RSV strain or antigenic subgroup, e.g. A or B, or against multiple RSV strains or subgroups. In this context, the gene position-shifted RSV can elicit a monospecific immune response or a polyspecific immune response against multiple RSV strains or subgroups. Alternatively, gene position-shifted RSV having different immunogenic characteristics can be combined in a vaccine mixture or administered separately in a coordinated treatment protocol to elicit more effective protection against one RSV strain, or against multiple RSV strains or subgroups.

The host to which the vaccine is administered can be any mammal susceptible to infection by RSV or a closely related virus and capable of generating a protective immune response to antigens of the vaccinizing virus. Thus, suitable hosts include humans, non-human primates, bovine, equine, swine, ovine, caprine, lagamorph, rodents, etc. Accordingly, the invention provides methods for creating vaccines for a variety of human and veterinary uses.

The vaccine compositions containing the attenuated gene position-shifted RSV of the invention are administered to a patient susceptible to or otherwise at risk of RSV infection in an "immunogenically effective dose" which is sufficient to induce or enhance the individual's immune response capabilities against RSV. In the case of human subjects, the attenuated virus of the invention is administered according to well established human RSV vaccine protocols, as described in, e.g., (Wright et al., *Infect. Immun.* 37:397400, 1982; Kim et al., *Pediatrics* 52:56-63, 1973; and Wright et al., *J. Pediatr.* 88:931-936, 1976), which are each incorporated herein by reference. Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of gene position-shifted RSV vaccine administered and the timing and repetition of administration will be determined based on the patient's state of health and weight, the mode of administration, the nature of the formulation, etc. Dosages will generally range from about $10^3$ to about $10^6$ plaque forming units (PFU) or more of virus per patient, more commonly from about $10^4$ to $10^5$ PFU virus per patient. In any event, the vaccine formulations should provide a quantity of attenuated RSV of the invention sufficient to effectively stimulate or induce an anti-RSV immune response, e.g., as can be determined by complement fixation, plaque neutralization, and/or enzyme-linked immunosorbent assay, among other methods. In this regard, individuals are also monitored for signs and symptoms of upper respiratory illness. As with administration to chimpanzees, the attenuated virus of the vaccine grows in the nasopharynx of vaccinees at levels approximately 10-fold or more lower than wild-type virus, or approximately 10-fold or more lower when compared to levels of incompletely attenuated RSV.

In neonates and infants, multiple administration may be required to elicit sufficient levels of immunity. Administration should begin within the first month of life, and at intervals throughout childhood, such as at two months, six months, one year and two years, as necessary to maintain sufficient levels of protection against native (wild-type) RSV infection. Similarly, adults who are particularly susceptible to repeated or serious RSV infection, such as, for example, health care workers, day care workers, family members of young children, the elderly, individuals with compromised cardiopulmonary function, may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered gene position-shifted RSV strain expressing a cytokine or an additional protein rich in T cell epitopes may be particularly advantageous for adults rather than for infants. RSV vaccines produced in accordance with the present invention can be combined with viruses expressing antigens of another subgroup or strain of RSV to achieve protection against multiple RSV subgroups or strains. Alternatively, the vaccine virus may incorporate protective epitopes of multiple RSV strains or subgroups engineered into one RSV clone as described herein.

Typically when different vaccine viruses are used they will be administered in an admixture simultaneously, but they may also be administered separately. For example, as the F glycoproteins of the two RSV subgroups differ by only about 10% in amino acid sequence, this similarity is the basis for a cross-protective immune response as observed in animals immunized with RSV or F antigen and challenged with a heterologous strain. Thus, immunization with one strain may protect against different strains of the same or different subgroup. However, optimal protection probably will require immunization against both subgroups.

The gene position-shifted RSV vaccines of the invention elicit production of an immune response that is protective against serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there are detectable levels of host engendered serum and secretory antibodies which are capable of neutralizing homologous (of the same subgroup) wild-type virus in vitro and in vivo. In many instances the host antibodies will also neutralize wild-type virus of a different, non-vaccine subgroup.

Preferred gene position-shifted RSV of the present invention exhibit a very substantial diminution of virulence when compared to wild-type virus that is circulating naturally in humans. The gene position-shifted virus is sufficiently attenuated so that symptoms of infection will not occur in most immunized individuals. In some instances the attenuated virus may still be capable of dissemination to unvaccinated individuals. However, its virulence is sufficiently abrogated such that severe lower respiratory tract infections in the vaccinated or incidental host do not occur.

The level of attenuation of gene position-shifted RSV vaccine virus may be determined by, for example, quantifying the amount of virus present in the respiratory tract of an immunized host and comparing the amount to that produced by wild-type RSV or other attenuated RSV which have been evaluated as candidate vaccine strains. For example, the attenuated chimeric virus of the invention will have a greater degree of restriction of replication in the upper respiratory tract of a highly susceptible host, such as a chimpanzee, compared to the levels of replication of wild-type virus, e.g., 10- to 1000fold less. Also, the level of replication of the attenuated RSV vaccine strain in the upper respiratory tract of the chimpanzee should be less than that of the RSV A2 ts-1 mutant, which was demonstrated previously to be incompletely attenuated in seronegative human infants. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RS virus in the nasopharynx of an infected host are well known in the literature. Specimens are obtained by aspiration or washing out of nasopharyngeal secretions and virus quantified in tissue culture or other by laboratory procedure. See, for example, (Belshe et al., *J. Med. Virology* 1:157-162, 1977; Friedewald et al., *J. Amer. Med. Assoc.* 204:690-694, 1968; Gharpure et al., *J. Virol.* 3:414-421, 1969; and Wright et al., *Arch. Ges. Virusforsch.* 41:238-247, 1973), each incorporated herein by reference. The virus can conveniently be measured in the nasopharynx of host animals, such as chimpanzees.

In some instances it may be desirable to combine the gene position-shifted RSV vaccines of the invention with vaccines which induce protective responses to other agents, particularly other childhood viruses. For example, a gene position-shifted RSV vaccine of the present invention can be administered simultaneously with parainfluenza virus vaccine, such as described in Clements et al., *J. Clin. Microbiol.* 29:1175-1182, 1991), which is incorporated herein by reference. In another aspect of the invention the chimeric RSV can be employed as a vector for protective antigens of other respiratory tract pathogens, such as PIV, by incorporating the sequences encoding those protective antigens into the gene position-shifted RSV genome or antigenome which is used to produce infectious recombinant RSV, as described herein.

In yet another aspect of the invention a gene position-shifted RSV is employed as a vector for transient gene therapy of the respiratory tract. According to this embodiment the gene position-shifted RSV genome or antigenome incorporates a sequence which is capable of encoding a gene product of interest. The gene product of interest is under control of the same or a different promoter from that which controls RSV expression. The infectious RSV produced by coexpressing the recombinant RSV genome or antigenome with the N, P, L and M2(ORF1) proteins and containing a sequence encoding the gene product of interest is administered to a patient. This can involve a recombinant RSV which is fully infectious (i.e., competent to infect cultured cells and produce infectious progeny), or can be a recombinant RSV which, for example, lacks one or more of the G, F and SH surface glycoprotein genes and is propagated in cells which provide one or more of these proteins in trans by stable or transient expression. In such a case, the recombinant virus produced would be competent for efficient infection, but would be highly inefficient in producing infectious particles. The lack of expressed cell surface glycoproteins also would reduce the efficiency of the host immune system in eliminating the infected cells. These features would increase the durability and safety of expression of the foreign gene.

With regard to gene therapy, administration is typically by aerosol, nebulizer, or other topical application to the respiratory tract of the patient being treated. Gene position-shifted RSV is administered in an amount sufficient to result in the expression of therapeutic or prophylactic levels of the desired gene product. Examples of representative gene products which are administered in this method include those which encode, for example, those particularly suitable for transient expression, e.g., interleukin-2, interleukin-4, gamma-interferon, GM-CSF, G-CSF, erythropoietin, and other cytokines, glucocerebrosidase, phenylalanine hydroxylase, cystic fibrosis transmembrane conductance regulator (CFTR), hypoxanthine-guanine phosphoribosyl transferase, cytotoxins, tumor suppressor genes, antisense RNAs, and vaccine antigens.

The following examples are provided by way of illustration, not limitation.

EXAMPLE I

Construction of Recombinant RSV in which the G and F Genes Have Been Rearranged to a Promoter-Proximal Position Singly or in Combination The present example documents rearrangement of the gene order of infectious RSV whereby one or more gene(s) or genome segment(s) encoding an antigenic determinant, exemplified by the G and/or F gene(s), is shifted to a more promoter-proximal position. In one example presented below, the G and F genes are moved coordinately from their wild type gene order positions to occupy rearranged positions 1 and 2 of the recombinant RSV genome or antigenome. This manipulation was performed with a cloned cDNA of RSV antigenomic RNA from which the SH gene was deleted (RSV ΔSH), as described above (see, e.g., Whitehead et al., *J. Virol.* 73:3438-3442, 1999, incorporated herein by reference). Wild type RSV from which the SH gene is deleted grows as well or slightly better than complete wild type RSV in vitro, and is slightly attenuated in the upper respiratory tract of mice and in the upper and lower respiratory tracts of chimpanzee (Bukreyev et al., *J. Virol.* 71:8973-8982, 1997; Whitehead et al., *J. Virol.* 73:3438-3442, 1999, incorporated herein by reference). Its levels of immunogenicity and protective efficacy are closely comparable to those of wild type virus. Thus, RSV ΔSH virus is slightly attenuated compared to wild type virus but otherwise has very similar biological properties, and it represents the parent virus in these studies. These characteristics of the ΔSH virus, combined with the increased genetic stability of RSV deletion mutants in general, render this background particularly useful as a parent recombinant for production of gene position-shifted RSV, facilitating recovery and manipulation of mutant derivatives.

The antigenomic cDNA was manipulated and recombinant virus recovered using procedures and strategies described above (see also, Collins et al., *Proc. Natl. Acad. Sci. USA* 92:11563-11567, 1995; Bukreyev et al., *J. Virol.* 70:6634-6641, 1996; Bukreyev et al., *J. Virol.* 71:8973-8982, 1997; Whitehead et al., *J. Virol.* 72:4467-4471, 1998; Whitehead et al., *Virology* 247:232-239, 1998; Bermingham and Collins, *Proc. Natl. Acad. Sci. USA* 96:11259-11264, 1999; Collins et al., *Virology* 259:251-255, 1999; Bukreyev et al., *Proc. Natl. Acad. Sci. USA* 96:2367-2372, 1999; Juhasz et al., *Vaccine* 17:1416-1424, 1999; Juhasz et al., *J. Virol.* 73:5176-5180, 1999; Teng and Collins, *J. Virol.* 73:466473, 1999; Whitehead et al., *J. Virol.* 73:9773-9780, 1999; Whitehead et al., *J. Virol.* 73:871-877, 1999; Whitehead et al., *J. Virol.* 73:3438-3442, 1999; U.S. Pat. No. 5,993,824; each incorporated herein by reference). The antigenomic cDNA was manipulated as three subclones. One subclone, D51/ΔSH, contains the T7 promoter and left hand end of the genome from the leader region to the downstream end of the M gene. The second subclone, pUC19-GFM2, contains the G, F and M2 genes from the middle of the genome. The third subclone, D39, contains the L gene followed by the trailer from the right hand end of the genome followed by a self-cleaving ribosome sequence and tandem T7 transcription terminators.

PCR with mutagenic primers was used to amplify and modify the ends of cDNAs containing the G and F genes separately or together as a single G-F cDNA (FIG. 1). To make a cDNA of G alone for insertion, PCR was used to amplify nucleotides 4692-5596 of the complete recombinant RSV antigenomic sequence (spanning from the ATG that initiates the G ORF to the downstream end of the G gene-end signal). The PCR primers were designed to add, immediately after the G gene-end signal, the first 6 nucleotides of the G-F intergenic (IG) region followed by a copy of the 10-nucleotide GS signal of the NS1 gene (FIG. 1). The PCR primers also were designed to add a BlpI site at both ends of the amplified cDNA. To make a cDNA of the F gene alone for insertion, PCR was used to amplify nucleotides 5662-7551 of the complete antigenomic sequence (spanning from the ATG that initiates the F ORF to the end of the F gene-end signal). The PCR primers were designed to add, immediately after the F gene-end signal, the first 6 nucleotides of the F-M2 IG followed by a copy of the 10-nucleotide NS1 gene-start signal. The PCR primers also placed a BlpI site on both ends of the cDNA.

To make a cDNA containing the G and F genes for insertion, PCR was used to amplify nucleotides 4692-7551 of the complete antigenomic cDNA (spanning from the ATG of the G ORF to the end of the F gene-end signal) (FIG. 1). The PCR primers were designed to add, immediately after the F gene-end signal, the first 6 nucleotides of the F-M2 IG followed by a copy of the NS1 gene-start signal. The PCR primers also were designed to add a BlpI site on both ends of the cDNA. All cDNAs were sequenced in their entirety to confirm structures.

In order to make a promoter-proximal site for insertion of the G, F, or G-F cDNA, the upstream noncoding region of the NS1 gene was modified by nucleotide substitutions at antigenome positions 92 (G to C, positive-sense) and 97 (A to C), thereby creating a BlpI site (FIG. 1). This manipulation was performed on a BstBI-MfeI subclone containing the first 419 nucleotides of the RSV antigenomic RNA. The nucleotide substitutions were introduced by PCR on complete plasmid (Byrappa et al., *Genome Research* 5:404-407, 1995; incorporated herein by reference). The modified BstBI-MfeI fragment was reinserted into D51/ΔSH, and this subclone served in turn as the recipient for the G, F, and G-F BlpI cDNA fragments constructed as described above. Because Blpl has an asymmetric heptameric recognition sequence, the fragments can only be inserted in the correct orientation.

When the G, F, or G-F cDNA was placed in the promoter-proximal position, the corresponding gene(s) was/were deleted from the normal downstream position, so that each recombinant genome incorporated a single copy of G and F (FIG. 1). To delete G alone, PCR was performed on pUC19-G-F-M2 to amplify the StuI-HpaI fragment (nucleotides 5611-6419, spanning from the G-F IG into the middle of the F gene). In addition, this PCR added the sequence TTAAT-TAAAAACATATTATCACAAA (SEQ ID NO: 3) to the upstream end of the cDNA. This sequence contains a PacI site (italicized), which in the antigenomic cDNA is located within the SH gene-end signal. This piece could then be introduced as a PacI-HpaI fragment into the PacI-HpaI window of unmodified pUC19-GFM2, thereby deleting the G gene. The sequence of the cDNA fragment that had been subjected to PCR was confirmed by dideoxynucleotide sequencing.

Alternatively, to delete F alone, PCR was performed on pUC19-GFM2 to amplify the fragment that runs from the PacI site at nucleotide 4618 to the G gene-end signal at nucleotide 5596. In addition, this PCR added the sequence CACAATTGCATGC (SEQ ID NO: 4) to the downstream end of the cDNA. This sequence contained the upstream part of the F-M2 IG sequence followed by an SphI site (italicized) that is present in the F-M2 IG of the recombinant RSV antigenome. Cloning this cDNA as a PacI-SphI fragment into the PacI-SphI window of unmodified pUC19-GFM2 resulted in deletion of the F gene. The sequence of the cDNA fragment that had been subjected to PCR was confirmed by dideoxynucleotide sequencing.

To delete both the G and F genes, the SphI-BamHI fragment, PCR by the method of Byrappa (Byrappa et al., Genome Research, 5:404-407 (1995)) et al. was used to amplify nucleotides 7559-8506 of pUC-GFM2 (spanning from the F-M2 IG to the M2/L overlap) with the following sequence added to the upstream end of the cDNA: TTAAT-TAAAAACACAATT (SEQ ID NO: 5). The resulting cDNA insert contains a PacI site (italicized) and the upstream part of the F-M2 IG sequence that immediately precedes the SphI site, but lacks the G and F genes. The sequence of the cDNA fragment that had been subjected to PCR was confirmed by dideoxynucleotide sequencing.

Complete antigenomic cDNAs were then assembled as described above (see also, Collins et al., *Proc. Natl. Acad. Sci. USA* 92:11563-11567, 1995; Bukreyev et al., *J. Virol.* 70:6634-6641, 1996; Bukreyev et al., *J. Virol.* 71:8973-8982, 1997; Whitehead et al., *J. Virol.* 72:4467-4471, 1998; Whitehead et al., *Virology* 247:232-239, 1998; Bermingham and Collins, *Proc. Natl. Acad. Sci. USA* 96:11259-11264, 1999; Collins et al., *Virology* 259:251-255, 1999; Bukreyev et al., *Proc. Natl. Acad. Sci. USA* 96:2367-2372, 1999; Juhasz et al., *Vaccine* 17:1416-1424, 1999; Juhasz et al., *J. Virol.* 73:5176-5180, 1999; Teng and Collins, *J. Virol.* 73:466473, 1999; Whitehead et al., *J. Virol.* 73:9773-9780, 1999; Whitehead et al., *J. Virol.* 73:871-877, 1999; Whitehead et al., *J. Virol.* 73:3438-3442, 1999; and U.S. Pat. No. 5,993,8244; each incorporated herein by reference). This assembly yielded cDNAs encoding Blp/ΔSH, G1/ΔSH, F1/ΔSH, and G1F2/ΔSH antigenomic cDNAs.

These cDNAs were transfected individually into HEp-2 cells together with N, P, M2-1 and L support plasmids and incubated at 32° C. (see, e.g., Collins et al., *Proc. Natl. Acad. Sci. USA* 92:11563-11567, 1995; Collins et al., *Virology* 259: 251-255, 1999; U.S. Pat. No. 5,993,824, each incorporated herein by reference). The transfection supernatants were passaged to fresh cells 3 days later, and then subjected to serial passage in HEp-2 cells at 37° C. with intervals of harvest of 3 to 7 days. The shorter time intervals were necessary for monolayers infected with the F1/ΔSH and G1F2/ΔSH viruses because they exhibited a more rapid development of syncytia and subsequent cell destruction. This was interpreted to reflect increased expression of the fusogenic F protein due to the alteration in F gene position. Aliquots of each harvested supernatant were flash-frozen and titrated later in parallel, as shown in FIG. 2. These results indicate that the efficiency of recovery and amplification of the G1F2/ΔSH and F1/ΔSH viruses exceeded those of the Blp/ΔSH or G1/ΔSH virus, as was also determined relative to the ΔSH virus and wild type virus.

Total RNA was isolated from cells infected with each of the recombinant viruses, and RT-PCR of appropriate genome segments was performed which confirmed that the engineered genomic structures were as designed and constructed. In addition, Northern blot analysis confirmed expression of the appropriate subgenomic mRNAs.

The following viruses were then compared with regard to kinetics of growth and antigen production in vitro: wild type RSV (containing the SH gene), ΔSH (with the SH gene deleted but not containing a BlpI site in the NS1 noncoding region), Blp/ΔSH, G1/ΔSH, and G1F2/ΔSH. Replicate monolayer cultures of HEp-2 cells and Vero cells were infected at an MOI of 0.1 plaque forming units (PFU) per cell with an adsorption period of 1 h (−1 to 0 hours). The monolayers were then washed three times and incubated at 37° C. Two duplicate monolayers per virus were harvested at 12 h intervals, beginning immediately post-adsorption at t=0 hours. The medium supernatants were flash-frozen for analysis later by plaque assay to quantitate released infectious virus (FIG. 3A). This showed that the viruses were comparable in their ability to produce infectious virus in Vero (FIG. 3A, upper panel) and HEp-2 (FIG. 3A, lower panel) cells.

In the same experiment, the Vero cell monolayers from each time point (FIG. 3A, upper panel) were harvested and analyzed by Western blotting to characterize the expression of G protein (FIG. 4). A sample of total infected-cell protein from each time point was electrophoresed in denaturing polyacrylamide gel, transferred to nitrocellulose, and analyzed by incubation with an antiserum specific to a peptide of the G protein. Bound antibodies were detected and quantitated using a commercial chemiluminescence kit. The antibody bound to the two major cell-associated forms of the G protein, namely the larger 90 kDa fully-mature form and the smaller 50 kDa incompletely-glycosylated form. This comparison showed that, although the production of infectious particles was similar for all viruses (FIG. 3A, upper panel), the amount of cell-associated G protein was considerably greater in cells infected with the G1/ΔSH or G1F2/ΔSH virus (FIG. 4). Quantitation of the gel bands by densitometry of the exposed film indicated that the G1/ΔSH and G1F2/ΔSH viruses expressed 6-fold and 4-fold, respectively, more G protein than did the Blp/ΔSH virus.

Cell monolayers infected with the F1/ΔSH or G1F2/ΔSH viruses exhibited a rapid onset of cytopathic effect involving syncytium formation, as mentioned above. This was interpreted to reflect increased expression of the F protein. This enhanced cytopathic effect would not contraindicate the use of this virus as a vaccine, since infection in vivo with a vaccine virus involves only a small amount of epithelial cells which die and are replaced whether the onset of cytopathogenicity for these scattered cells is more rapid or not. However, it may be that higher titers of virus might have been achieved if the cytopathogenicity in vitro had been less rapid. Resolution of these factors will be achieved by construction of gene position-shifted RSV in backgrounds that are more highly attenuated. It is notable in this context that the gene shifts did not interfere with the growth of RSV but did increase the total expression of G protein by several fold.

In further studies, the ability of the gene-shift viruses to replicate in HEp-2 and Vero cell monolayers was compared in an experiment in which the multiplicity of infection was 3.0 (FIG. 3B). This was done in two separate experiments that yielded similar results. Data for one of the experiments are shown in FIG. 3B. In this single-cycle growth assay, each of the three viruses containing G and/or F in the promoter-proximal position, namely G1/ΔSH, F1/ΔSH, and G1F2/ΔSH, replicated more efficiently than the control virus Blp/ΔSH. Furthermore, the difference was greater in Vero cells than in HEp-2 cells. For example, at 24 h post infection, the titer of the G1/ΔSH virus was $7.2 \times 10^6$ PFU/ml, compared to $6.8 \times 10^6$ PFU/ml for the Blp/ΔSH control in HEp-2 cells, a difference of 0.4 $\log_{10}$ whereas the respective values in Vero cells were $6.6 \times 10^6$ PFU/ml for the G1/ΔSH virus and $5.6 \times 10^6$ PFU/ml for the Blp/ΔSH control virus, a difference of 1.0 $\log_{10}$. Each of the other gene-shift viruses also had titers in excess of that of the control virus. Thus, the shift of G and/or F to the promoter proximal position provided, in this example, an increase in virus yield in both HEp-2 and Vero cells, with a maximum yield of 10-fold in Vero cells, which is a cell line that is useful for large-scale virus production.

The gene-shift recombinant viruses also were examined for the ability to replicate in the upper and lower respiratory tract of BALB/c mice (Table 1). Mice in groups of 18 animals each were infected with 106 PFU per animal of G1/ΔSH, F1/ΔSH, G1F2/ΔSH, or the control virus Blp/ΔSH. Six animals from each group were sacrificed on days 3, 4 and 5 post-infection, and the nasal turbinates and lungs were harvested and analyzed by plaque assay to determine virus titers in the upper and lower respiratory tracts, respectively. As shown in Table 1, the level of replication of the Blp/ΔSH and F1/ΔSH viruses were essentially indistinguishable. Thus, although the latter virus replicated somewhat more efficiently in vitro, its replication in vivo was not changed. The absence of increased replication or virulence would simplify modification of the gene-shift viruses by the addition of attenuating mutations. The replication of the G1F2/ΔSH virus was marginally lower than that of the "wild type" Blp/ΔSH control, and the replication of the G1/ΔSH virus also was lower, particularly early in the infection. For example, on day 3 the G1/ΔSH virus was 0.7 $\log_{10}$ lower in both the upper and lower respiratory tract compared to the Blp/ΔSH control.

TABLE 1

Replication, in the upper and lower respiratory tract of mice, of recombinant RSV containing the G and/or F genes in the promoter-proximal position.

| Virus[1] | Nasal Turbinates mean titer ± SE ($\log_{10}$ PFU/g tissue) | | | Lungs Mean titer ± SE ($\log_{10}$ PFU/g tissue) | | |
|---|---|---|---|---|---|---|
| | Day 3 | Day 4 | Day 5 | Day 3 | Day 4 | Day 5 |
| Blp/ΔSH | 4.2 ± 0.17 | 4.0 ± 0.32 | 3.5 ± 0.2 | 3.6 ± 0.26 | 4.1 ± 0.37 | 4.5 ± 0.09 |
| G1/ΔSH | 3.5 ± 0.24 | 3.4 ± 0.54 | 3.5 ± 0.24 | 2.9 ± 0.2 | 3.9 ± 0.34 | 4.6 ± 0.13 |
| F1/ΔSH | 4.4 ± 0.11 | 4.1 ± 0.1 | 3.9 ± 0.12 | 3.9 ± 0.09 | 4.7 ± 0.08 | 4.9 ± 0.16 |
| G1F2/ΔSH | 3.3 ± 0.50 | 3.5 ± 0.13 | 3.3 ± 0.13 | 3.1 ± 0.13 | 4.2 ± 0.28 | 4.1 ± 0.07 |

1. BALB/C mice in groups of 18 were inoculated intranasally with $10^6$ PFu per mouse of the indicated virus on day 0. On days 3, 4, and 5, six mice per group were sacrificed and the nasal turbinates and lungs were harvested and virus titers were determined by plaque assay. Mean titers are shown with the standard error indicated.

Thus, shifting one or more genes to the promoter proximal position, or rearranging RSV genes in general, can modestly attenuate the virus for replication in vivo. This has value for designing an attenuated vaccine strain, since it adds to the menu of useful methods of attenuation. Furthermore, it is important to have attenuating mutations that represent different classes or types, such as temperature-sensitive point mutations, non-temperature-sensitive point mutations, gene deletions, and so forth. Different types of mutation operate in different ways to affect viral phenotype, and the presence of multiple types of mutations in a single vaccine virus confers increased stability. Attenuation by gene shift represents an additional useful class of attenuating mutations in this context. The finding that gene shifts according to the invention can confer a modest degree of attenuation provides useful new tools for fine-tuning the attenuation phenotype of vaccine strains.

Certain useful attenuating mutations within the invention are of a "conditional" variety, where attenuation is minimal under specified conditions (e.g., in vitro) and maximal under other conditions (e.g., in vivo). An attenuation phenotype that is minimal or not operant in vitro permits efficient production of vaccine virus, which is particularly important in the case of RSV and other viruses that grow poorly in cell culture. Of course, as illustrated here, the attenuation phenotype must be operant in vivo in order to reduce disease and reactogenicity of the vaccine virus.

The G1/ΔSH recombinant shown here illustrates a particularly desirable combination of traits resulting from the gene-shift. Specifically, its growth in vitro actually was increased up to 10-fold, while its replication in vivo was decreased moderately. This provides the advantage of improved efficiency of vaccine production in conjunction with attenuation in vivo, and improved antigen expression, as described above.

The immunogenicity of the gene-shift viruses in vivo was investigated in BALB/c mice. Mice in groups of six were infected with the individual viruses as described immediately above, and serum samples were taken 1 day prior to inoculation and 28 and 56 days post inoculation (Table 2). The serum samples were analyzed by glycoprotein-specific enzyme-linked immunoadsorbent assay (ELISA) specific to IgG (Table 2). Analysis of G protein-specific IgG showed that the responses to the F1/ΔSH and G1F2/ΔSH viruses were very similar to that for the Blp/ΔSH control virus. On the other hand, the G-specific response to the G1/ΔSH virus moderately decreased (up to four-fold). This likely is due at least in part to the reduced replication of this virus, as described above in Table 1. Analysis of F-specific responses showed that the F1/ΔSH and G1F2/ΔSH viruses had moderate increases (2.5- to 4-fold) in antibody levels compared to the G1/ΔSH and Blp/ΔSH viruses, which is consistent with the interpretation that moving the F gene to the promoter-proximal position results in increased antigen expression in vivo and increased immunogenicity. Furthermore, these results indicated that the gene-shift can result in increased immunogenicity in vivo under conditions where overall replication of the immunizing virus is not changed. This is a highly desirable outcome, since it provides a specific method to make an RSV vaccine that is Δis inherently more immunogenic than the wild type parent virus. It should be noted that the mouse model can be used to identify and characterize biological properties of a virus and can reveal desirable new features such as shown here.

improves growth in cell culture, and is moderately attenuating in vivo (Bukreyev et al., *J. Virol.* 71:8973-8982, 1997; whitehead et al., *J. Virol.* 73:3438-3442, 1999, incorporated herein by reference). However, an RSV vaccine virus that is safe for administration to RSV-naive infants and children requires further attenuation than is provided by the ΔSH deletion alone. Therefore, the present example is provided to demonstrate that gene shift mutants of the invention can be recovered successfully in a highly attenuated background.

Two backgrounds were chosen to exemplify this aspect of the invention, one lacking both the SH and NS2 genes and one lacking the SH, NS1 and NS2 genes. As described in the above-incorporated references, the ΔNS2 and ΔNS1 deletions are each highly attenuating on its own (see, e.g., Whitehead et al., *J. Virol.* 73:3438-3442, 1999). In vitro, the production of virus containing either mutation is delayed and reduced, although under vaccine production conditions a yield of ΔNS2 virus is achieved comparable to that of wild type virus. In chimpanzees, the ΔNS2 and ΔNS1 viruses each are highly attenuated for replication and disease and are highly immunogenic and protective against RSV challenge. Each mutation alone is an excellent candidate to be included in a recombinant vaccine virus, either on its own or in combination with other mutations. The ΔNS1 and ΔNS2 mutations together result in a virus that is even more highly attenuated in vitro than the ΔNS2 virus. In the present example, further combinations of these deletions were constructed and tested for their ability to support further gene position-shifted mutations.

Antigenomic cDNAs were constructed in which the G and F genes were moved to positions 1 and 2 of an antigenome from which the NS2 and SH genes had been deleted, designated G1F2/ΔNS2ΔSH (FIG. 5, panel A), or to positions 1 and 2 of an antigenome in which the NS1, NS2 and SH genes

TABLE 2

Measurement, by glycoprotein-specific enzyme-linked immunoabsorbent assay (ELISA), or serum antibody responses in mice following infection with recombinant RSV containing G and/or F gene in the promoter-proximal position.
Serum immunoglobulin G ELISA titer (mean reciprocal log$_2$ ± SE) against indicated RSV protein[2]

| Virus[1] | No. of animals per group | Anti RSV G IgG | | | Anti RSV F IgG | | |
|---|---|---|---|---|---|---|---|
| | | Pre | Day 28 | Day 56 | Pre | Day 28 | Day 56 |
| B1p/ΔSH | 6 | ≦5.3 ± 0 | 9.6 ± 0.6 | 11.7 ± 0.8 | ≦5.3 ± 0 | 10.3 ± 0.4 | 12.0 ± 0.4 |
| G1/ΔSH | 6 | ≦5.3 ± 0 | 9.0 ± 0.6 | 9.6 ± 0.6 | ≦5.3 ± 0 | 10.0 ± 0.4 | 12.0 ± 0.7 |
| F1/ΔSH | 6 | ≦5.3 ± 0 | 9.6 ± 0.9 | 11.6 ± 0.6 | ≦5.3 ± 0 | 11.6 ± 0.3 | 13.6 ± 0.3 |
| G1F2/ΔSH | 6 | ≦5.3 ± 0 | 9.3 ± 0.7 | 11.6 ± 0.8 | ≦5.3 ± 0 | 12.3 ± 0.4 | 14.0 ± 0.4 |

1. BALB/C mice in groups of six were inoculated intranasally with 10$^6$ PFU of virus in a 0.1 ml inoculum on day 0.

2. Serum samples were taken 1 day prior to inoculation (Pre) and 28 and 56 days post inoculation, and were analyzed by glycoprotein-specific ELISA for IgG antibodies against the RSV G or F protein, as indicated. Mean titers are shown with standard error indicated.

EXAMPLE II

Figure 5:
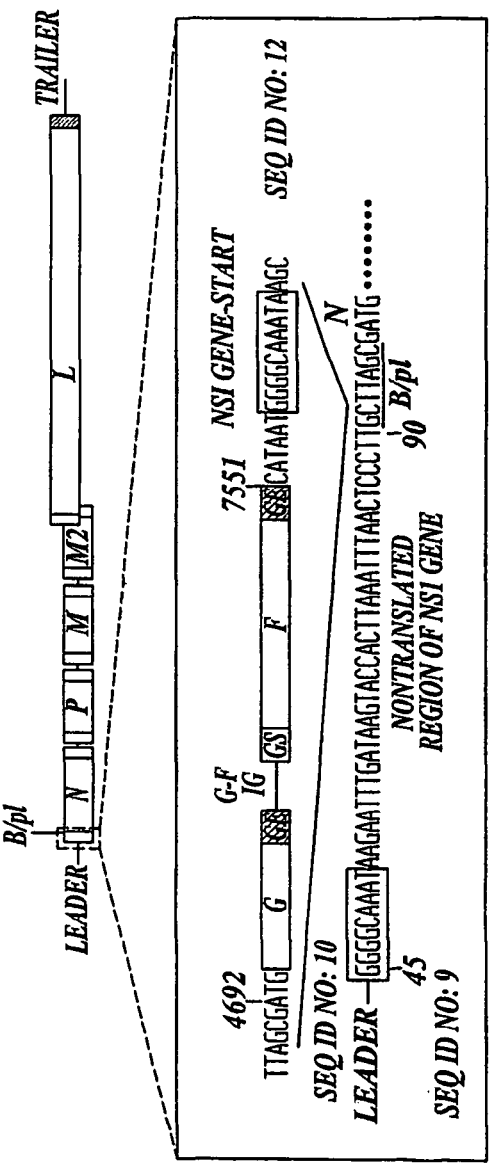

Recombinant RSV Incorporating the G and F Genes in a Promoter-Proximal Shifted Position in a Highly Attenuated Background The gene shift mutations described above were introduced in the context of a genetic background from which the SH gene was deleted. In wild type virus, this deletion modestly were deleted, designated G1F2/ΔNS1ΔNS2ΔSH (FIG. 5, panel B). These antigenomic cDNAs were used to recover recombinant virus as described in Example I above. In both cases, recombinant virus was readily recovered and propagated in vitro. Thus, the present example demonstrates that gene position-shifted RSVs containing multiple attenuating mutations with the G and F genes shifted to the promoter-proximal positions can be readily produced and recovered. These and other gene position-shifted RSVs will be analyzed for levels of replication and antigen expression, as well as growth, immunogenicity and protective efficacy in vivo to select suitable vaccine candidates in accordance with the methods described herein.

In the foregoing examples, representative changes were made in the gene order of RSV to improve its properties as a live-attenuated vaccine. In particular, the G and F genes were moved, singly and in tandem, to a more promoter-proximal position. These two proteins normally occupy positions 7 (G) and 8 (F) in the RSV gene order (NS1-NS2-N-P-M-SH-G-F-M2-L). In order to increase the possibility of successful recovery, the manipulations were performed in a version of RSV in which the SH gene had been deleted. G and F were then moved individually to position 1, or were moved together to positions 1 and 2, respectively. Surprisingly, recombinant RSV were readily recovered in which G or F were moved to position 1, or in which G and F were moved to positions 1 and 2, respectively. This result differed greatly from previous studies with VSV, where movement of the single VSV glycoprotein gene by only two positions was very deleterious to virus growth. The ability to recover these altered viruses also was surprising because RSV replicates inefficiently and because RSV has a complex gene order and movement of the glycoprotein genes involved a large number of position changes. Indeed, the rearranged RSV's grow at least as well as does their immediate parent having the wild type order of genes. As indicated above, this is particularly important for RSV, since the wild type virus grows inefficiently in cell culture and a further reduction in replication in vitro would likely render vaccine preparation unfeasible. It is remarkable that all of the NS1-NS2-N-P-M proteins could be displaced by one or two positions relative to the promoter without a significant decrease in growth fitness. In addition, examination of the expression of the G glycoprotein showed that it was increased up to several-fold over that of its parent virus. This indicated that a vaccine virus containing G and/or F in the first position expresses a higher molar amount of these protective antigens compared to the other viral proteins, and thus represent a virus with highly desirable vaccine properties.

Furthermore, the modification in gene order also was achieved with two highly attenuated vaccine candidates produced in previous work, in which the NS2 gene was deleted on its own as described previously, or in which the NS1 and NS2 genes were deleted together. In these two vaccine candidates, the G and F glycoproteins were moved together to positions 1 and 2 respectively, and the G, F and SH glycoproteins were deleted from their original downstream position. Thus, the recovered viruses G1F2ΔNS2ΔSH and G1F2/ΔNS1ΔNS2ΔSH had two and three genes deleted respectively in addition to the shift of the G and F genes. To illustrate the extent of the changes involved, the gene orders of wild type RSV (NS1-NS2-N-P-M-SH-G-F-M2-L) and the G1F2/ΔNS2ΔSH virus (G-F-NS1-N-P-M-M2-L) or the ΔNS1ΔNS2ΔSH (G-F-N-P-M-M2-L) can be compared. This shows that the positions of most or all of the genes relative to the promoter were changed. Nonetheless, these highly attenuated derivatives retained the capacity to be grown in cell culture, indicating their clear utility for development of candidate vaccine viruses.

EXAMPLE III

Construction of a Chimeric BRSV/HRSV Containing the HRSV G and F Genes in a Promoter-Proximal Shifted Position The present example describes construction of an infectious rBRSV/HRSV chimera in which the HRSV G and F genes are substituted into a recombinant bovine RSV (rBRSV) background. The resulting human-bovine chimera contains two genes of HRSV, namely G and F, and eight genes from BRSV, namely NS1, NS2, N, P, M, SH, M2 and L. Additional detail describing a human-bovine RSV construct having the human G and F genes substituted at their corresponding, wild type positions in a bovine RSV background (designated rBRSV/A2) is provided in U.S. patent application Ser. No. 09/602,212, filed by Bucholz et al. on Jun. 23, 2000, its corresponding PCT application published as WO 01/04335 on Jan. 18, 2001, and its priority provisional U.S. Application No. 60/143,132 filed on Jul. 9, 1999, each incorporated herein by reference.

Figure 6:
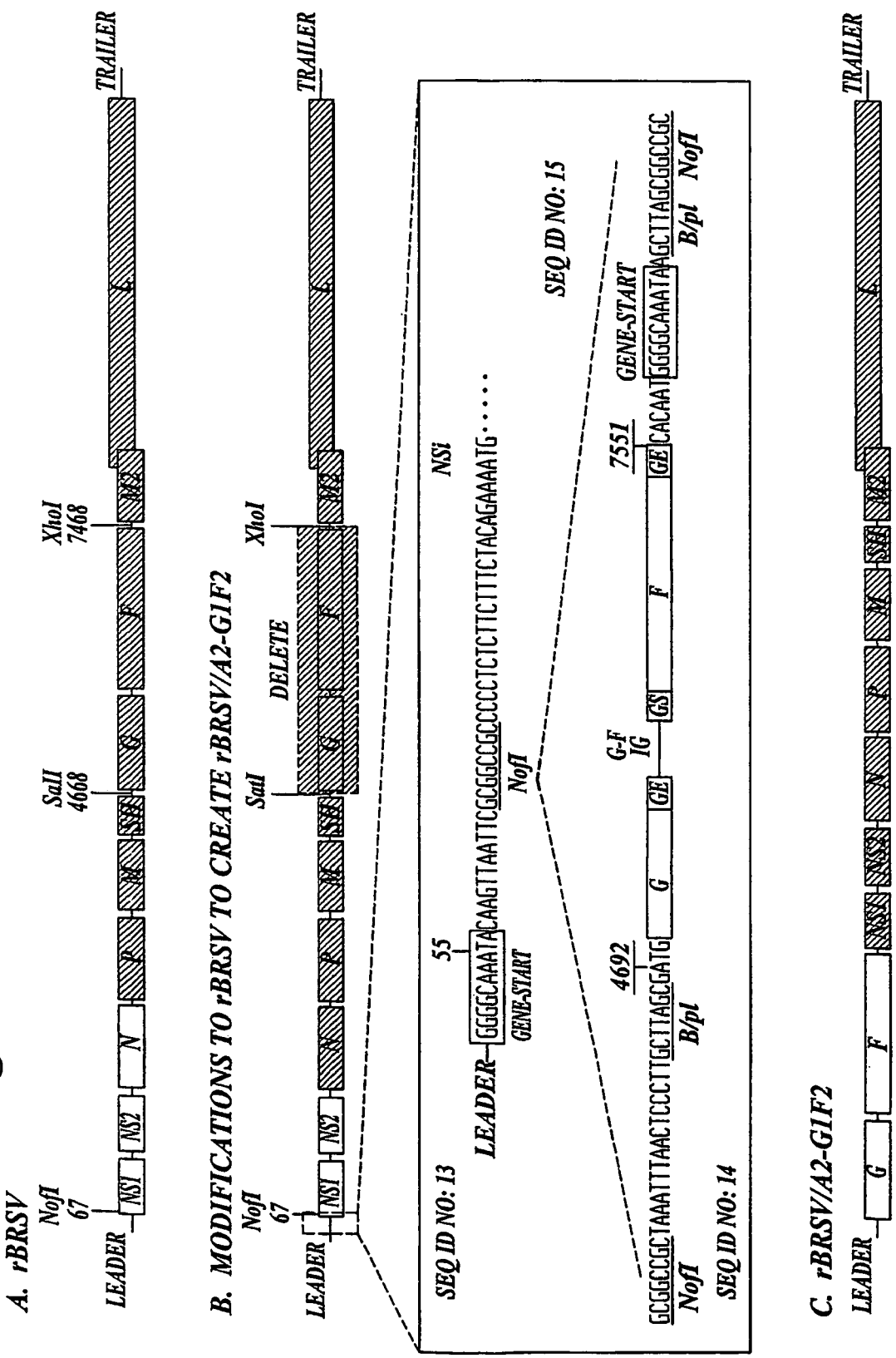

In addition to the basic substituted glycoprotein construction of rBRSV/A2, the HRSV G and F genes were shifted in the present example to a more promoter-proximal position in the rBRSV backbone relative to a wild type gene order position of the F and G genes in the BRSV genome. More specifically, the F and G genes were moved from their usual location relative to the promoter, namely gene positions 7 and 8, respectively, to positions 1 and 2, respectively. To achieve this objective, complete infectious rBRSV was constructed in which nucleotide substitutions were made to create unique NotI, SalI and XhoI sites at positions 67, 4,673 and 7,471, respectively (FIG. 6, panel A) (see also, Buchholz et al., *J. Virol.* 73:251-259, 1999; Buchholz et al., *J. Virol.* 74:1187-1199, 2000, incorporated herein by reference). The NotI site is contained within the upstream nontranslated region of the BRSV NS1 gene, and the SalI and XhoI sites are in intergenic regions. Digestion of the rBRSV antigenomic cDNA with SalI and XhoI excised the BRSV G and F genes in their entirety and created compatible cohesive ends that were ligated (FIG. 6, panel B). This resulted in an rBRSV antigenomic cDNA lacking the G and F genes and containing a 64-nucleotide SH-M2 intergenic region with the following sequence:

TTAAACTTAAAAATGGTTTATGtcgaG-GAATAAAATCGATTAACAACCAATCAT TCAAAAAGAT (SEQ ID NO: 6) (the tetranucleotide cohesive ends of the original cleaved SalI and XhoI sites are in small case). For comparison, the naturally-occurring BRSV F-M2 intergenic sequence is 55 nucleotides in length.

A cDNA containing the HRSV G and F genes was prepared by PCR with mutagenic primers used to modify the cDNA ends. Specifically, PCR was used to amplify nucleotides 4692-7551 of the complete HRSV antigenomic cDNA (spanning from the ATG of the G ORF to the end of the F gene-end signal), and the primers were designed to add, immediately after the F gene-end signal, the first 6 nucleotides of the F-M2 IG followed by a copy of the NS1 gene-start signal. The PCR primers also were designed to add a BlpI site and an NotI site each on both ends of the cDNA. The sequence of the cDNA fragment that was subjected to PCR was confirmed by dideoxynucleotide sequencing. This cDNA was then inserted as a NotI fragment into the unique NotI site of the rBRSV antigenomic cDNA lacking the G and F genes as described above. A correct recombinant was identified by restriction fragment mapping, and was designated rBRSV/A2-G1F2. The structure of the encoded genomic RNA is shown in FIG. 6, panel C. As shown, in this cDNA the G and F genes were moved from positions 7 and 8 relative to the promoter to positions 1 and 2.

A plasmid encoding the antigenomic RNA of rBRSV/A2-G1 F2 was transfected, together with plasmids encoding the N, P, M2-1 and L support proteins, into BSR T7/5 cells, which stably express the T7 RNA polymerase, as described above (see also, Buchholz et al., *J. Virol.* 73:251-259, 1999; Buchholz et al., *J. Virol.* 74:1187-1199, 2000, each incorporated herein by reference), and infectious virus was recovered. The recovered rBRSV/A2-G1F2 virus was compared to rBRSV, rHRSV (also called rA2) and rBRSV/A2 with regard to the efficiency of multicycle growth in human HEp-2 cells and bovine MDBK cells. As described above (see also, Buchholz et al, *J. Virol.* 74:1187-1199, 2000, incorporated herein by reference), rHRSV grows much more efficiently than rBRSV in HEp-2 cells, and the rBRSV/A2 virus grows with an efficiency intermediate between that of each parent. As shown in FIG. 7, the efficiency of replication of rBRSV/A2-G1F2 was indistinguishable from that of rBRSV/A2. Thus, unexpectedly, the change in the location of the G and F genes did not reduce the efficiency of growth in vitro, which novel result allows for efficient production of RSV vaccine virus.

Figure 8:
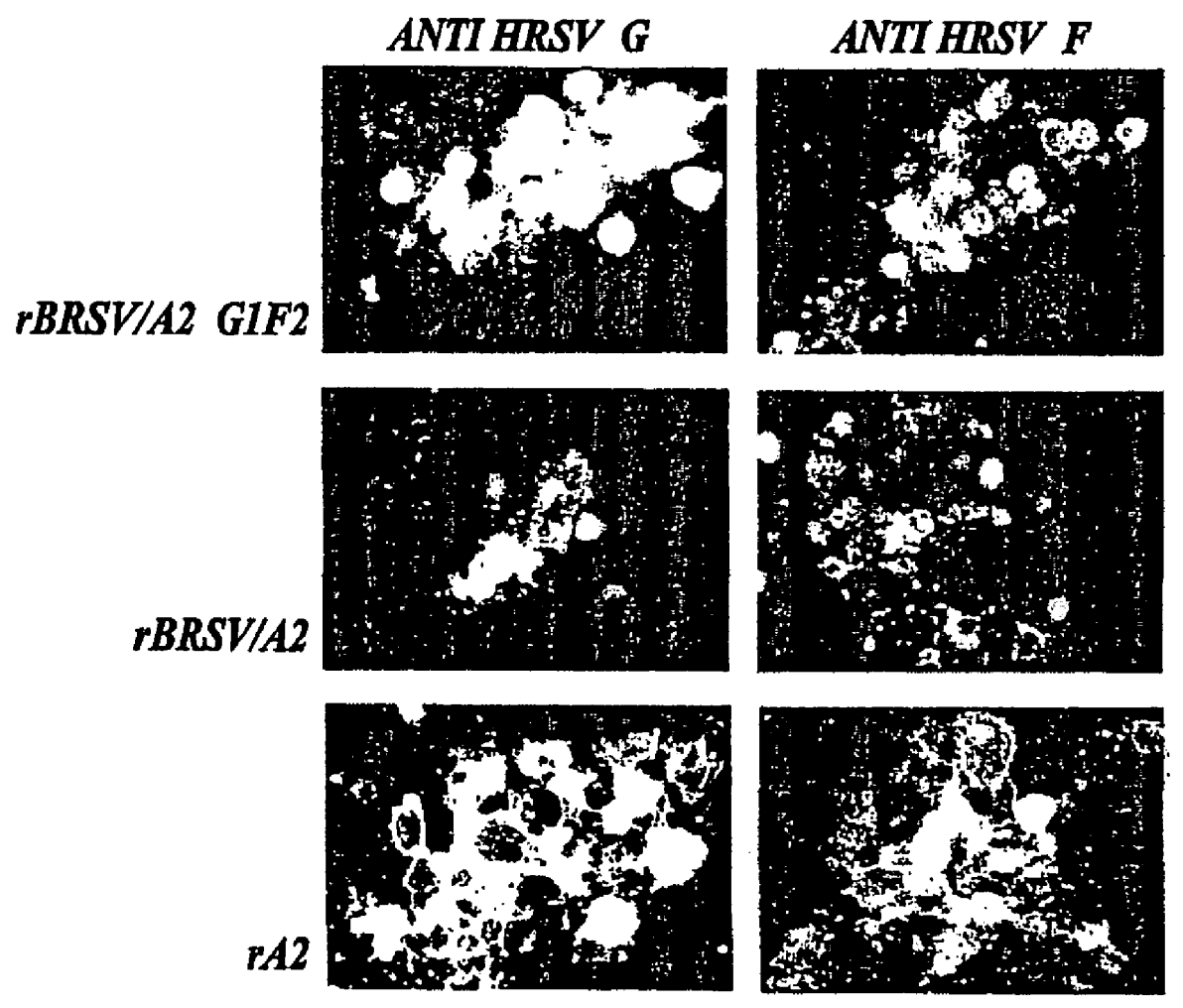

Immunofluorescence was performed on HEp-2 cells infected with wt HRSV or the chimeric viruses rBRSV/A2 or rBRSV/A2-G1F2. This was performed using two monoclonal antibodies specific to the HRSV G or F proteins, namely 021/01G and 44F, respectively (Lopez et al., *J. Virol.* 72:6922-6928, 1998; Melero et al., *J. Gen. Virol.* 78:2411-2418, 1997, each incorporated herein by reference). The staining was done with each monoclonal antibody individually. Although this assay is only semi-quantitative, it has been previously determined that the assay distinguishes reliably between wt rBRSV and rBRSV/A2 (the latter bearing the HRSV G and F genes in the normal genome location in the rBRSV backbone). In particular, wt HRSV gives a very strong, extensive pattern of immunofluorescence indicative of efficient and extensive antigen expression, while rBRSV/A2 gives a weaker, more diffuse, less extensive pattern (Buchholz et al., *J. Virol.* 74:1187-1199, 2000, incorporated herein by reference). A comparable assay conducted for rBRSV/A2-G1F2 (FIG. 8), shows that the pattern of immunofluorescence for this promoter-shifted chimeric virus was very similar to that of wt BRSV. This result is consistent with increased expression of the G and F glycoproteins. At the same time, the cytopathic effect associated with rBRSV/A2-G1F2 was reduced compared to wt HRSV, and more closely resembled that of rBRSV/A2 (Buchholz et al., *J. Virol.* 74:1187-1199, 2000, incorporated herein by reference). Specifically, rBRSV/A2 and rBRSV/A2-G1F2 induced fewer and smaller syncytia.

Thus, the present example documents modification of the rBRSV/A2 human-bovine chimeric RSV virus, which contains the genes for the major protective antigens of HRSV, the G and F proteins, in the background of BRSV which is strongly attenuated for replication in the respiratory tract of primates. The rBRSV/A2 virus has a strong host range restriction that renders it highly attenuated in primates. Since the present gene position-shifted rBRSV/A2-G1F2 virus bears the same constellation of BRSV genes in its genetic background, it is likely to share this strong host range restriction phenotype, thereby increasing the expression of the two major protective antigens. The increased expression of these two protective antigens in vivo is further expected to increase the immunogenicity of this virus. Thus, the present example modified and improved the rBRSV/A2 virus by moving the HRSV genes to a promoter proximal location. A positional shift of this magnitude, i.e., where the G and F genes were moved from wild type positions 7 and 8 relative to the promoter to new positions 1 and 2, has not been described previously.

EXAMPLE IV

Construction of a Chimeric BRSV/HRSV with Envelope-Associated M, G and F Proteins Derived from HRSV The present example demonstrates yet another gene position-shifted RSV generated within a human-bovine chimeric background which involves modification of an antigenic chimeric virus resembling the rBRSV/A2 chimera (having the HRSV G and F protective antigen genes in a BRSV host-range-attenuated background), described above. Both BRSV and HRSV have 4 envelope-associated proteins: the G and F glycoproteins which are the major protective antigens; the small hydrophobic SH protein of unknown function which does not appear to be a neutralization or protective antigen for HRSV (Whitehead et al., *J. Virol.* 73:3438-3442, 1999; Connors et al., *J. Virol.* 65:1634-1637, 1991, each incorporated herein by reference); and the nonglycosylated internal matrix M protein, which is not a protective antigen but is important in virion assembly (Teng and Collins, *J. Virol.* 72:5707-16, 1998, incorporated herein by reference).

In this example, a BRSV/HRSV chimeric virus was constructed in which all four BRSV envelope-associated protein genes were deleted, namely BRSV M, SH, G and F, and in which three HRSV envelope-associated protein genes, namely M, G and F, were inserted in their place. This yields a promoter-proximal gene shift of the F and G glycoprotein genes by the distance of one gene, corresponding to the length of the SH gene.

The above-described rBRSV/A2 construct (see also, Buchholz et al., *J. Virol.* 74:1187-1199, 2000, incorporated herein by reference) was modified to contain a unique MluI site at position 3204, within the intergenic region between the P and M genes (FIG. 9, panel A; P-M IG). This involved the introduction of 5 nucleotide substitutions. Nucleotide sequence position numbers are relative to the complete rBRSV antigenome (Buchholz et al., *J. Virol.* 73:251-259, 1999; Buchholz et al., *J. Virol.* 74:1187-1199, 2000; GenBank accession number AF092942 or complete rHRSV antigenome in Collins et al., *Proc. Natl. Acad. Sci. USA* 92:11563-11567, 1995; each incorporated herein by reference), and sequence position numbers that refer to the HRSV sequence are underlined. The MluI-SalI fragment was excised and replaced by the MluI-SalI fragment bearing the M gene.

Referring to FIG. 9, panel B, a cDNA containing the HRSV M gene was amplified and modified by PCR using primers that introduced changes to the ends of the cDNAs. Specifically, the M cDNA was modified so that its upstream end contained an MluI site, followed by the last nucleotide of the P-M intergenic region (which is the same in HRSV and BRSV), followed by the complete HRSV M gene, followed by the first 4 nucleotides of the BRSV SH-G intergenic region, followed by a SalI site. The sequence of this cDNA was confirmed to be correct in its entirety. It was digested with MluI and SalI and cloned into the MluI-SalI window of the rBRSV antigenome. This resulted in rBRSV/A2-MGF. As shown in FIG. 9, panel C, this chimera contained a backbone of six BRSV genes, namely NS1, NS2, N, P, M2 and L, and three HRSV envelope-associated protein genes, namely M, G and F.

This antigenomic plasmid was transfected, together with plasmids encoding the N, P, M2-1 and L support proteins, into BSR T7/5 cells, which stably express the T7 RNA polymerase, as described in detail previously (Buchholz et al., *J. Virol.* 73:251-259, 1999; Buchholz et al., *J. Virol.* 74:1187-1199, 2000, each incorporated herein by reference), and infectious virus was recovered. Thus, the present example also demonstrates that gene position-shifted RSVs containing a gene deletion resulting in a promoter proximal shift of the G and F genes can be readily produced and recovered. This and other gene position-shifted RSVs will be analyzed for levels of replication and antigen expression, as well as growth, immunogenicity and protective efficacy in vivo to select suitable vaccine candidates in accordance with the methods described herein.

EXAMPLE V

Construction and Recovery of Additional BRSV/HRSV Chimeric Viruses Containing Nonstructural and/or Envelope-Associated Proteins of HRSV Substituted into the BRSV Backbone Additional BRSV/HRSV chimeric viruses were constructed that contained HRSV nonstructural NS1 and NS2 genes and/or envelope-associated M, SH, G and/or F genes substituted into the BRSV backbone. Most of these chimeric viruses contained G and F genes derived from HRSV, a desirable feature since these encode the major protective antigens and would be important for an effective HRSV vaccine.

In certain exemplary viruses, the BRSV NS1 and NS2 genes were replaced by their HRSV counterparts. NS1 and NS2 have recently been shown to be antagonists of the type I interferon-mediate antiviral state (Schlender, et al., *J. Virol.*, 74:8234-42, 2000, incorporated herein by reference) and substitution of these genes offers a way of modifying the growth properties and virulence of a vaccine virus. This is due to the general finding that interferon antagonists tend to be host specific (Young, et al., *Virology*, 269:383-90, 2000; Didcock, et al., *J. Virol.*, 73:3125-33, 1999; Didcock, et al., *J. Virol.*, 73:9928-33, 1999, each incorporated herein by reference). Thus, inclusion of BRSV-specific NS1 and NS2 genes in a vaccine virus would improve its growth in bovine cells but would constitute an attenuating mutation with regard to growth in primate cells and in the human vaccine.

Conversely, HRSV-specific NS1 and NS2 genes would offer a way of improving the growth of a vaccine virus in human cells. Thus, this provides a new method for manipulating the growth properties and reactogenicity of a vaccine virus. In another virus, the complete constellation of HRSV-specific membrane associated genes, namely M, SH, G and F, was placed in the BRSV backbone. Since the various proteins of the virus particle are thought to interact in various ways during gene expression, genome replication, and virion production, the ability to make a variety of combinations provides a rich source of vaccine candidates.

Finally, this additional exemplary panel of viruses contained examples of genes that were substituted without a change in gene order, others in which the gene order of the substituted viruses was altered, as well as ones in which some of the substituted genes did not have a change in order with regard to the BRSV backbone whereas others did. Thus, this panel provided a stringent test of the ability to manipulate cDNA-derived virus to make a wide array of chimeric viruses, and to recover viable viruses with altered and desirable biological properties.

Figure 10:
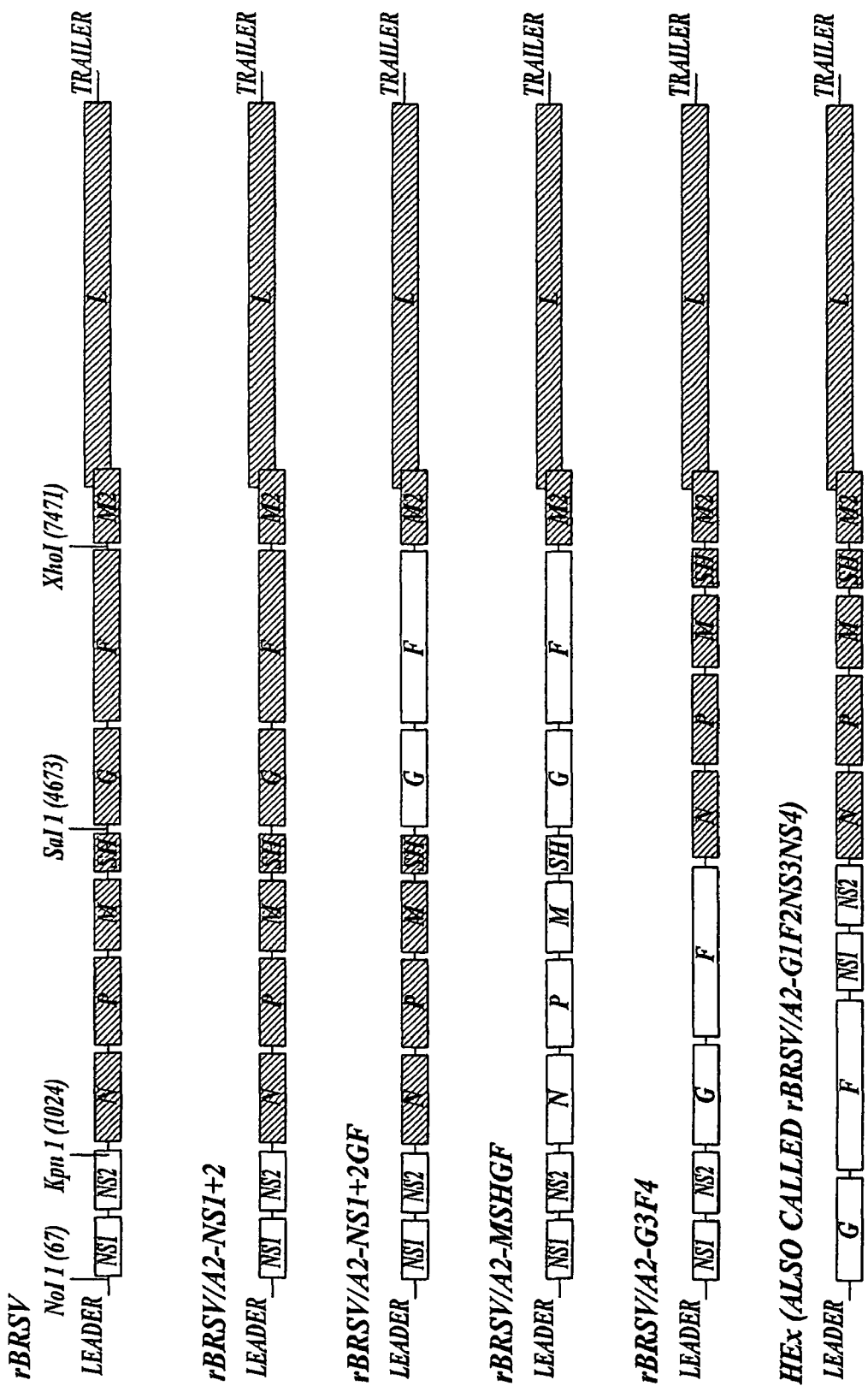

A BRSV/HRSV chimeric virus was constructed in which the NS1 and NS2 genes of the rBRSV backbone were removed and replaced with the NS1 and NS2 genes of HRSV, creating a virus called rBRSV/A2-NS1+2 (FIG. 10, second construct from the top). The backbone for this construction was the rBRSV antigenomic cDNA which had been modified to contain the unique NotI, KpnI, SalI and XhoI sites illustrated in FIG. 10 (top construct) and described in detail previously (Buchholz, et al., *J. Virol.*, 73:251-9, 1999; Buchholz, et al., *J. Virol.*, 74:1187-1199, 2000, each incorporated herein by reference). The HRSV NS1 and NS2 coding sequences were amplified by PCR as a single fragment which spanned positions 75 to 1036 of the complete HRSV antigenomic sequence and included the HRSV NS1 ORF, the NS1/N2 gene junction, and the NS2 ORF. The upstream end of the fragment also contained an added NotI site immediately before the HRSV sequence and a BlpI site added in the non-translated sequence upstream of the NS1 ORF at HRSV position 91. The downstream end of the PCR cDNA contained a KpnI site immediately following the HRSV sequence. This PCR product was cloned and its sequence confirmed. It was then inserted as a NotI-KpnI fragment into the corresponding window of the rBRSV backbone.

Another BRSV/HRSV chimeric virus was made in which the following four genes in rBRSV were replaced with their HRSV counterparts: NS1, NS2, G and F. This virus is designated rBRSV/A2-NS1+2GF (FIG. 10, third construct from the top) and was deposited with the Amer. Type Cult. Coll. (10801 University Blvd., Manassas, Va. 20110-2209) on Oct. 27, 2009 as rBRSV/A2-NS1+2GF 28, P2 vero, and has been assigned ATCC accession number PTA-10445. This construct was made by combining fragments from rBRSV/A2-NS 1+2 and the previously described rBRSV/A2 (see, FIGS. 7 and 8; U.S. Patent application Ser. No. 09/602,212; Buchholz, et al., *J. Virol.*, 3:11 87-1 199, 2000, each incorporated herein by reference), which is optionally termed herein rBRSV/A2-GF. Specifically both constructs contained a XmaI site in the plasmid sequence upstream of the leader region and the KpnI site illustrated in FIG. 10. The XmaI-KpnI fragment of rBRSV/A2-NS 1+2 was transferred into the corresponding window of the rBRSV/A2-GF plasmid. The virus rBRSV/A2-NS1+2 was also deposited with the Amer. Type Cult. Coll. (10801 University Blvd., Manassas, Va. 20110-2209) on Oct. 27, 2009 as rBRSV/A2-NS1+2 16/1, P2 vero, and has been assigned ATCC accession number PTA-10444.

Another BRSV/HRSV chimeric virus was made in which the following four genes in rBRSV were replaced by their HRSV counterparts: M, SH, G and F. This virus was designated rBRSV/A2-MSHGF (FIG. 10, fourth construct from the top) and was deposited with the Amer. Type Cult. Coll. (10801 University Blvd., Manassas, Va. 20110-2209) on Oct. 27, 2009 and has been assigned ATCC accession number PTA-10446. This involved a rBRSV backbone in which a MluI site was added in addition to the P-M intergenic region (see FIG. 9). Thus, the inserted HRSV sequence had as its upstream and downstream boundaries the MluI and XhoI sites shown in FIG. 9. This HRSV insert, bearing the M-SH-G-F sequence of HRSV flanked by MluI and XhoI sites, was prepared by PCR, and the resulting product was cloned and its sequence confirmed. The MluI-XhoI fragment was then cloned into the corresponding window in the rBRSV backbone.

Another BRSV/HRSV chimeric virus was made in which the G and F genes were replaced by their HRSV counterpart placed in the third and fourth positions in the rBRSV backbone. This virus was designated rBRSV/A2-G3F4 (FIG. 10, fifth construct from the top). For this construction, PCR was used to amplify the HRSV G and F ORFs. The PCR primers were designed to add to the upstream end of G the following features: a Kpn l site, a BRSV gene end signal (5'-AGTTATT-TAAAAA) and a three nt intergenic sequence (CAT), which was then followed by the HRSV G and F genes. The downstream end of the amplified fragment ended in the downstream nontranslated region of the HRSV F gene, at HRSV antigenomic position 7420, followed by an added Kpn I site. This PCR product was cloned and its sequence confirmed. The Kpn I fragment bearing the HRSV G and F sequence was then cloned into the Kpn I site of the rBRSV cDNA lacking the G and F genes as shown in FIG. 6, panel B. A recombinant containing the insert in the correct orientation was identified by restriction analysis.

Another BRSV/HRSV chimeric virus was made in which the following genes were replaced in the rBRSV backbone:

NS1, NS2, G and F, with the G and F genes in the promoter-proximal position. This construct is designated HEx, or rBRSV/A2-G1F2NS3NS4 (FIG. 10, bottom construct). This chimera was generated by modifying rBRSV/A2-NS1+2 to replace the BRSV G and F genes by their HRSV counterparts in the first and second position, in the same way as described above for the construction of rBRSV/A2-G1F2 (Example III, FIG. 6, panel B). Specifically, the BRSV G and F genes were excised from the rBRSV/A2-NS1+2 antigenomic cDNA by digestion with SalI and XhoI, as described above (Example III). Subsequently, a NotI fragment containing the HRSV G and F genes as described above (Example III, FIG. 6, panel B) was cloned into the singular NotI site which is located immediately before the HRSV sequence in the NS1 noncoding region of the rBRSV/A2-NS1+2 antigenomic cDNA. A recombinant containing the insert in the correct orientation was identified by restriction analysis.

Each of the viruses listed above was readily recovered from cDNA, and in no case to date was a virus designed that could not be recovered.

Figure 11:
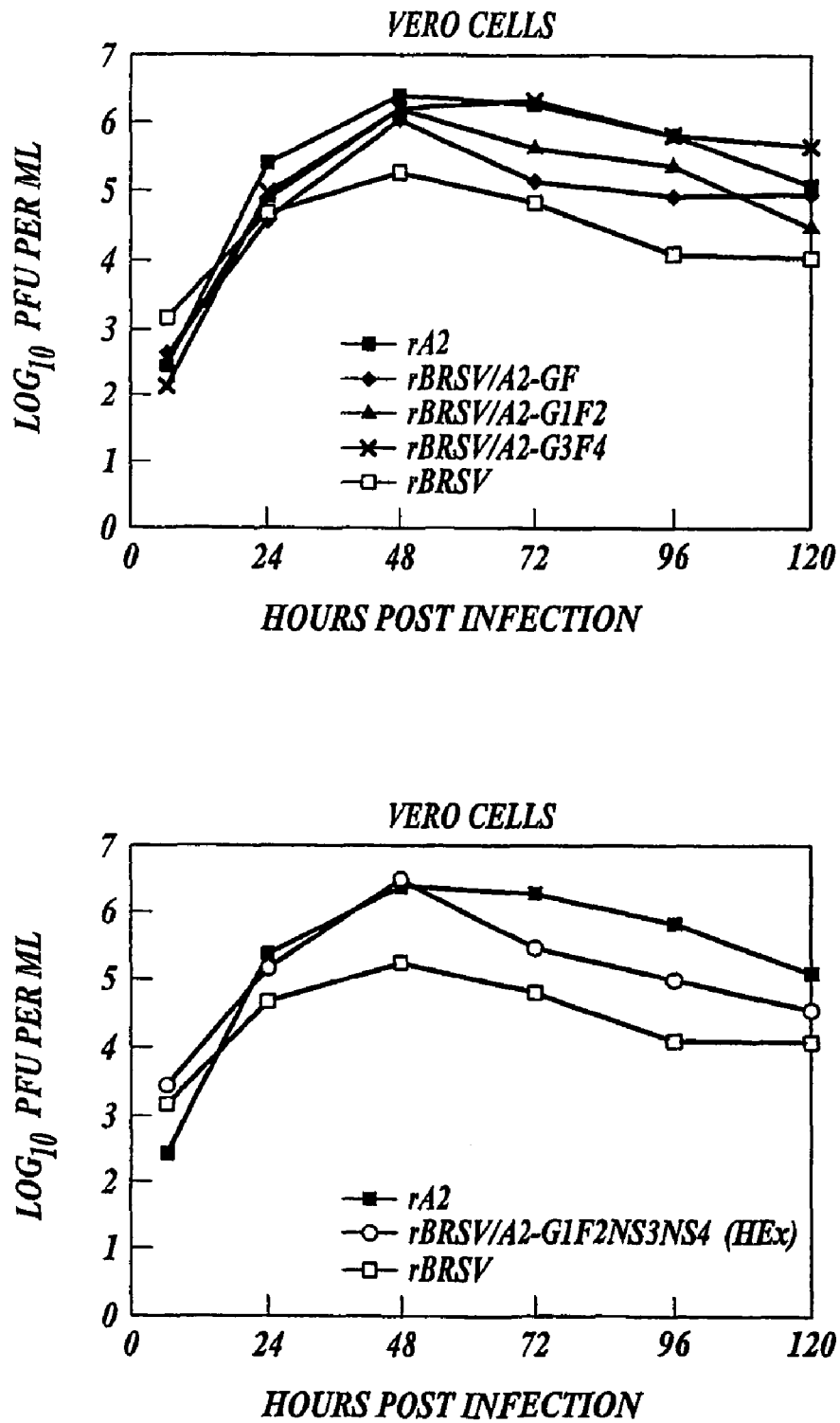

The new rBRSV/A2-G3F4 and HEx viruses were compared for growth efficiency in vitro in parallel with the previously-tested rBRSV/A2-GF and rBRSV/A2-GF viruses (as noted above, the last virus was called rBRSV/A2 in previous examples but was renamed here for clarity compared to the new constructions). Monolayer cultures of Vero cells were infected at a multiplicity of infection of 0.1 and incubated at 37° C. Aliquots were taken at the time points shown in FIG. 11, and the virus titer was determined by plaque assay. Under these conditions, BRSV replicates somewhat less efficiently than HRSV, reflecting its host range restriction in primate cells. As shown in FIG. 11, top panel, the rBRSV/A2-G3F4 exhibited improved growth in vitro compared to the other chimeric viruses and rBRSV. Indeed, its growth efficiency was similar to that of recombinant HRSV (rA2). Thus, the growth of the rBRSV virus was improved by replacing the BRSV G and F genes with their HRSV counterparts (as in rBRSV/A2-GF), and was further improved by placing the HRSV genes in the promoter-proximal position (as in rBRSV/A2-G1F2), and was yet again further improved by placing the HRSV G and F genes in positions 3 and 4 (as in rBRSV/A2-G3F4). These results demonstrate how the properties of viruses within the invention can be systematically adjusted by manipulating the origin and order of the viral genes.

The HEx virus was evaluated in the same way (FIG. 11, bottom panel). Its growth was intermediate to that of rBRSV and rA2, indicating that this four-gene replacement retained replication fitness in vitro and indeed exceeded that of its rBRSV parent. It should be noted that Vero cells lack the structural genes for type I interferons, and hence interferon-specific effects cannot be evaluated. On the other hand, Vero cells are a useful substrate for large scale vaccine production, and efficient growth in these cells is an important feature for a vaccine virus.

The panel of rBRSV/HRSV chimeric viruses was further evaluated for growth on the basis of plaque size in HEp-2 and MDBK cells, the former of human origin and the latter bovine (FIG. 12, top and bottom panels, respectively). This comparison also included chimeric viruses described in previous examples, namely rBRSV/A2-GF (previously called rBRSV/A2), rBRSV/A2-MGF, and rBRSV-G1F2. In HEp-2 cells, rHRSV produced larger plaques than did rBRSV, consistent with the host range restriction (FIG. 12, top panel). This discussion first considers those viruses in which the NS1 and NS2 genes remained of BRSV origin. In this group, the rBRSV/A2-G3F4, rBRSV/A2-G1F2 and rBRSV/A2-GF viruses produced plaques that were intermediate in size between HRSV and BRSV and which decreased in the order given. This is fully consistent with growth kinetic data, and confirms the idea that the introduction of the HRSV G and F genes into the rBRSV backbone improves its growth in HEp-2 cells, and that further improvement can be obtained by modifying the positions of these genes. The rBRSV/A2-MGF and rBRSV/A2-MSHGF viruses produced plaques that were smaller than those of rBRSV. While this example shows that these viruses can be recovered and manipulated, further characterization in vitro and in vivo will be needed to determine the full characterization of their growth properties.

Growth in HEp-2 cells was also examined for those viruses in which the NS1 and NS2 genes were of HRSV origin. Specifically, pairs of viruses were compared that were identical except for the origin of the NS1 and NS2 genes. These pairs are listed next, ordered such that the virus having NS1 and NS2 genes of HRSV is in each pair: rBRSV versus rBRSV/A2-NS1+2; rBRSV/A2-GF versus rBRSV/A2-NS1+2GF; rBRSV/A2-G1F2 versus HEx. In each case, the presence of the NS1 and NS2 genes of HRSV origin provided an increase in plaque size, indicating a modulation of the host range restriction. This illustrates how the origin of the NS1 and NS2 genes can be selected as a method of predictably modulating growth properties of an HRSV vaccine. In this example, the two genes were manipulated as a pair, although it is clear that they can also be manipulated singly according to the teachings herein.

The characteristics of these viruses in MDBK bovine cells also is shown in FIG. 12, bottom panel. The host range restriction in these cells is reversed in comparison with the preceding comparison in HEp-2 cells, such that BRSV produced larger plaques than HRSV. The presence of HRSV G and F genes in the rBRSV backbone did not have much effect on growth, while the presence of NS1 and NS2 genes of HRSV origin attenuated the virus, presumably because these HRSV-derived interferon antagonists operated less efficiently in bovine cells. Since bovine cells and bovine hosts are not an important target for these candidate HRSV vaccines, these findings with MDBK cells serve mainly to provide a clearer understanding of the functions of these proteins and their contribution to growth.

In summary, the foregoing example illustrates how a panel of recombinant HRSV vaccine candidates can be readily generated that exhibit a spectrum of desired growth properties. Clinical evaluation of selected candidates will provide benchmarks to guide optimization of vaccine candidates by the methods of this invention. Previous studies indicated that rBRSV and its rBRSV/A2-GF derivative were over attenuated in chimpanzees, although the latter virus was an improvement over rBRSV (Buchholz, et al., *J. Virol.*, 74:1187-1199, 2000, incorporated herein by reference). Thus, the further, graded improvements in growth that were obtained here represent a substantial advance toward optimization of RSV vaccine recombinants.

EXAMPLE VI

Construction and Recovery of Additional BRSV/HRSV Chimeric Viruses Containing Substitutions of the N and/or P Gene in BRSV Backbones with NS1 and NS2 Proteins of HRSV or BRSV Origin.

Human parainfluenza virus type 3 (HPIV3) has a bovine counterpart (BPIV3) that exhibits a host range restriction in primates and thus provides the basis for developing attenuated HPIV3 vaccines based on HPIV3/BPIV3 chimeric viruses. One promising chimera consists of the HPIV3 backbone in which the N ORF was replaced by its BPIV3 counterpart. Remarkably, this chimeric virus replicates efficiently in cell culture and exhibits an attenuation phenotype in primates (Bailly, et al., *J. Virol.*, 74:3188-95, 2000, incorporated herein by reference).

Within the present example, investigations were undertaken to determine whether individual BRSV genes could be replaced by their HRSV counterparts. Specifically, the N gene and the P gene were individually substituted (FIG. 13A). Additional studies were undertaken to determine whether two genes could be replaced together. Finally, additional investigations were conducted to determine if gene replacements also could be made in a backbone containing the HRSV NS1 and NS2 genes (FIG. 13B). It should be noted that these substitutions were made in the rBRSV backbone, bearing the BRSV G and F genes. In order to make an optimal HRSV vaccine, these would be replaced by their HRSV counterparts, inserted either in the natural gene order positions or in other positions, following the teachings set forth herein above which demonstrate that such substitutions can be readily made, and indeed generally provide improved growth properties.

A BRSV/HRSV chimera was constructed in which the BRSV N coding sequence was replaced by that of HRSV. This chimera is designated rBRSV/A2-N (FIG. 113A). For this construction, an Aat II site was engineered into the rBRSV N gene at nt 2305-2310, which is located within the last three codons of the N ORF. The substitution was silent at the amino acid level. The same site was engineered into the HRSV N ORF of the HRSV antigenomic cDNA. In addition, the HRSV antigenomic cDNA was modified so that antigenomic nt 1037-1042 in the downstream nontranslated region of NS2 were changed to a Kpn I site. This Kpn I-Aat II HRSV fragment was cloned into the corresponding window of rBRSV, transferring most of the N ORF. The very last few codons of the N ORF of BRSV and HRSV have the same amino acid coding assignments, and so the few nt of BRSV N ORF that remain contribute to encode a complete HRSV N protein.

A BRSV/HRSV chimera was constructed in which the BRSV P gene was replaced by its HRSV counterpart. This chimera is designated rBRSV/A2-P (FIG. 13A). This employed the above-mentioned Aat II site as well as a previously-described Mlu I site (see FIG. 9). Transfer of this HRSV fragment to the corresponding window of rBRSV transferred the complete P gene. As indicated above, the few N ORF nt that were transferred in this fragment have the same coding assignment in BRSV and HRSV.

A BRSV/HRSV chimera was constructed in which the above-mentioned N and P sequences of HRSV were transferred to rBRSV, resulting in rBRSV/A2-NP (FIG. 13A). This employed the Kpn I and Mlu I sites mentioned above.

The same transfers also were made into a rBRSV backbone containing the HRSV NS1 and NS2 genes, namely the rBRSV/A2-NS1+2 backbone described in the previous example. This resulted in rBRSV/A2-NS1+2N, rBRSV/A2-NS1+2P, and rBRSV/A2-NS1+2NP (FIG. 13B).

Each of the foregoing recombinant viruses was readily recovered from cDNA. The rBRSV/A2-P virus replicated in MDBK cells comparably to wild-type rBRSV, whereas the replication of the rBRSV/A2-N was approximately 10-fold lower and that of the rBRSV/A2-NP virus was intermediate between these two. Thus, a spectrum of growth properties was obtained. Following the methods described above, these viruses can be modified to bear HRSV G and F genes. In addition, comparable gene substitutions can be made in the rHRSV backbone. Namely, the HRSV N and/or P gene can be substituted by the BRSV counterpart. The ability to make these substitutions in the context of substitutions of the NS1 and NS2 genes offers further flexibility in obtaining an optimal level of vaccine production in vitro and attenuation and immunogenicity in the human vaccinee.

As indicated by the foregoing examples, genes to be transferred in gene position-shifted RSV can be selected that are likely to interact functionally of structurally based on available knowledge of RSV structure/function. These exchanges and other modifications within gene position-shifted RSV are further simplified by the fact that proteins that interact are juxtaposed in the genome, for example the N and P nucleocapsid proteins, the M, SH, F and G envelope proteins, and the M2-1, M2-2 and L polymerase components. Thus, additional candidate vaccine strains according to the invention can be achieved, for example, by incorporating two or more juxtaposed genes, e.g., selected from N and P, two or more of the M, SH, F and G envelope genes, or two or more of the M2-1, M2-2 and L genes, together as a heterologous insert or substitution unit in a recipient or background genome or antigenome.

For example, the M and SH genes can be replaced together in rBRSV/A2 with their HRSV counterparts. This will result in a virus in which the viral envelope proteins (G, F, SH and M) are all of HRSV, while the internal proteins are of BRSV. This can be followed, as needed, by replacement of additional BRSV genes with their human counterparts, for example, N and P as another pair, NS1 and NS2 as another, and M2-1, M2-2 and L as another group. The juxtaposition of each pair of genes will simplify the substitutions. At the same time, the converse approach of inserting individual BRSV genes into HRSV, leaving the HRSV G and F antigenic determinants undisturbed, will also yield desired vaccine candidates within the invention. For example, one or more of the N, P, M2-1 and M genes of a human RSV can be individually replaced by their bovine counterparts. Recovered recombinant viruses are then evaluated for the attenuation phenotype in cell culture, rodents, and nonhuman primates, as exemplified herein. In this manner, the invention provides for identification of candidate human-bovine chimeric RSV vaccine viruses having desired levels of attenuation and protective efficacy for treatment and prophylaxis of RSV in various subjects.

EXAMPLE VII

Improved in vitro Replication of RSV Vaccine Viruses Having a Partial Gene Deletion In accordance with the foregoing description, it has been shown that the efficiency of in vitro replication of RSV is sensitive to changes in the nucleotide length of the genome. With regard to increases in length, one type of modification to adjust growth phenotype of recombinant RSV can involve the insertion of an additional gene encoding a foreign protein. For example, the coding sequences for bacterial chloramphenicol acetyl transferase (CAT), firefly luciferase, murine interferon gamma (IFNg), murine interleukin 2 (IL-2), and murine granulocyte macrophage colony stimulating factor (GM-CSF) have been inserted individually into the G-F intergenic region. Each of these insertions had the effect of reducing the efficiency of virus growth in vitro. In one instance, insertion of a CAT transcription cassette of approximately 0.76 kb into the G-F intergenic region reduced virus growth in vitro 20-fold. The lymphokines were of murine origin and would not be expected to be active in the HEp-2 cells of human origin. Also, the various inserts of comparable size had an effect of comparable magnitude in reducing RSV growth in vitro. The inhibition reported in these studies may be attributable to the addition of sequence per se, as opposed to the expression of the various encoded foreign proteins.

Insertion of a 1.75 kb luciferase cassette into this same intergenic region had a much greater inhibitory effect on virus replication (greater than 50-fold reduction), suggesting that larger inserts are more inhibitory. On the other hand, there was some evidence that this effect also might depend on the location of the insert in the genome. For example, the insertion of a 0.8 kb transcription cassette into the noncoding region of the NS1 gene, placing it in a promoter-proximal position, had only a marginal inhibitory effect on virus growth (Hallak, et al., *J. Virol.*, 74:10508-13, 2000, incorporated herein by reference). It remains uncertain whether the observed effect was due to the increase in nucleotide length alone, or due to the addition of another mRNA-coding unit, or both.

In other examples, increases in the nt length of recombinant RSV were made in a single intergenic region. The naturally-occurring RSV intergenic regions that 110 have been analyzed to date range in length from 1 to 56 nt. In a recombinant virus lacking the SH gene, the M-SH intergenic region was increased up to 160 nt with a marginal inhibitory effect on growth.

In additional examples, the RSV genome is decreased to yield a desired effect on viral phenotype. In selected embodiments, one or more genes from the set NS1, NS2, SH, G and M2-2 were deleted singly, or in certain combinations, from recombinant virus without ablating viral infectivity. Each deletion results in a loss of expression of the deleted protein, and in most cases resulted in a reduced efficiency of viral growth in vitro and in vivo. The only exception is that the growth of the SH-deletion virus was not reduced in vitro and, in some cell lines, was marginally increased. In another example involving the construction of a chimeric virus between RSV strains A2 and B1, the intergenic region between the G and F genes was shortened from 52 nt to 5 nt (see, e.g., Whitehead, et al., *J. Virol.*, 73:9773-80, 1999, incorporated herein by reference).

A number of prior reports have discussed production of recombinant RSV with gene or intergenic sequences deleted (Bermingham and Collins, *Proc. Natl. Acad. Sci. U.S.A.*, 96:11259-64, 1999; Bukreyev, et al., *J. Virol.*, 71:8973-82, 1997; Jin, et al., *Virology*, 273:210-8, 2000; Jin, et al., *J. Virol.*, 74:74-82, 2000; Teng and Collins, *J. Virol.*, 73:466473, 1999; Teng, et al., *Journal of Virology*, 2000; Whitehead, et al., *J. Virol.*, 73:3438-42, 1999, each incorporated herein by reference). However, in each case the deletion was accompanied by modification of open reading frames or other significant genomic features, rendering uncertain the effect of the nucleotide deletion on viral phenotype.

In the present example, the effect of reducing the length of the RSV genome by deleting sequence from the downstream noncoding region of the SH gene is demonstrated. This exemplary partial gene deletion (schematically illustrated in FIG. 14) was constructed using a version of the antigenome cDNA containing an XmaI site in the G-F intergenic region, a change which of itself would not be expected to affect the encoded virus. The 141-bp XhoI-PacI window that runs from the end of the SH ORF to the SH gene-end signal was replaced with a synthetic DNA formed from the following two oligonucleotides: TCGAGTtAAtACtTgaTAAAGTAGTTAAT (SEQ ID NO: 7) and TAACTACTTTAtcAaGTaTTaAC (SEQ ID NO: 8) (parts of the XhoI and PacI restriction sites are in bold, nucleotides of the SH open reading frame and termination codon are underlined, and silent nucleotide changes are indicated in small case). The encoded virus, which was designated RSV/6120, has silent nucleotide substitutions in the last three codons and termination codon of the SH ORF and has a deletion of 112 nucleotides from the SH downstream non-translated region (positions 4499-4610 in the recombinant antigenome) that leaves the gene-end signal intact (Bukreyev, et al., *J. Virol.*, 70:6634-41, 1996; incorporated herein by reference) (FIG. 14). These point mutations and 112-nt deletion thus did not alter the encoded amino acids of any of the viral proteins, did not interrupt any of the known viral RNA signals, and did not change the number of encoded mRNAs.

The noncoding changes at the end of the SH gene were made because this region is susceptible to instability during growth in bacteria. Indeed, these changes resulted in greatly improved stability in bacteria, a property that is important for the manipulation and propagation of the antigenome plasmid. Thus, RSV/6120 provided the opportunity to examine the effect of deleting sequence from the genome in the absence of confounding secondary and tertiary effects due to alterations in encoded proteins, RNA signals, or number of encoded mRNAs. It is expected that the five point mutations made in the last few codons of the SH ORF will not affect the biological properties of the encoded virus, as evinced by studies of point mutations introduced as markers into various genes of recombinant RSV and human and bovine parainfluenza virus type 3 which are not associated with significant change in biological properties (Collins, et al., *Adv. Virus Res.*, 54:423-51, 1999; Schmidt, et al., *J. Virol.*, 74:8922-9, 2000; Schmidt, et al., *J. Virol.*, 75:4594-603, 2001; Skiadopoulos, et al., *J. Virol.*, 72:1762-8, 1998; Skiadopoulos, et al., *J. Virol.*, 73:1374-81, 1999; Whitehead, et al., *J. Virol.*, 72:4467-4471, 1998; Whitehead, et al., *J. Virol.*, 73:871-7, 1999, each incorporated herein by reference).

Figure 15C:
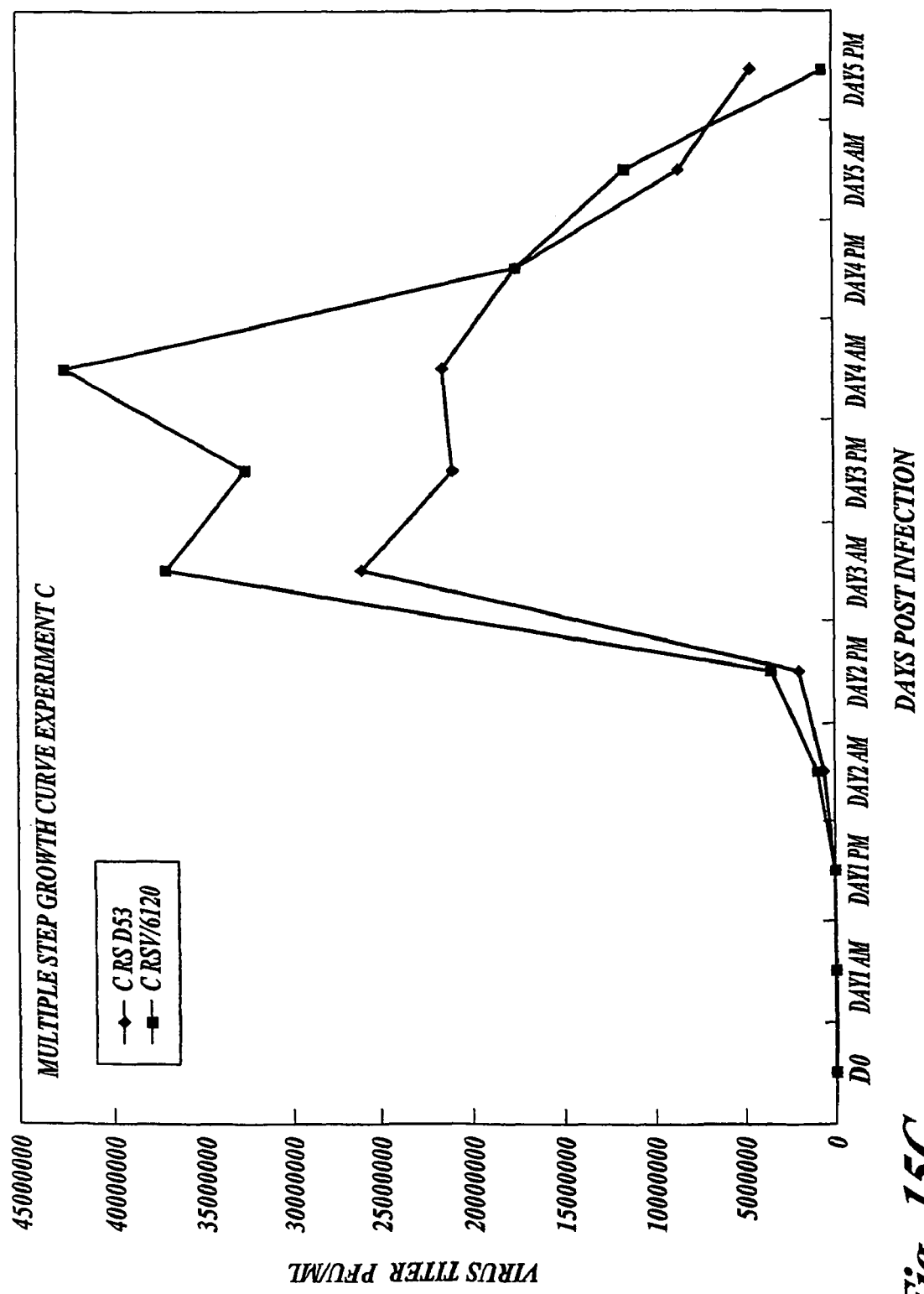

The 6120 virus was analyzed for the efficiency of multi-step growth in parallel with its full-length counterpart, called D53 in three separate sets of infections (FIGS. 15A, 15B and 15C). As shown in the figures, the peak titer of the 6120 virus was reproducibly higher than that of the D53 virus by a factor of 1.5- to 2-fold. Thus, the modifications made to the SH gene, in particular the 112-nt noncoding deletion (representing 0.7% of the genome length), resulted in a substantial increase in growth efficiency in vitro. Any increase in growth efficiency in vitro is an advantage for RSV vaccine production, since the relatively non-robust growth that is characteristic of RSV is an important problem for vaccine development and is anticipated to be a complication for vaccine production.

The specific, defined modifications described here provide a general tool that can be applied in a variety of contexts to optimize recombinant vaccine virus growth and other phenotypic characteristics. Based on the present findings, the 15.2 kb genome of RSV provides a large assemblage of target sites for modification by partial gene deletion or other nucleotide deletions. Typically, changes to be selected in this regard will not involve the 11 viral ORFs and their translation start sites (see, e.g., Kozak, *Gene*, 234:187-208, 1999, incorporated herein by reference). The viral ORFs account for more than 90% of the genome, and thus the typical selection of target sites for partial deletional modification will be within the remaining, non-translated regions (alternatively referred to as noncoding regions). In addition, target sites for nucleotide deletions in this regard will generally exclude cis-acting replication and transcription signals, including the 10-nt gene start and 12- to 13-nt gene end signal that flank each gene (see, e.g., Collins, et al., *Fields Virology*, 2:1313-1352, 1996, incorporated herein by reference), as well as an 11-nt core promoter found at the 3' end of the genome and the complement of the antigenomic promoter found at the 5' end of the genome.

The present example illustrates that, unexpectedly, the efficiency of in vitro growth by RSV can be increased substantially by removing nontranslated sequence, such as sequence flanking the viral ORFs or located between or following genes or in the 3' and 5' extragenic regions. The example demonstrates that even small deletions of sequence can yield improved viral growth. This is a highly desired result, since the improvement of growth efficiency in vitro facilitates large scale vaccine development and production.

Microorganism Deposit Information

The following materials have been deposited with the American Type Culture Collection, 10801 University Boulevard, Manassas, Va. 20110-2209, under the conditions of the Budapest Treaty and designated as follows:

| Plasmid | Accession No. | Deposit Date |
|---|---|---|
| cpts RSV 248 | ATCC VR 2450 | Mar. 22, 1994 |
| cpts RSV 248/404 | ATCC VR 2454 | Mar. 22, 1994 |
| cpts RSV 248/955 | ATCC VR 2453 | Mar. 22, 1994 |
| cpts RSV 530 | ATCC VR 2452 | Mar. 22, 1994 |
| cpts RSV 530/1009 | ATCC VR 2451 | Mar. 22, 1994 |
| cpts RSV 530/1030 | ATCC VR 2455 | Mar. 22, 1994 |
| RSV B-1 cp52/2B5 | ATCC VR 2542 | Sep. 26, 1996 |
| RSV B-1 cp-23 | ATCC VR 2579 | Jul. 15, 1997 |
| p3/7(131) | ATCC 97990 | Apr. 18, 1997 |
| p3/7(131)2G | ATCC 97989 | Apr. 18, 1997 |
| p218(131) | ATCC 97991 | Apr. 18, 1997 |

Although the foregoing invention has been described in detail by way of example for purposes of clarity of understanding, it will be apparent to the artisan that certain changes and modifications may be practice within the scope of the appended claims which are presented by way of illustration not limitation. In this context, various publications and other references have been cited within the foregoing disclosure for economy of description. Each of these references are incorporated herein by reference in its entirety for all purposes.

What is claimed is:

1. An isolated infectious RSV, which is rBRSV/A2-NS1+2, deposited with the American Type Tissue Culture Collection as accession number PTA-10444.

2. An isolated infectious RSV, which is rBRSV/A2-NS1+2GF, deposited with the American Type Tissue Culture Collection as accession number PTA-10445.

3. An isolated infectious RSV, which is rBRSV/A2-MSHGF, deposited with the American Type Tissue Culture Collection as accession number PTA-10446.

4. An isolated polynucleotide molecule comprising a recombinant RSV genome or antigenome encoding rBRSV/A2-NS1+2, rBRSV/A2-NS1+2GF, or rBRSV/A2-MSHGF.

* * * * *